United States Patent
Okuyama

(10) Patent No.: US 9,554,704 B2
(45) Date of Patent: Jan. 31, 2017

(54) LIVING ORGANISM BIOLOGICAL INFORMATION MEASUREMENT DEVICE

(75) Inventor: Koji Okuyama, Osaka (JP)

(73) Assignee: PANASONIC HEALTHCARE HOLDINGS CO., LTD., Tokyo (JP)

(*) Notice: Subject to any disclaimer, the term of this patent is extended or adjusted under 35 U.S.C. 154(b) by 670 days.

(21) Appl. No.: 14/000,968

(22) PCT Filed: Mar. 22, 2012

(86) PCT No.: PCT/JP2012/001995
§ 371 (c)(1),
(2), (4) Date: Aug. 22, 2013

(87) PCT Pub. No.: WO2012/127870
PCT Pub. Date: Sep. 27, 2012

(65) Prior Publication Data
US 2014/0012116 A1    Jan. 9, 2014

(30) Foreign Application Priority Data
Mar. 23, 2011  (JP) ................................. 2011-065068

(51) Int. Cl.
*G08B 21/00*    (2006.01)
*A61B 5/00*    (2006.01)
(Continued)

(52) U.S. Cl.
CPC ........... *A61B 5/0004* (2013.01); *A61B 5/0002* (2013.01); *A61B 5/14532* (2013.01);
(Continued)

(58) Field of Classification Search
CPC .............. A61B 2560/0247; A61B 2560/0252; A61B 2560/0266; A61B 2562/0295; A61B 2562/08; G01N 33/487; G06F 19/3418
(Continued)

(56) References Cited

U.S. PATENT DOCUMENTS

2002/0138275 A1    9/2002   Amano et al.
2003/0044854 A1    3/2003   Matzinger et al.
(Continued)

FOREIGN PATENT DOCUMENTS

JP    07-299273 A    11/1995
JP    2001-311989 A    11/2001
(Continued)

OTHER PUBLICATIONS

International Search Report for PCT/JP2012/001995 dated Jun. 26, 2012.

*Primary Examiner* — Mark Rushing
(74) *Attorney, Agent, or Firm* — Pearne & Gordon LLP

(57) ABSTRACT

Provided is a living organism information measurement device which users can easily and reliably operate. A living organism information measurement device for acquiring living organism information and generating measurement data relating to the information is provided with a device body, and a panel detachably attached to the device body. The device body comprises a control unit which executes a plurality of functions of the device body, a living organism information measurement unit which is connected to the control unit and generates the measurement data, and a first communication unit connected to the control unit. The panel comprises a second communication unit including a memory storing predetermined information. When the panel is attached to the device body, the first communication unit receives the predetermined information from the second communication unit. The control unit selects and executes a function corresponding to the received predetermined information among the plurality of functions.

14 Claims, 44 Drawing Sheets

(51) Int. Cl.
*G01N 33/487* (2006.01)
*G06F 19/00* (2011.01)
*A61B 5/145* (2006.01)
*A61B 5/1486* (2006.01)

(52) U.S. Cl.
CPC ......... *A61B 5/7445* (2013.01); *G01N 33/487* (2013.01); *G06F 19/3406* (2013.01); *A61B 5/1486* (2013.01); *A61B 2560/0247* (2013.01); *A61B 2560/0252* (2013.01); *A61B 2560/0266* (2013.01); *A61B 2562/0295* (2013.01); *A61B 2562/08* (2013.01); *G06F 19/3418* (2013.01)

(58) Field of Classification Search
USPC ...................................................... 340/691.8
See application file for complete search history.

(56) References Cited

U.S. PATENT DOCUMENTS

| | | |
|---|---|---|
| 2005/0019219 A1 | 1/2005 | Oshiman et al. |
| 2006/0020216 A1 | 1/2006 | Oishi et al. |
| 2006/0079809 A1 | 4/2006 | Goldberger et al. |
| 2006/0224413 A1* | 10/2006 | Kim .................. G06F 19/3418 705/2 |
| 2009/0018495 A1 | 1/2009 | Panduro |
| 2009/0216105 A1* | 8/2009 | Drucker ................ A61B 5/743 600/365 |
| 2009/0236237 A1 | 9/2009 | Shinno et al. |
| 2010/0268052 A1* | 10/2010 | Asama ............... A61B 5/14532 600/365 |
| 2011/0046548 A1 | 2/2011 | Sakata et al. |
| 2012/0103806 A1 | 5/2012 | Shinno et al. |
| 2012/0277669 A1 | 11/2012 | Sakata et al. |
| 2013/0297330 A1* | 11/2013 | Kamen ................. G06F 19/323 705/2 |

FOREIGN PATENT DOCUMENTS

| | | |
|---|---|---|
| JP | 2003-139772 A | 5/2003 |
| JP | 2004-221860 A | 8/2004 |
| JP | 2004-221926 A | 8/2004 |
| JP | 2005-100199 A | 4/2005 |
| JP | 2005-147688 A | 6/2005 |
| JP | 2006-026208 A | 2/2006 |
| JP | 2008-515483 A | 5/2008 |
| JP | 2008-546496 A | 12/2008 |
| JP | 2009-162676 A | 7/2009 |
| JP | 2010-191689 A | 9/2010 |
| JP | 2010-236933 A | 10/2010 |
| WO | 01/61340 A1 | 8/2001 |
| WO | 03/062812 A1 | 7/2003 |
| WO | 2007/066413 A1 | 6/2007 |
| WO | 2008/004565 A1 | 1/2008 |
| WO | 2009/131205 A1 | 10/2009 |

* cited by examiner

LIVING ORGANISM BIOLOGICAL INFORMATION MEASUREMENT DEVICE

TECHNICAL FIELD

The present invention relates to an apparatus that acquires biological information of for example blood and the like, and generates measurement data relating to the biological information.

BACKGROUND ART

The biological information measuring apparatus, for example, a blood sugar level measuring apparatus can be carried by a user, and is used to measure the blood sugar level by the user themself. The blood sugar level is measured in the following manner: a disposable blood sugar level sensor chip is mounted on the blood sugar level measuring apparatus, skin of a finger or the like is stuck by a separate puncture apparatus, and a small drop of blood effused from the skin is adhered thereon.

Since such a blood sugar level measuring apparatus is an electronic device, the apparatus is not limited to measurement of the blood sugar level, and it suffices to switch the measurement mode into a different function mode or change the display mode of the measurement result in accordance with a user (for example, refer to Patent Literature (hereinafter, abbreviated as PTL) 1), and it is possible to design the apparatus such that it has multiple functions such as transmission of an urgency signal (for example, refer to PTL 2).

Meanwhile, most of users of the blood sugar level measuring apparatus are the elderly or patients, and it is difficult for them to operate small buttons. Accordingly, in order to minimize the burden of the troublesome button operation, for example, a method of mounting a chip for switching functions in place of a blood sugar level sensor chip for measurement when a user changes the setting of the apparatus is disclosed (for example, refer to PTL 1).

CITATION LIST

Patent Literature

PTL 1: Japanese Patent Application Laid-Open No. 2005-147688
PTL 2: Japanese Patent Application Laid-Open No. 2004-221926

SUMMARY OF INVENTION

Technical Problem

In the blood sugar level measuring apparatus disclosed in PTL 1, it is possible to avoid the button operation. However, the chip for switching functions has to be separated from the apparatus when normal measurement of the blood sugar level is performed. Further, once the chip for switching functions is separated and is not linked with the apparatus, it is difficult to know which function the setting is made for, and thus a user might become confused during the operation. Accordingly, an object of the present invention is to provide a biological information measuring apparatus capable of assisting a user to easily and reliably perform the operation.

Solution to Problem

According to a first aspect, there is provided a biological information measuring apparatus for acquiring biological information and generating measurement data relating to the biological information, the biological information measuring apparatus including: an apparatus main body; and a panel that is detachably mounted on the apparatus main body. The apparatus main body has a control unit that executes a plurality of functions in the apparatus main body, a biological information measuring section that is connected to the control unit and generates the measurement data, and a first communication unit that is connected to the control unit. The panel has a second communication unit that includes a memory in which predetermined information is stored. When the panel is mounted on the apparatus main body, the first communication unit receives the predetermined information from the second communication unit. The control unit selects and executes at least one of the plurality of functions corresponding to the received predetermined information.

With such a configuration of the biological information measuring apparatus, it is possible to select and execute the predetermined function once the panel is mounted. Hence, a user is able to easily and reliably operate the biological information measuring apparatus.

In the biological information measuring apparatus, the first communication unit may be an antenna and the second communication unit may be an RF-ID unit.

In the biological information measuring apparatus, the first communication unit and the second communication unit may be respectively disposed on the apparatus main body and the panel so as to face each other when the panel is mounted on the apparatus main body.

In the biological information measuring apparatus, the control unit may further have a program memory, and the predetermined information may be stored in the program memory of the control unit, and may be information corresponding to a control program for executing the at least one of the functions.

In the biological information measuring apparatus, the predetermined information may be a control program with which the control unit executes the at least one of the functions.

In the biological information measuring apparatus, the control unit may further have a data storage section that stores the measurement data, and the control program may be a program for executing a function of preventing the measurement data from being stored in the data storage section.

In the biological information measuring apparatus, the apparatus main body may further have a main body display section that is connected to the control unit and displays the measurement data, and the control program may be a program for executing a function of displaying the measurement data on the main body display section in an enlarged manner or a reduced manner.

In the biological information measuring apparatus, the apparatus main body may further have a communication section that is connected to the control unit and communicates with a different apparatus, and the control program may be a program that transmits the measurement data from the communication section to the different apparatus.

In the biological information measuring apparatus, the apparatus main body may further have a main body display section that is connected to the control unit and that displays information which is arbitrarily selected. The control program may be a program for displaying a menu for a medical staff on the main body display section and is for performing a process by the medical staff.

In the biological information measuring apparatus, the apparatus main body may have a voice output section that is connected to the control unit, and the control unit may cause the voice output section to output a voice on the basis of the received predetermined information.

In the biological information measuring apparatus, the panel may have a sound output section, and the control unit and the sound output section may be connected when the panel is mounted on the apparatus main body. In this case, the control unit causes the sound output section to output data, which relates to measurement of the biological information, as an audible sound on the basis of the received predetermined information.

In the biological information measuring apparatus, the apparatus main body may further have an alarm section that is connected to the control unit and sounds an alarm. In this case, the control unit causes the alarm section to sound the alarm when the control unit determines that communication between the first communication unit and the second communication unit is suspended on a basis of fact that at least one of conditions of (i) a predetermined time or more passes from the determination that the communication is suspended and (ii) the measurement data represents an abnormal value is satisfied.

In the biological information measuring apparatus, the apparatus main body may further have a main body display section that is connected to the control unit and displays information which is arbitrarily selected. In this case, the control unit causes the main body display section to display warning information when the control unit determines that communication between the first communication unit and the second communication unit is suspended on a basis of fact that at least one of conditions of (i) a predetermined time or more passes from the determination that the communication is suspended and (ii) the measurement data represents an abnormal value is satisfied.

In the biological information measuring apparatus, the apparatus main body may further have a communication section that is connected to the control unit and communicates with a different apparatus, and a current position acquisition section that is connected to the control unit and acquires current position information of the apparatus. In this case, the control unit transmits the current position information from the communication section to a different apparatus when the control unit determines that communication between the first communication unit and the second communication unit is suspended on a basis of fact that at least one of conditions of (i) a predetermined time or more passes from the determination that the communication is suspended and (ii) the measurement data represents an abnormal value is satisfied.

In the biological information measuring apparatus, the apparatus main body may further have a communication section that is connected to the control unit and communicates with a different apparatus. In this case, the control unit acquires instruction information based on the measurement data from the different apparatus through the communication section when the control unit determines that communication between the first communication unit and the second communication unit is suspended on a basis of fact that at least one of conditions of (i) a predetermined time or more passes from the determination that the communication is suspended and (ii) the measurement data represents an abnormal value is satisfied.

In the biological information measuring apparatus, the panel may further have a function display section that displays function information corresponding to the predetermined information.

In the biological information measuring apparatus, the apparatus main body may further have a main body display section that is connected to the control unit and displays information which is arbitrarily selected. In this case, the control unit causes the main body display section to display information corresponding to the function information displayed on the function display section of the panel.

In the biological information measuring apparatus, the apparatus main body may have a dial on a side portion thereof, and the control unit may cause the main body display section to display an information relating to measurement performed by the apparatus main body or the function information on the main body display section in an enlarged manner or a reduced manner, according to an operation of the dial.

In the biological information measuring apparatus, the function information displayed on the function display section of the panel may represent an operation manual of the apparatus.

In the biological information measuring apparatus, while the biological information is measured by the apparatus main body, the control unit may cause the main body display section to display the operation manual describing a process of the measurement in accordance with measurement progress performed by the apparatus main body.

According to another aspect, there is provided a biological information measuring apparatus for acquiring biological information and generating measurement data relating to the biological information, the biological information measuring apparatus including: an apparatus main body; and a panel that is detachably mounted on the apparatus main body. The apparatus main body has a control unit that executes a plurality of functions in the apparatus main body, a biological information measuring section that is connected to the control unit and generates the measurement data, and an antenna that is connected to the control unit. The panel has an RF-ID unit that includes a memory in which predetermined information is stored. When the panel is mounted on the apparatus main body, the antenna and the RF-ID unit are able to communicate, and are respectively disposed on the apparatus main body and the panel so as to be opposed.

According to a further aspect, there is provided a biological information measuring apparatus kit for acquiring biological information and generating measurement data relating to the biological information, the biological information measuring apparatus kit including: one apparatus main body; and a plurality of panels that are mounted on the apparatus main body so as to be replaceable. The apparatus main body may have a control unit that executes a plurality of functions in the apparatus main body, a biological information measuring section that is connected to the control unit and generates the measurement data, and a first communication unit that is connected to the control unit. Each of the plurality of panels has a second communication unit that includes a memory in which different predetermined information is stored. When one of the plurality of panels is mounted on the apparatus main body, the first communication unit receives the predetermined information from the second communication unit of one of the panels. The control unit selects and executes at least one of the plurality of functions corresponding to the received predetermined information.

According to a further aspect, there is provided a biological information measuring apparatus for acquiring biological information and generating measurement data relating to the biological information, the biological information measuring apparatus including: an apparatus main body; and a panel mount portion through which a panel having a memory storing predetermined information can be detachably mounted on the apparatus main body. The apparatus main body may have a control unit that executes a plurality of functions in the apparatus main body, and a biological information measuring section that is connected to the control unit and generates the measurement data. The predetermined information is input from the memory of the panel when the panel is mounted on the panel mount portion. The control unit selects and executes at least one of the plurality of functions corresponding to the input predetermined information.

According to a further aspect, there is provided a biological information measuring apparatus for acquiring biological information and generating measurement data relating to the biological information, the biological information measuring apparatus including: an apparatus main body; and a panel mount portion through which a panel having an identification section for determining identification information can be detachably mounted on the apparatus main body. The apparatus main body may have a control unit that executes a plurality of functions in the apparatus main body, and a biological information measuring section that is connected to the control unit and generates the measurement data. The control unit determines the identification information from the identification section of the panel when the panel is mounted on the panel mount portion. The control unit selects and executes at least one of the plurality of functions corresponding to the determined identification information.

According to a further aspect, there is provided a biological information measuring apparatus for acquiring biological information and generating measurement data relating to the biological information, the biological information measuring apparatus including: an apparatus main body; and a panel mount portion through which a panel having a temperature sensor for measuring a temperature can be detachably mounted on the apparatus main body. The apparatus main body may have a control unit that executes a plurality of functions in the apparatus main body, and a biological information measuring section that is connected to the control unit and generates the measurement data. The control unit receives the measured temperature from the temperature sensor of the panel when the panel is mounted on the panel mount portion. The control unit corrects data, which is measured by the biological information measuring section, on the basis of the measured temperature.

According to a further aspect, there is provided a biological information measuring apparatus for acquiring biological information and generating measurement data relating to the biological information, the biological information measuring apparatus including: an apparatus main body; and a panel mount portion through which a panel having an identification code for identifying a measurement target can be detachably mounted on the apparatus main body. The apparatus main body may have a control unit that executes a plurality of functions in the apparatus main body, and a biological information measuring section that is connected to the control unit and generates the measurement data. The control unit determines the measurement target on the basis of the identification code of the panel when the panel is mounted on the panel mount portion. The control unit may cause the biological information measuring section to execute measurement on the basis of the determined measurement target.

According to a further aspect, there is provided a biological information measuring apparatus for acquiring biological information and generating measurement data relating to the biological information, the biological information measuring apparatus including: an apparatus main body; and a panel mount portion through which a panel having an identification code for identifying a locality can be mounted on the apparatus main body. The apparatus main body may have a control unit that executes a plurality of functions in the apparatus main body, and a biological information measuring section that is connected to the control unit and generates the measurement data. The control unit determines the locality on the basis of the identification code of the panel when the panel is mounted on the panel mount portion. The control unit selects and executes at least one of the plurality of functions on the basis of the determined locality.

Advantageous Effects of Invention

As described above, according to the present invention, a user is able to easily and reliably perform the operation of the biological information measuring apparatus.

DESCRIPTION OF EMBODIMENTS

1. Embodiment 1

1.1 Configuration of Blood Sugar Level Measuring Apparatus

Figure 1:
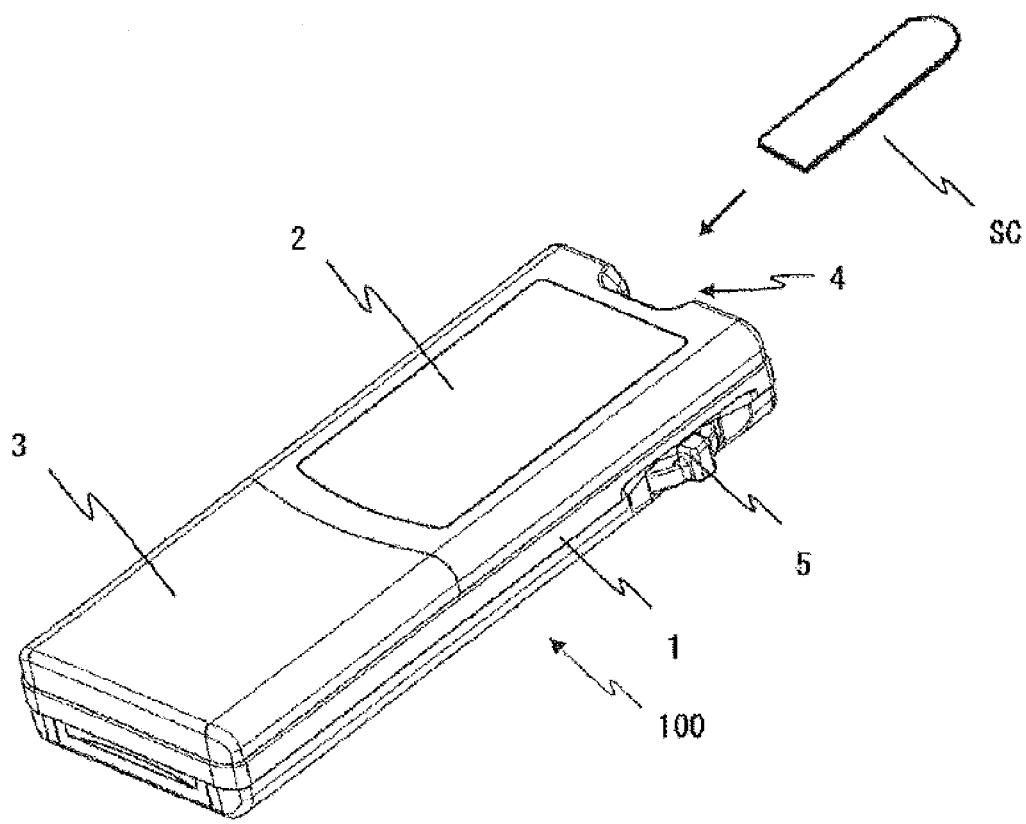
FIG. 1 is a perspective view of a blood sugar level measuring apparatus according to Embodiment 1.
Figure 2:
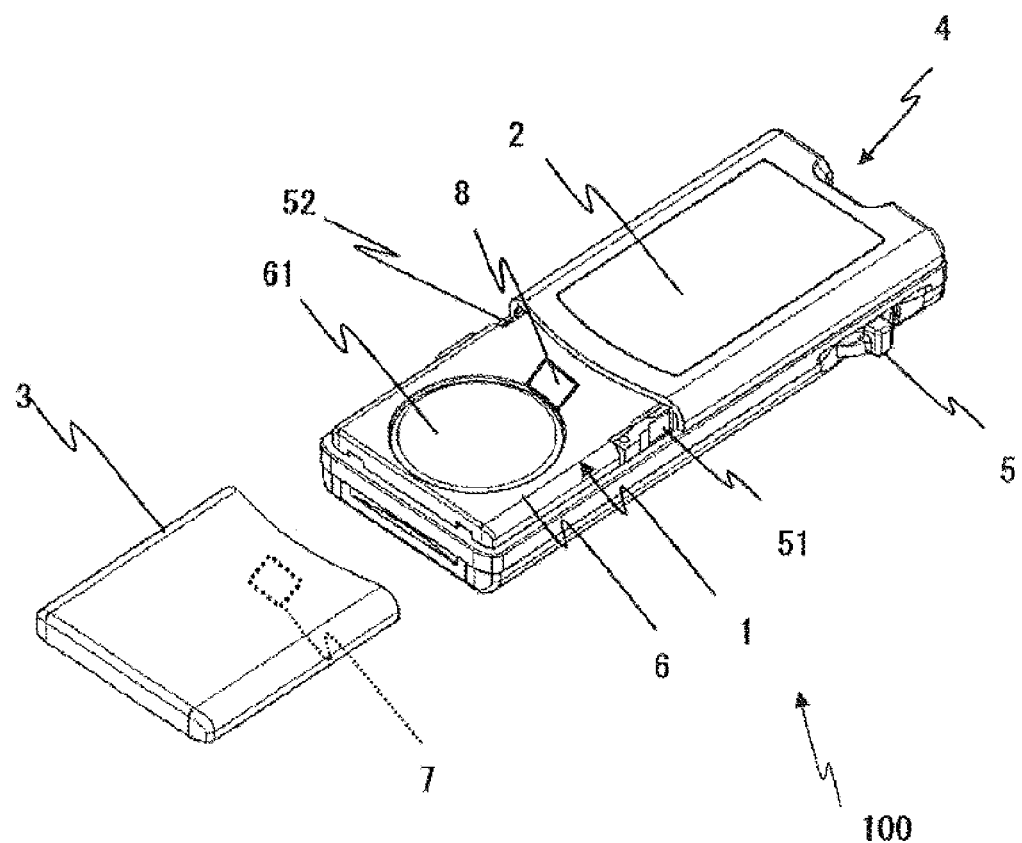
FIG. 2 is a perspective view illustrating a state in which a panel of the blood sugar level measuring apparatus according to Embodiment 1 is detached.

FIGS. 1 and 2 show appearances of blood sugar level measuring apparatus (shown as an example of the biological information measuring apparatus) 100 according to Embodiment 1 of the present invention.

As shown in FIG. 1, blood sugar level measuring apparatus 100 according to the present embodiment includes apparatus main body 1, and plate-like panel 3 which can be detachably mounted on apparatus main body 1. A user inserts and mounts disposable blood sugar level sensor chip SC into sensor insertion opening 4 of apparatus main body 1. Skin of a user's finger or the like is stuck by a separate puncture apparatus, and a small drop of blood effused from the skin is adhered onto blood sugar level sensor chip SC. Thereby, the blood sugar level is measured. Further, as shown in FIG. 2, a user is able to replace battery 61 by detaching panel 3 from apparatus main body 1.

1.1.1 Configuration of Apparatus Main Body

As shown in FIG. 2, apparatus main body 1 has a substantially rectangular shape. Apparatus main body 1 includes: main body display section 2 that is provided on the surface thereof; sensor insertion opening 4 that is provided on an upper side terminal thereof; operational section 5 that is provided on a single side portion thereof; battery housing section 6 in which battery 61 is mounted on the portion covered by panel 3; RF-ID reading antenna 8 (first communication unit) to be described later; and engagement sections 51 and 52 through which panel 3 is fixed onto apparatus main body 1. In addition, in apparatus main body 1, as shown in FIG. 2, a portion (panel mount portion), on which panel 3 can be mounted, is formed in a portion other than main body display section 2.

Main body display section 2 is a display such as a liquid crystal display or an organic EL display, and displays information, such as the measured blood sugar level or a function menu, to a user.

Sensor insertion opening 4 is an insertion opening of a sensor chip through which blood sugar level sensor chip SC is mounted on apparatus main body 1.

The operational section 5 includes a button, a switch, a slide, a lever, a dial, and the like which a user handles with a finger to operate the apparatus.

The battery housing section 6 houses and is equipped with battery 61 as a power supply of blood sugar level measuring apparatus 100. Here, a disposable button battery is used as battery 61, but the battery is not limited to this, and may be a chargeable battery such as an alkali battery or a Li-ion battery.

As will be described later, RF-ID reading antenna 8 reads information of the RF-ID unit provided on panel 3, and transmits the information to the control unit to be described later.

Engagement sections 51 and 52 have a mechanism that fixes panel 3 onto apparatus main body 1 in engagement with the portion corresponding to panel 3 when panel 3 is mounted.

1.1.2 Configuration of Panel

Panel 3 having a plate-like body is mounted on apparatus main body 1, and functions as a cover of battery 61. Panel 3 has RF-ID tag (second communication unit) 7 which is fixed onto the rear side thereof. Here, the RF-ID tag is an IC tag (or IC chip) that performs wireless communication at a short distance using an electromagnetic field, a radio wave, or the like. In the present embodiment, as will be described later, a passive-type RF-ID tag is used, but an active type may be used.

Figure 3:
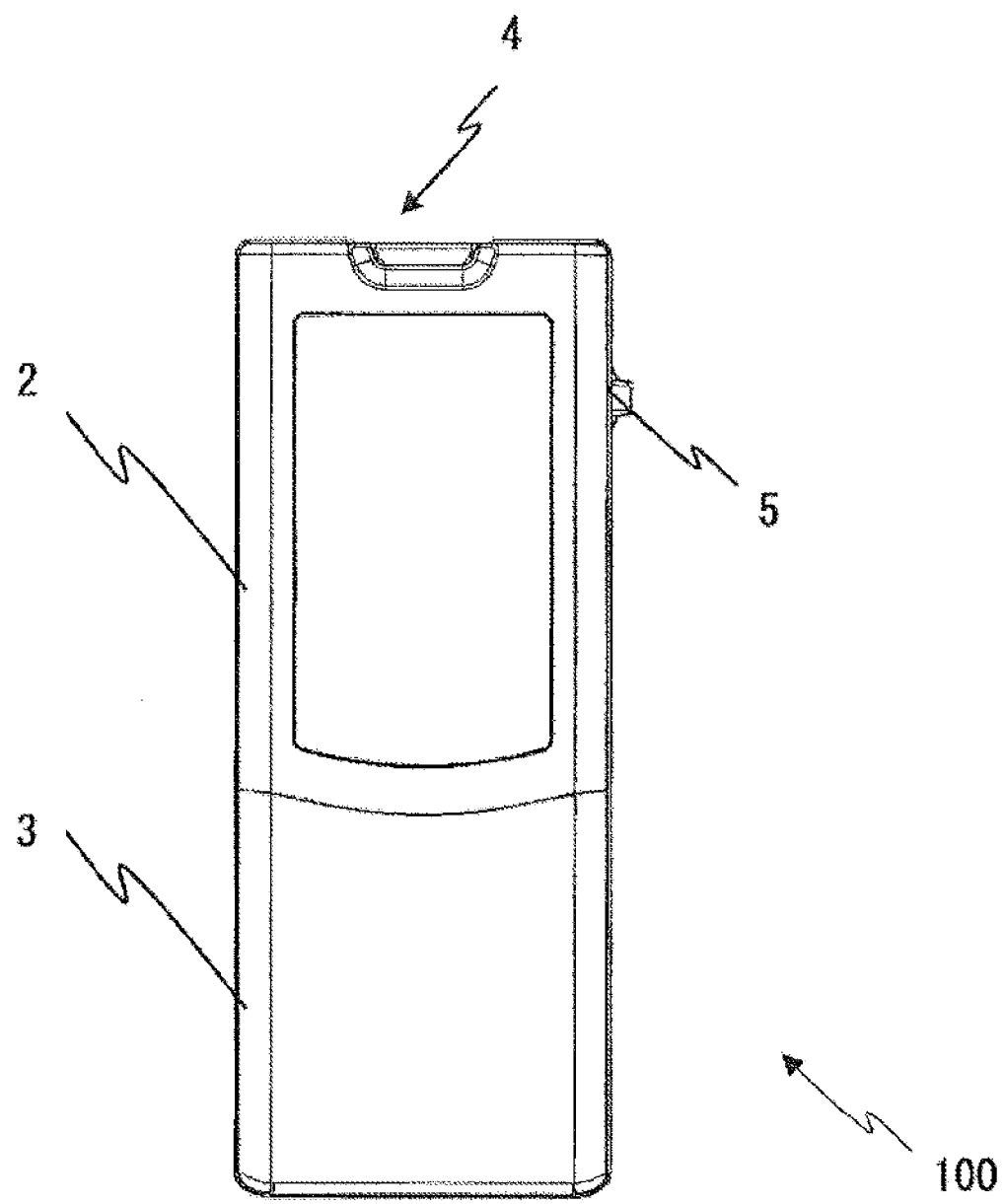
FIG. 3 is a front view of the blood sugar level measuring apparatus according to Embodiment 1.

As shown in FIG. 3, when panel 3 is mounted on apparatus main body 1, RF-ID reading antenna 8 is provided on the portion of apparatus main body 1 facing to RF-ID tag 7. When panel 3 is mounted on apparatus main body 1, RF-ID tag 7 provided on panel 3 and RF-ID reading antenna 8 provided on apparatus main body 1 become able to communicate, and the information of RF-ID tag 7 is read by RI-ID reading antenna 8. Further, as will be described later, apparatus main body 1 determines whether panel 3 is mounted, through the reading.

In addition, in blood sugar level measuring apparatus 100 similar to the present embodiment, there is an increase in the demand to use panel 3 which can be replaced in accordance with each user's request. In order to cope with such a demand, the number of produced panels 3 becomes extremely large. Thus, in some cases, for a production management of panel 3, RF-ID tag 7 is mounted on panel 3. The RF-ID tag 7 stores the production management information of panel 3 in memory 71 to be described later. In the following description of the present embodiment, RF-ID tag 7 attached onto panel 3 is used.

Here, RF-ID tag 7 on panel 3 side and RF-ID reading antenna 8 on apparatus main body 1 side are used for wireless communication at an extremely short distance. The distance between both of them is set to a distance at which first communication is possible since when panel 3 is appropriately mounted on apparatus main body 1.

1.2 Control Unit

Figure 4:
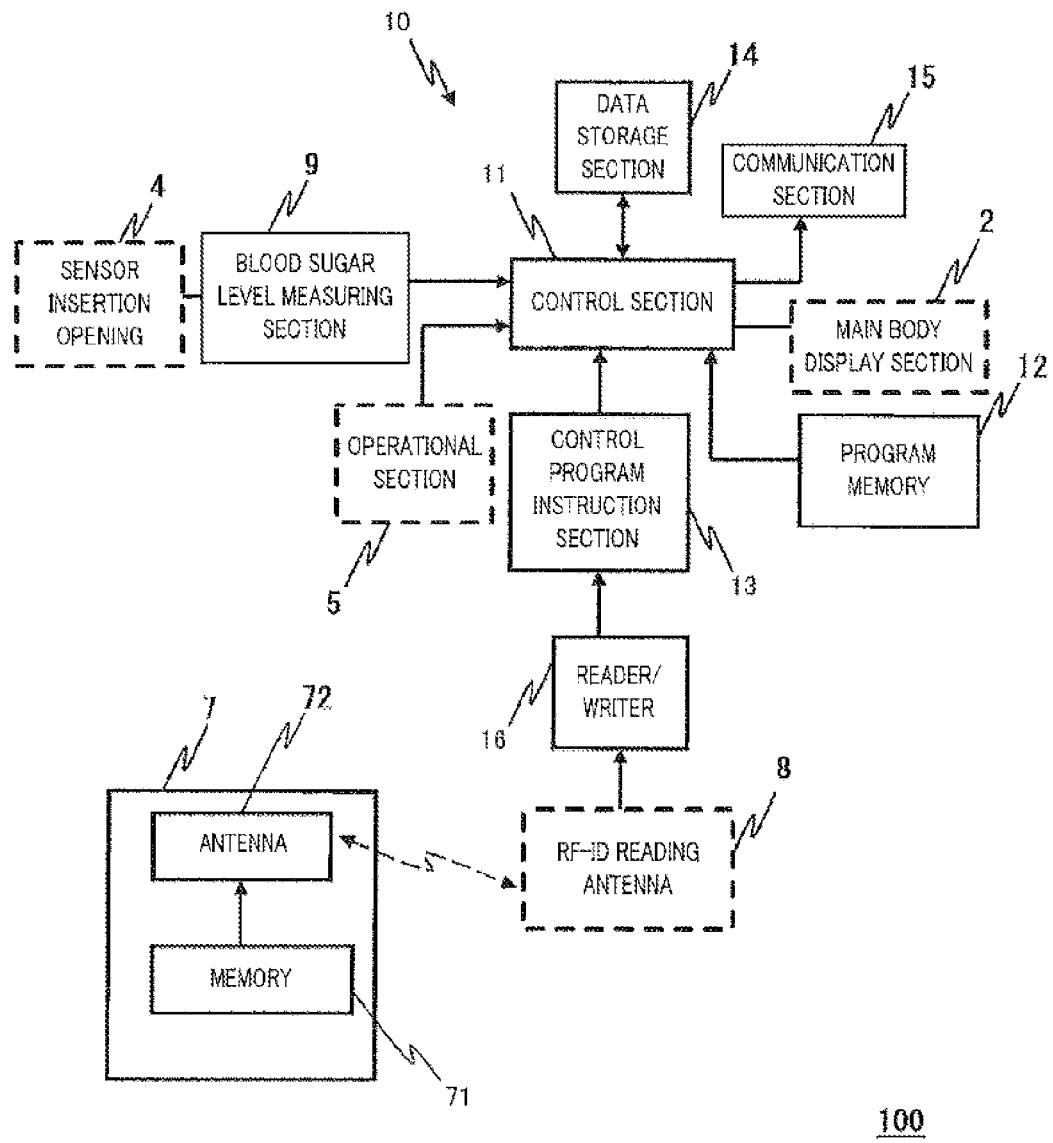
FIG. 4 is a configuration diagram of a control unit of the blood sugar level measuring apparatus according to Embodiment 1.

FIG. 4 shows a configuration of control unit 10 provided inside apparatus main body 1 of blood sugar level measuring apparatus 100. As shown in FIG. 4, control unit 10 includes control section 11, program memory 12, control program instruction section 13, data storage section 14, communication section 15, and reader/writer 16.

Control section 11 is connected to main body display section 2 of apparatus main body 1, operational section 5, and blood sugar level measuring section 9. Control section 11 commands main body display section 2 to display information. Control section 11 generates a control command according to the signal from operational section 5 operated by a user, and transmits the command to the respective sections.

Blood sugar level measuring section 9, which is connected to control section 11, measures the blood sugar level of the blood drop adhered onto blood sugar level sensor chip SC inserted through sensor insertion opening 4. Specifically, first, an electrode (not shown in the drawing) for measurement of blood sugar level sensor chip SC is electrically connected to blood sugar level measuring section 9 through a sensor connector (not shown in the drawing) which is provided at sensor insertion opening 4. When a blood drop is adhered onto blood sugar level sensor chip SC, response current is generated by oxidation-reduction reaction which is a signal from blood sugar level sensor chip SC. Blood sugar level measuring section 9 converts the response current into a voltage, performs A/D conversion so as to convert the voltage value into a predetermined digital value, and thereafter inputs the value to control section 11. The value is stored as concentration data of blood, for example, glucose concentration data, which represents the blood sugar level, in data storage section 14.

Program memory 12 stores a plurality of control programs which are read by control section 11 in order to execute functions in the apparatus.

Control program instruction section 13 commands control section 11 to read a certain control program from program memory 12.

As described above, data storage section 14 stores the measured blood sugar level (measurement data) in response to the command issued from control section 11.

Communication section 15 transmits the blood sugar level data, which is stored in data storage section 14, and the like to a communication apparatus apart from the measuring apparatus, in response to the command issued from control section 11.

Reader/writer 16 reads control information (predetermined information) which is received by RF-ID reading antenna 8, and transmits the information to control program instruction section 13. The control information, which is received by RF-ID reading antenna 8, is defined as the information which is stored in RF-ID tag 7.

As shown in FIG. 4, RF-ID tag 7 has memory 71 and antenna 72 connected to memory 71. Memory 71 stores the control information corresponding to panel 3 onto which RF-ID tag 7 is fixedly attached. Here, the control information is defined as information for the control programs executed by blood sugar level measuring apparatus 100, for example, information which is for indentifying the control programs.

In a state where RF-ID tag 7 and RF-ID reading antenna 8 of apparatus main body 1 are able to communicate (that is, a state where panel 3 is mounted on apparatus main body 1), RF-ID reading antenna 8 receives the control information from RF-ID tag 7, and the information is read by reader/writer 16 of apparatus main body 1. Control program instruction section 13 commands control section 11 to execute the corresponding control program among programs stored in program memory 12, in response to the control information which is read by reader/writer 16.

It should be noted that, in FIG. 4, although battery 61 is not shown, all the members provided on control section 11, that is, the members in apparatus main body 1, uses battery 61 as a power supply. When an electric power is supplied from battery 61, radio waves are intermittently transmitted from RF-ID reading antenna 8. Antenna 72 of RF-ID tag 7, by which the radio waves are received, obtains electromotive force by smoothing and rectifying the radio waves. Thereby, the control information recorded in memory 71 is sent from antenna 72 to RF-ID reading antenna 8 by the radio waves.

Further, control section 11 and control program instruction section 13 are constituted by, for example, arithmetic processing units such as processors or CPUs. In the present embodiment, these sections are described as two functional sections, but may be one section.

1.3 Operation of Blood Sugar Level Measuring Apparatus

Figure 5:
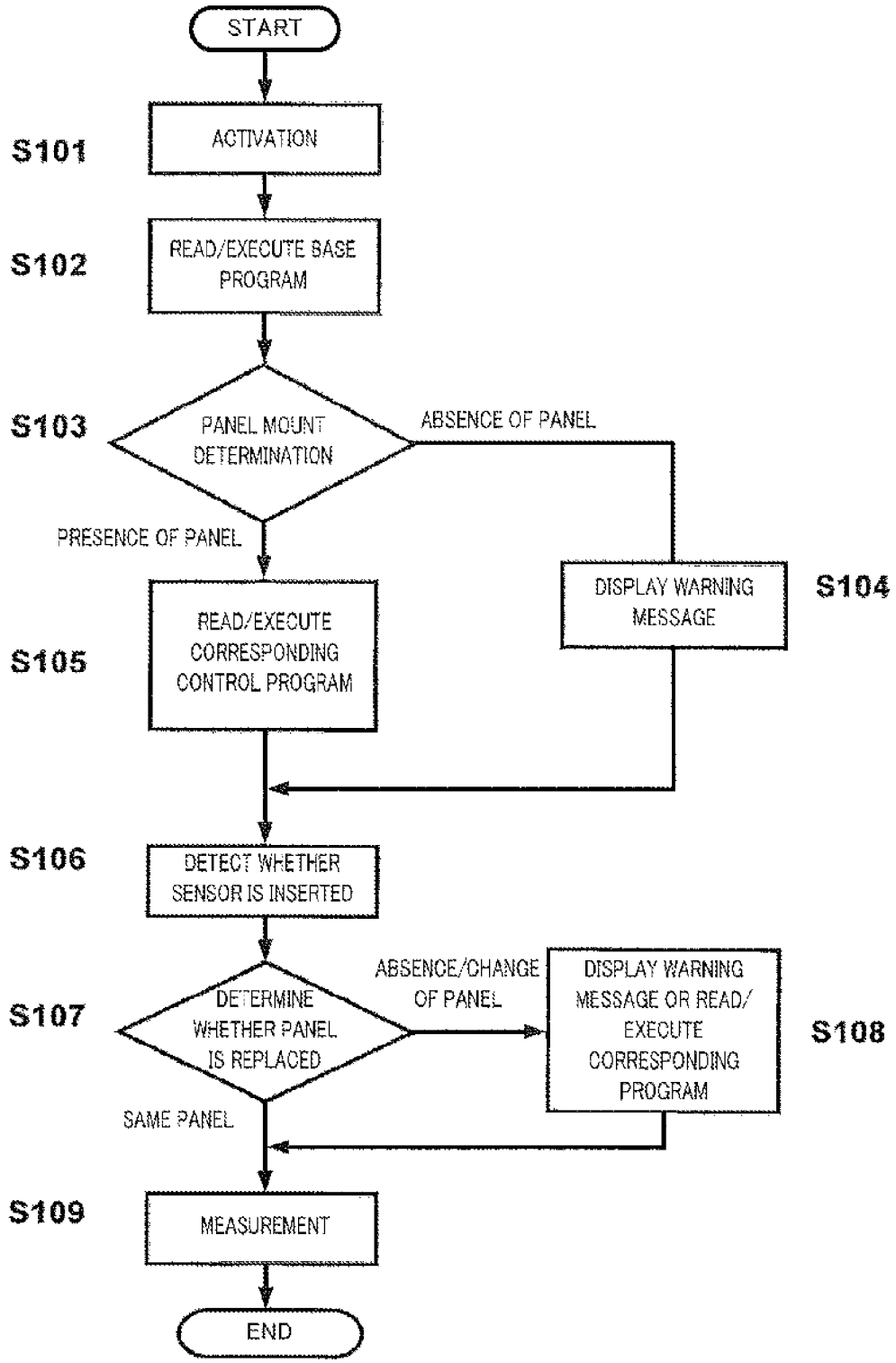
FIG. 5 is a flowchart illustrating a process performed by the control unit of the blood sugar level measuring apparatus according to Embodiment 1.

FIG. 5 is a flowchart illustrating an operation of control unit 10 of blood sugar level measuring apparatus 100.

Step S101: when a user operates operational section 5, the power supply is ON, and the respective sections of the apparatus are activated.

Step S102: control section 11 of control unit 10 reads a base program from program memory 12, and executes the program.

Step S103: control section 11 determines whether or not panel 3 is mounted on apparatus main body 1, as the power supply is ON. The determination as to whether panel 3 is mounted is performed by determining whether the control information is received from RF-ID tag 7 of panel 3 which is activated by the electric power generated by the radio waves intermittently transmitted by RF-ID reading antenna 8. Control section 11 determines that panel 3 is not mounted if there is no command issued from control program instruction section 13 as described above. And then, the control section 11 advances the process to step S104. In contrast, control section 11 advances the process to step S105 if there is the command issued from control program instruction section 13 as described above.

Step S104: control section 11 causes main body display section 2 to display information for warning that panel 3 is not mounted on apparatus main body 1, and the process advances to step S106. In addition, as will be described later, even when the warning is displayed in step S104, the blood sugar level can be measured by blood sugar level measuring section 9.

Step S105: in contrast, if control section 11 determines that panel 3 is mounted on apparatus main body 1, that is, if the control information received by RF-ID reading antenna 8 can be transferred to control program instruction section 13 through reader/writer 16, control section 11 performs the following process. Control section 11 reads and executes the control program, corresponding to the control information which is read from current RF-ID tag 7, among a plurality of control programs in program memory 12, in response to the command issued from control program instruction section 13.

Step S106: when blood sugar level sensor chip SC is inserted into sensor insertion opening 4, blood sugar level measuring section 9 detects the insertion of the sensor chip.

In step S106, it is checked whether sensor chip SC is correctly mounted on apparatus main body 1. For example, it is determined whether or not sensor chip SC is mounted upside down. Further, when sensor chip SC is provided with a function for identifying a model thereof, by identifying the model, it is determined whether the model matches with the model information of apparatus main body 1 or the model information included in the control information which is stored in RF-ID tag 7 of panel 3.

Step S107: after blood sugar level sensor chip SC is mounted, control section 11 determines whether or not panel 3 is mounted on apparatus main body 1, and whether panel 3 is replaced after the previous panel mount determination. The determination as to whether panel 3 is mounted is performed by: determining whether the control information is received from RF-ID tag 7 of panel 3 in which the electric power is generated by the radio waves intermittently transmitted by RF-TD reading antenna 8; and determining whether the received control information is the same as that at the previous panel mount determination.

In addition, if panel 3 is not mounted on apparatus main body 1, the base program is executed up to step S107; and if panel 3 is mounted on apparatus main body 1, the corresponding control program is executed. Further, in the present embodiment, the determination of panel 3 is limited to be performed when the power supply is applied and when blood sugar level sensor chip SC is mounted. Thereby, the consumption of the battery caused by constant communication of RF-ID tag 7 with RF-ID reading antenna 8 is suppressed.

Step S108: control section 11 causes main body display section 2 to display a warning that panel 3 is not mounted on apparatus main body 1. Further, when panel 3 is changed with another panel, control section 11 reads and executes the control program from program memory 12, the control program corresponding to the control information received from RF-ID tag 7 of panel 3. And then control section 11 causes main body display section 2 to display a warning that the executed control program is changed. The selective reading of the control program from program memory 12 of control section 11 is performed by control program instruction section 13 as described above.

Step S109: the blood sugar level is measured by blood sugar level measuring section 9. In addition, when blood sugar level sensor chip SC is inserted into blood sugar level measuring section 9 in a state where panel 3 is not mounted on apparatus main body 1, the measured blood sugar level data is set not to be stored in data storage section 14 even though the blood sugar level is measured.

In the above-mentioned process, the process depending on the mounted panel 3 is performed. Examples of specific processes depending on panels 3 will be described later, and can include the following process: the measurement data including the blood sugar level data is transmitted, the measurement result is displayed on main body display section 2 in an enlarged manner, and the displayed measurement result is not stored in data storage section 14.

It should be noted that the contents of the process is just an example, and the procedure thereof is not limited to the above description. For example, in order to suppress the consumption of the battery in the above process, the determination of panel 3 is performed when supplying the power supply and when mounting blood sugar level sensor chip SC. However, the determination of the panel mount/change may be performed whenever the panel is changed or separated.

Further, for example, in response to the situation where panel 3 is mounted on apparatus main body 1, the main power supply of apparatus main body 1 may be turned ON. In this case, the apparatus main body 1 is normally in the standby mode for electric power saving. Thus, by detecting that panel 3 is mounted, the above-mentioned processes of steps S101, S102 and S105 are executed. In such a manner, it is not necessary to display the warning that panel 3 is not mounted.

1.4 Panel Examples

1.4.1 Panel Example 1

Figure 6:
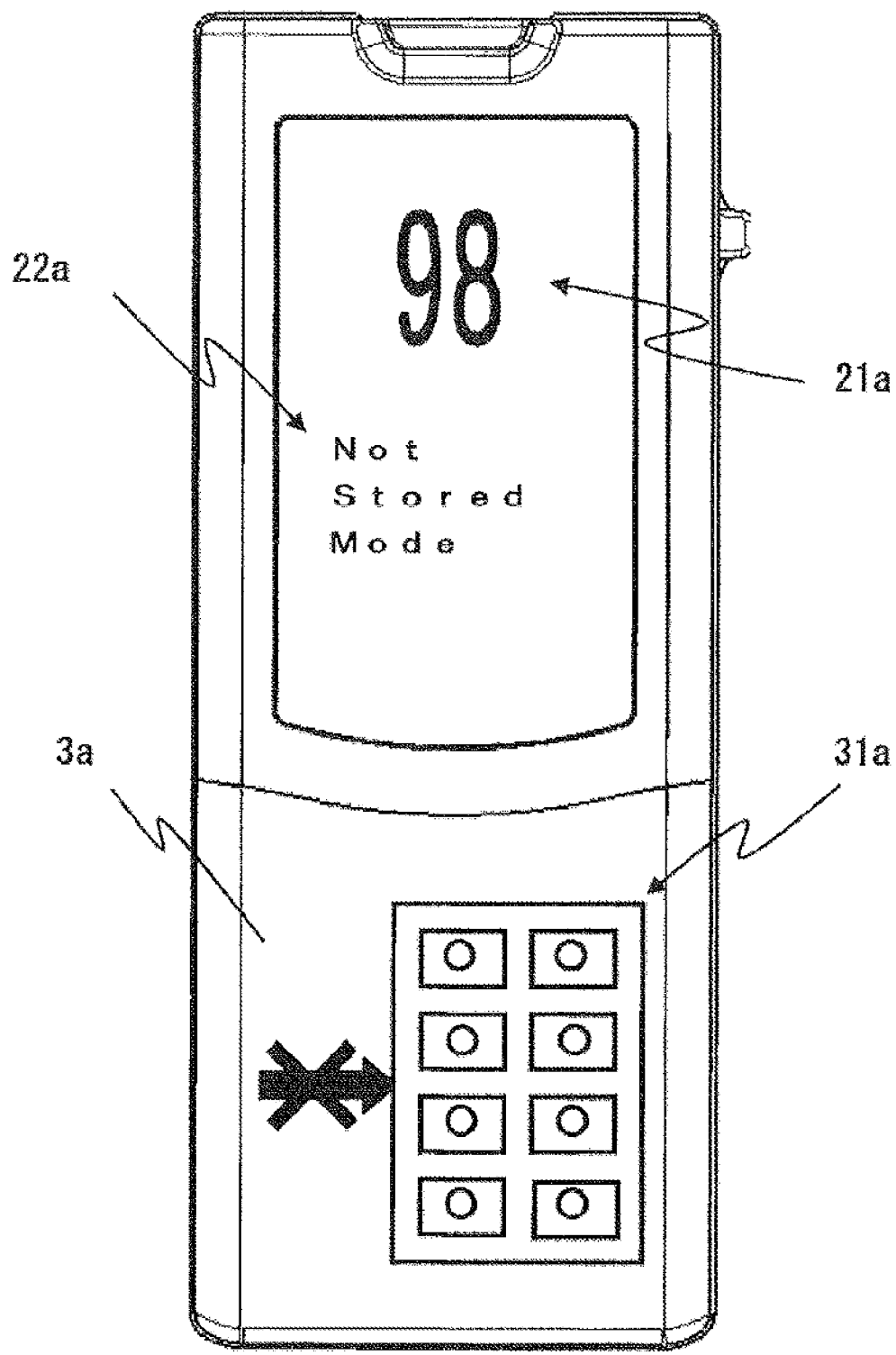
FIG. 6 is a front view of a blood sugar level measuring apparatus according to Panel Example 1 of Embodiment 1.

FIG. 6 shows a state where panel 3 of FIG. 1 is changed with panel 3a. Specifically, panel 3a is used when apparatus main body 1 is lent to other person than the owner. As shown in FIG. 6, function display section 31a is provided on the surface of panel 3a, the section 31a causing a user to recognize that the measurement data is not stored in data storage section 14 shown in FIG. 4. Further, the control information is stored in the RF-ID tag (not shown in the drawing) which is provided on the rear side of panel 3a, the control information corresponding to the control program issuing the command not to store the measurement data in data storage section 14.

If panel 3a is mounted on apparatus main body 1, it is determined that panel 3 is panel 3a in step S103 or step S107 of FIG. 5. Then, in a similar manner to the process of FIG. 5, the control information of the RF-ID tag provided on panel 3a is received by RF-ID reading antenna 8, and the control information is read by reader/writer 16. Control section 11 reads and executes the control program, corresponding to the control information from program memory 12, in response to the command issued from control program instruction section 13. As a result, only the function of measuring the blood sugar level is executed, and the measurement data is prevented from being stored in data storage section 14. As shown in FIG. 6, measurement data 21a (here, blood sugar level "98") is displayed on main body display section 2. In addition, caution message 22a (here, "Not Stored Mode") that measurement data 21a is not stored in data storage section 14 is displayed below measurement data 21a.

1.4.2 Panel Example 2

Figure 7:
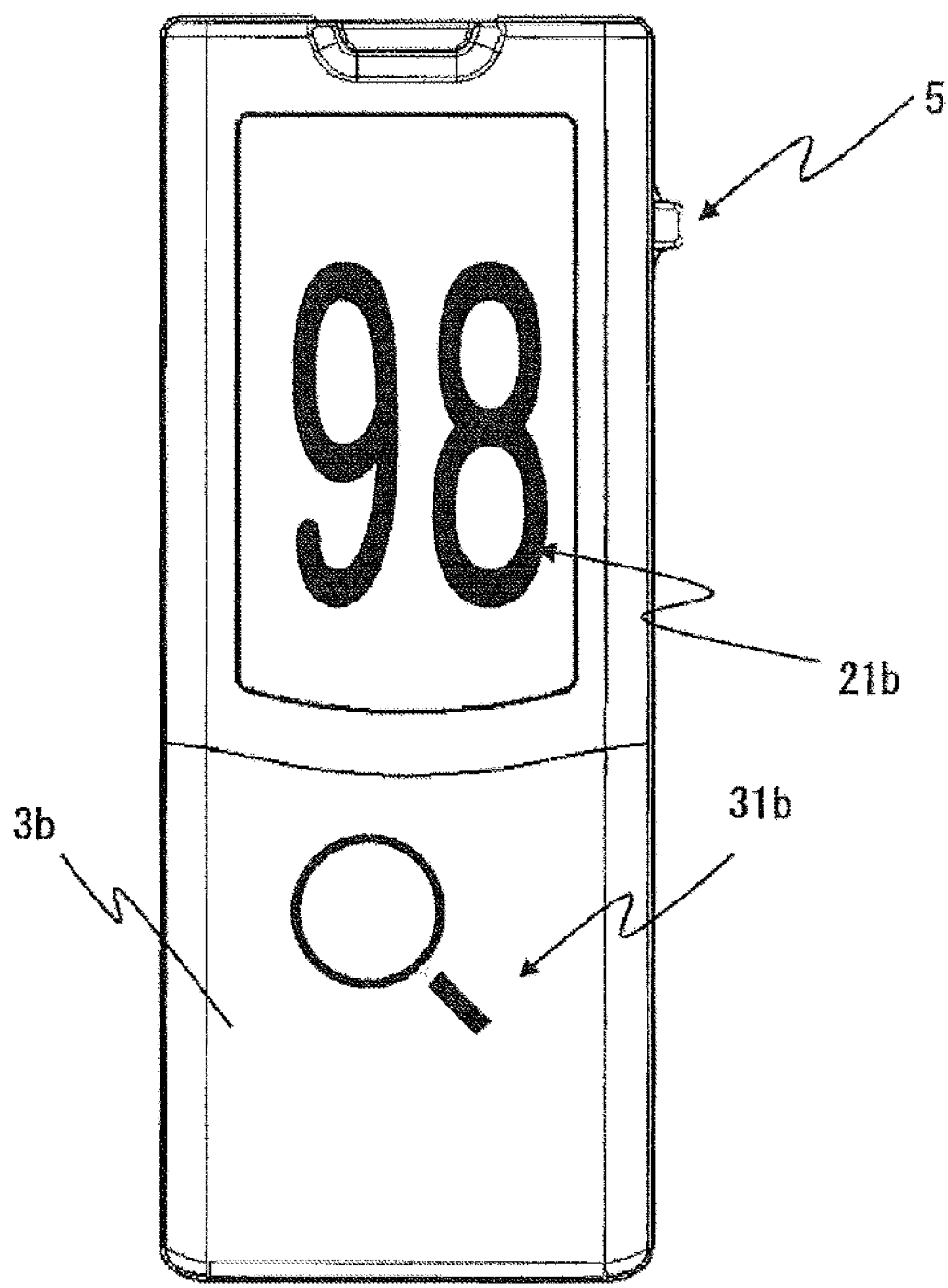
FIG. 7 is a front view of a blood sugar level measuring apparatus according to Panel Example 2 of Embodiment 1.

FIG. 7 shows a state where panel 3 of FIG. 1 is panel 3b. Specifically, panel 3b is for displaying in enlarged manner on main body display section 2. As shown in FIG. 7, function display section 31b is provided on the surface of panel 3b, the section 31b causing a user to recognize that the measurement data is displayed on main body display section 2 in an enlarged manner. Further, the control information is stored in the RF-ID tag (not shown in the drawing) which is provided on the rear side of panel 3b, the control information corresponding to the control program issuing the command to display the measurement data on main body display section 2 in an enlarged manner.

If panel 3b is mounted on apparatus main body 1, it is determined that panel 3 is panel 3b in step S103 or step S107 of FIG. 5. Then, in a similar manner to the process of FIG. 5, the control information of the RF-ID tag provided on panel 3b is received by RF-ID reading antenna 8, and the control information is read by reader/writer 16. Control section 11 reads and executes the control program, corresponding to the control information from program memory 12, in response to the command issued from control program instruction section 13. As a result, as shown in FIG. 7, measurement data 21b is displayed on main body display section 2.

Alternatively, the control program which changes the display mode of the data on main body display section 2 can be a program for displaying in a reduced manner or in a different font as well as in an enlarged manner according to the needs of a user.

That is, with the configuration in which panel 3b is mounted on apparatus main body 1, a user is able to optionally select enlarged manner or reduced manner by rotating a dial of operational section 5, for example. Further, the information displayed on main body display section 2 in an enlarged manner or a reduced manner is not limited to the measurement data, and can be any type of data relating to the measurement performed by apparatus main body 1.

1.4.3 Panel Example 3

Figure 8:
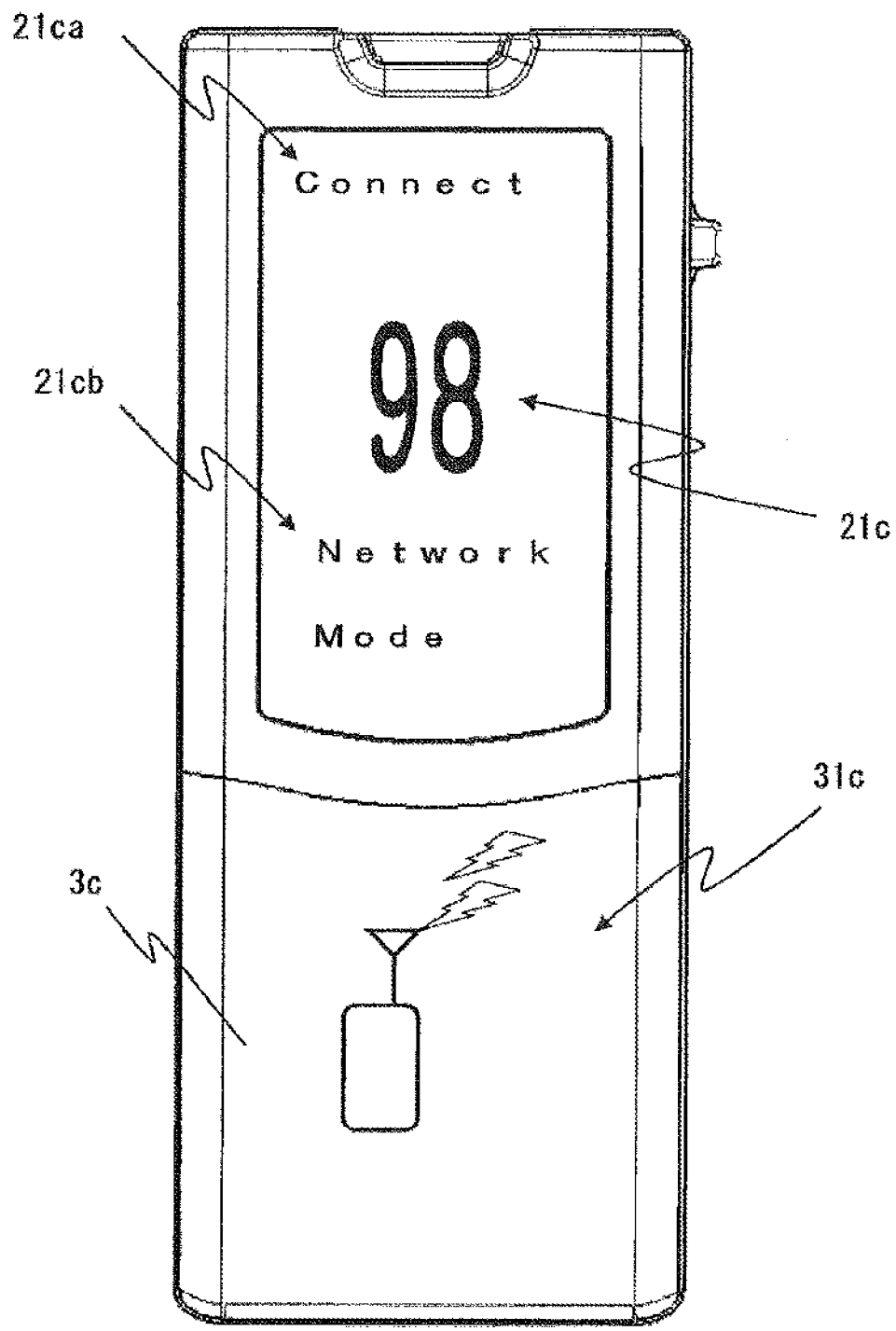
FIG. 8 is a front view of a blood sugar level measuring apparatus according to Panel Example 3 of Embodiment 1.

FIG. 8 shows a state where panel 3 of FIG. 1 is panel 3c. Specifically, panel 3c transmits the measurement data stored in data storage section 14 to the outside of the apparatus (that is, to a different apparatus) through communication section 15. As shown in FIG. 8, function display section 31c is provided on the surface of panel 3c, the section 31c causing a user to recognize that the measurement data stored in data storage section 14 is transmitted to the different apparatus. Further, the control information is stored in the RF-ID tag (not shown in the drawing) which is provided on the rear side of panel 3c, the control information corresponding to the control program issuing the command to transmit the measurement data stored in data storage section 14 to the different apparatus through communication section 15.

If panel 3c is mounted on apparatus main body 1, it is determined that panel 3 is panel 3c in step S103 or step S107 of FIG. 5. Then, in a similar manner to the process of FIG. 5, the control information of the RF-ID tag provided on panel 3c is received by RF-ID reading antenna 8, and the control information is read by reader/writer 16. Control section 11 reads and executes the control program, corresponding to the control information from program memory 12, in response to the command issued from control program instruction section 13. As a result, measurement data 21c is displayed on main body display section 2. Further, caution message 21ca (here, "Connect") that communication is established is displayed on top of measurement data 21c, and caution message 21cb (here, "Network Mode") that the current mode is a network mode is displayed below measurement data 21c.

Here, by using communication section 15 (refer to FIG. 4) built in apparatus main body 1, the data measured by blood sugar level measuring apparatus 100 and the like are transmitted to the different apparatus. However, as another embodiment, a communication section may be mounted on panel 3c, the communication section being able to communicate with other devices. In this case, it is not necessary to provide communication section 15 in apparatus main body 1.

Further, it is advantageous that the communication section has a wireless communication system of communication for a mobile phone, wireless LAN, Bluetooth (registered trademark), or the like. By using the communication function, it is possible to directly or indirectly transmit the measurement data to other devices. For example, when the blood sugar level data is transmitted to other devices such as drug injection apparatus through the communication section, it is possible to easily and appropriately inject a drug such as insulin within a drug syringes.

Furthermore, the efficiency of administration of the measurement data is improved, whereby it is possible to promptly and precisely update the measurement data. As a result, even in clinical diseases such as a chronic disease, the latest data can be used, and thus medical treatment can be more appropriately performed.

1.4.4 Panel Example 4

Figure 9:
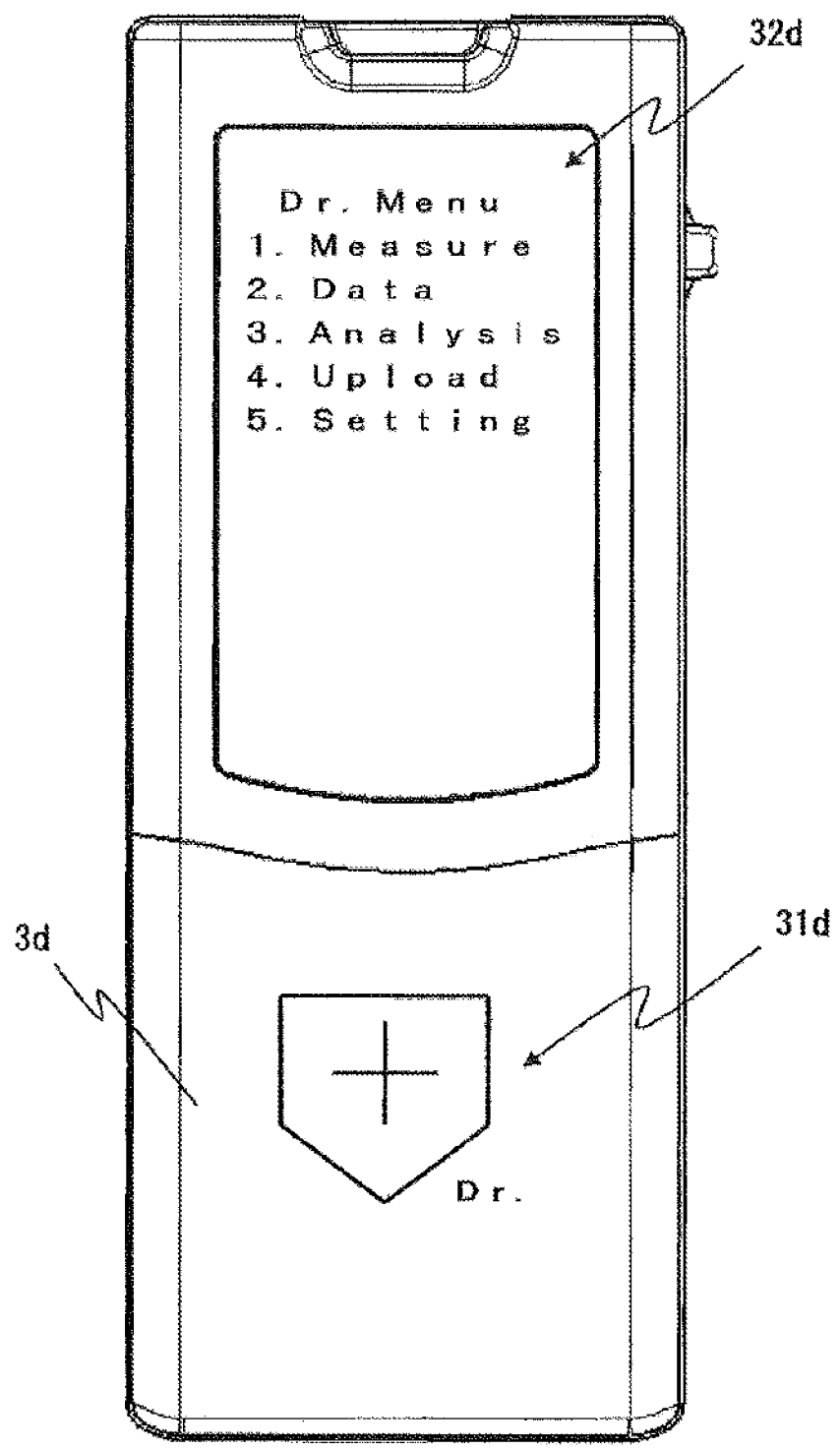
FIG. 9 is a front view of a blood sugar level measuring apparatus according to Panel Example 4 of Embodiment 1.

FIG. 9 shows a state where panel 3 of FIG. 1 is panel 3d. Specifically, panel 3d is available when a medical staff uses blood sugar level measuring apparatus 100. The medical staff detaches mounted front panel 3 from apparatus main body 1, and then panel 3d is mounted thereon. As shown in FIG. 9, function display section 31d is provided on the surface of panel 3d, the section 31d causing a user to recognize that panel 3d is for a medical staff. Further, the control information is stored in the RF-ID tag (not shown in the drawing) which is provided on the rear side of panel 3d, the control information corresponding to the control program issuing the command to execute the process through which the medical staff uses the apparatus.

Figure 10:
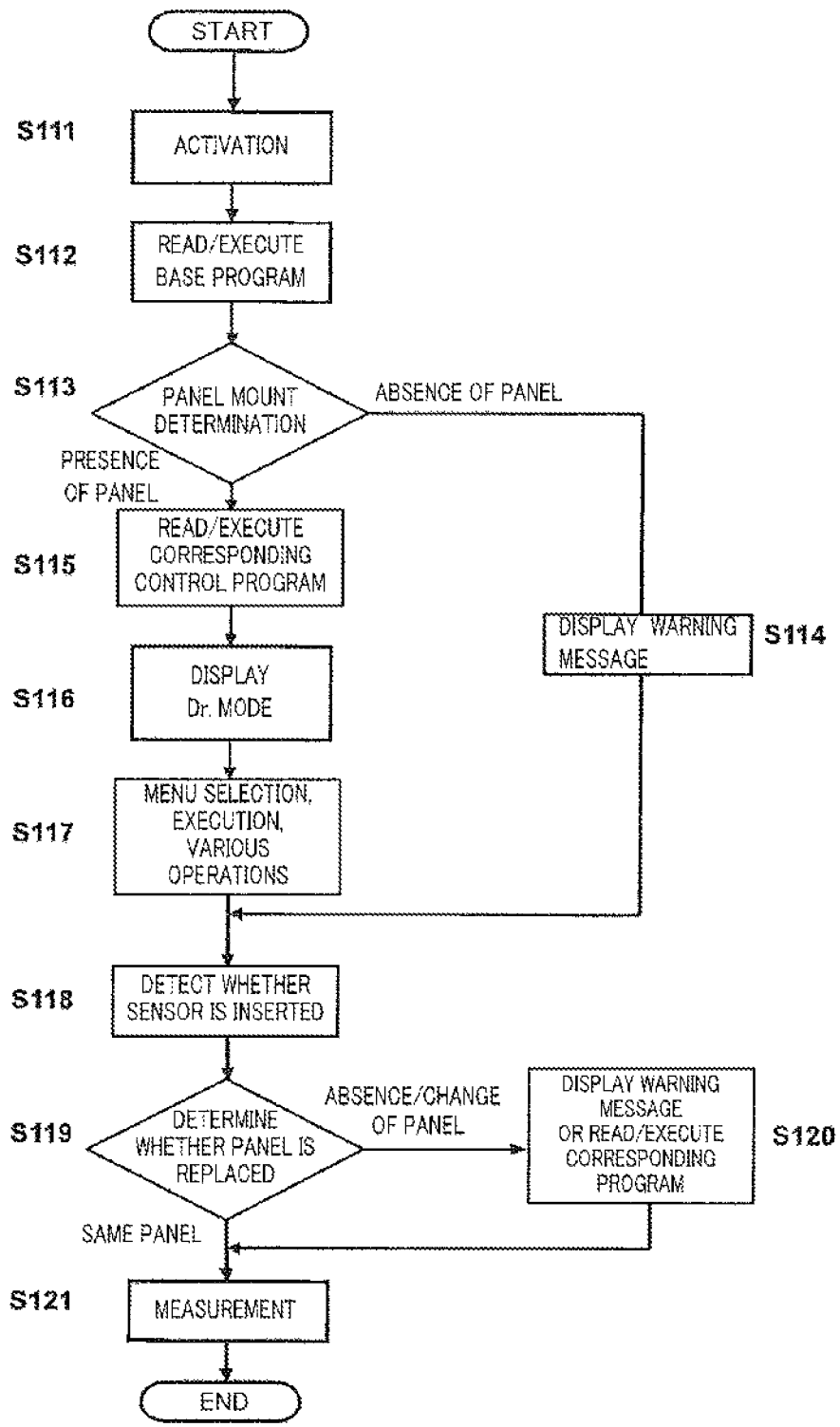
FIG. 10 is a flowchart illustrating a process performed by the control unit of the blood sugar level measuring apparatus according to Panel Example 4 of Embodiment 1.

FIG. 10 is a flowchart illustrating the process in the case where panel 3d as panel 3 is mounted on apparatus main body 1.

Step S111: in a similar manner to step S101 of FIG. 5, when a user operates operational section 5, the power supply is ON so as to activate the respective sections of the apparatus.

Step S112: in a similar manner to step S102 of FIG. 5, control section 11 of control unit 10 reads and executes a base program from program memory 12.

Step S113: in a similar manner to step S103 of FIG. 5, control section 11 determines whether or not panel 3 is mounted on apparatus main body 1, after the power supply is ON. The panel mount determination is performed by determining whether the control information is received from RF-ID tag 7 of panel 3 in which the electric power is generated by the radio waves intermittently transmitted by RF-ID reading antenna 8. Control section 11 determines that panel is not mounted if there is no command issued from control program instruction section 13 as described above, and then advances the process to step S114. In contrast, control section 11 advances the process to step S115 if there is the command issued from control program instruction section 13 as described above.

Step S114: in a similar manner to step S104 of FIG. 5, control section 11 causes main body display section 2 to display information for warning that panel 3 is not mounted on apparatus main body 1, and the process advances to step S118. In addition, as will be described later, the blood sugar level can be measured by blood sugar level measuring section 9 even when the warning is displayed in step S114.

Step S115: in a similar manner to step S105 of FIG. 5, control section 11 performs the following process when control section 11 determines that panel 3 (in the present process, panel 3d) is mounted on apparatus main body 1, that is, when the control information received by RF-ID reading antenna 8 can be transferred to control program instruction section 13 through reader/writer 16. Control section 11 reads and executes the control program among a plurality of control programs in program memory 12 in response to the command issued from control program instruction section 13, the control program corresponding to the control information which is read from current RF-ID tag 7.

Step S116: control section 11 causes main body display section 2 to display menu 32d (here, 1. Measure, 2. Data, 3. Analysis, 4. Upload, 5. Setting) which is a display (Dr. mode) for the medical staff.

The menu item "1. Measure" is an item for executing a function of measuring the blood sugar level of the adhered blood drop by inserting blood sugar level sensor chip SC into blood sugar level measuring section 9. The measured blood sugar level is thereafter displayed on main body display section 2. The menu item "2. Data" is an item for executing a function of sequentially displaying the measurement data pieces on main body display section 2, the measurement data being stored in data storage section 14. The menu item "3. Analysis" is an item for executing a function of analyzing the measurement data pieces which are stored in data storage section 14, and thereafter displaying the analyzing data on main body display section 2. The menu "4. Upload" is an item for executing a function of transferring the measurement data pieces stored in data storage section 14 to a computer through an interface such as USB, the computer belonging to the medical staff or the like. The menu item "5. Setting" is an item for executing a function of changing the owner data, the setting data and the like of apparatus main body 1 for the medical staff.

Step S117: the medical staff selects any one of the menu items (in the example of FIG. 9, five items) displayed on main body display section 2 by operating operational section 5, and thereby executes an interactive operation. In response to the selection, control section 11 executes the function corresponding to the selected item.

Step S118: in a similar manner to step S106 of FIG. 5, when blood sugar level sensor chip SC is inserted into sensor insertion opening 4, blood sugar level measuring section 9 detects the insertion of the sensor chip.

Step S119: in a similar manner to step S107 of FIG. 5, control section 11 receives the information that blood sugar level sensor chip SC is mounted, and determines whether or not panel 3 is mounted on apparatus main body 1, and whether panel 3 is changed after the previous panel mount determination. The determination as to whether panel 3 is mounted is performed by determining whether the control information is received from RF-ID tag 7 of panel 3 in which the electric power is generated by the radio waves intermittently transmitted by RF-ID reading antenna 8 and by determining whether the received control information is the same as that at the previous panel mount determination.

Step S120: in a similar manner to step S108 of FIG. 5, control section 11 causes main body display section 2 to display a warning that the panel is not mounted if panel 3 is not mounted on apparatus main body 1. Further, when panel 3 is changed with a different panel, control section 11 reads and execute the control program from program memory 12, the control program corresponding to the control information received from RF-ID tag 7 of panel 3. And control section 11 causes main body display section 2 to display a warning that the executed control program is changed.

Step S121: in a similar manner to step S109 of FIG. 5, the blood sugar level is measured by blood sugar level measuring section 9. In addition, when blood sugar level sensor chip SC is inserted into blood sugar level measuring section 9 in a state where panel is not mounted on apparatus main body 1, the measured blood sugar level data is configured not be stored in data storage section 14 even if the blood sugar level is measured.

1.5 Characteristics of Embodiment 1

As can be understood from the above description, in blood sugar level measuring apparatus 100 according to the present embodiment, panel 3 having RF-ID tag 7 is mounted on apparatus main body 1, and the control information stored in memory 71 of RF-ID tag 7 is sent from antenna 72 to RI-ID reading antenna 8 provided in apparatus main body 1 through radio waves. Then, on the basis of the control information of RF-ID tag 7 received by RF-ID reading antenna 8, control program instruction section 13 issues a command to control section 11. And then control section 11 reads and executes the control program corresponding to the control information among the plurality of control programs stored in program memory 12. Thereby, a user is able to cause blood sugar level measuring apparatus 100 to execute a desired function only by replacing panel 3 without performing troublesome operations.

Further, in the present embodiment, function display sections 31a to 31d are provided on the surfaces of panels 3a to 3d to be mounted on apparatus main body 1, and thus RF-ID tags 7 are provided on panel 3a to 3d. Hence, a user is able to easily know how the function is being executed by checking the contents of function display sections 31a to 31d of the panel.

Further, RF-ID reading antenna 8 provided on apparatus main body 1 reads the contents of RF-ID tag 7 of panel 3, whereby it is possible to reliably change the control program. And further it is possible to change the functions corresponding to the function display sections 31a to 31d provided on panel 3a to 3d. Hence, a user is able to easily and reliably operate blood sugar level measuring apparatus 100.

1.6 Modified Example of Embodiment 1

Figure 11:
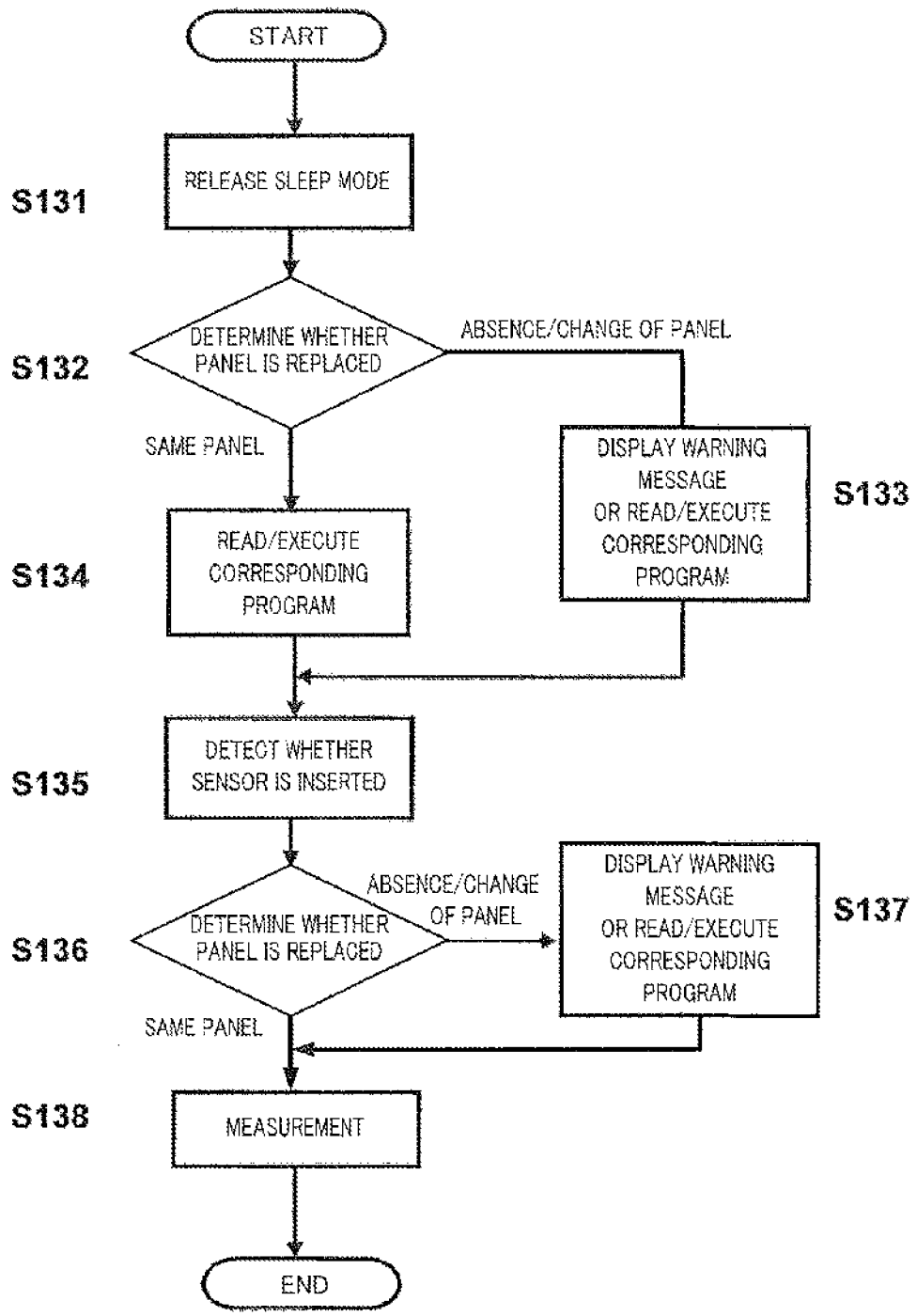
FIG. 11 is a flowchart illustrating a process performed by a control unit of a blood sugar level measuring apparatus according to a modified example of Embodiment 1.

FIG. 11 is a flowchart illustrating a process in a case where a sleep mode is set in the blood sugar level measuring apparatus 100 according to Embodiment 1. Blood sugar level measuring apparatus 100 is automatically or manually set in a sleep mode, that is, a standby state (energy saving mode) if there is no operation performed by a user during a predetermined time.

The processes of FIGS. 5 and 10 describe examples in which blood sugar level measuring apparatus 100 is activated when operational section 5 is operated. However, the present modified example describes an operation subsequent to reactivation (cancellation of the sleep mode) after the sleep operation. Specifically, the operation is as follows.

Step S131: when a user operates operational section 5, the sleep mode of blood sugar level measuring apparatus 100 is released.

Step S132: control section 11 receives the information that the sleep mode is cancelled, and determines whether or not panel 3 is mounted on apparatus main body 1, and whether panel 3 is changed after the previous panel mount determination. The determination as to whether panel 3 is mounted is performed by determining whether the control information is received from RF-ID tag 7 of panel 3 in which the electric power is generated by the radio waves intermittently transmitted by RF-ID reading antenna 8.

Step S133: control section 11 causes main body display section 2 to display a warning that the panel is not mounted if panel 3 is not mounted on apparatus main body 1. Further, when panel 3 is changed with a different panel, control section 11 reads out and executes the control program from program memory 12, the control program corresponding to the control information received from RF-ID tag 7 of panel 3. And also, control section t1 causes main body display section 2 to display a warning that the executed control program is changed. The selective reading of the control program from program memory 12 by control section 11 is performed by control program instruction section 13 as described above.

Step S134: in contrast, if control section 11 determines that panel 3 is not changed, that is, if the control information received by RF-ID reading antenna 8 is the same as the control information which is received after the previous panel mount determination, control section 11 reads and executes the control program among the plurality of control programs in program memory 12 in response to the command issued from control program instruction section 13. The control program corresponds to the control information which is read from current RF-ID tag 7, and is the same as that at the previous time.

Step S135: in a similar manner to step S106 of FIG. 5, when blood sugar level sensor chip SC is inserted into sensor insertion opening 4, blood sugar level measuring section 9 detects the insertion of the sensor chip.

Step S136: in a similar manner to step S107 of FIG. 5, control section 11 receives the information that blood sugar level sensor chip SC is mounted, and determines whether or not panel 3 is mounted on apparatus main body 1, and whether panel 3 is changed after the previous panel mount determination. The determination as to whether panel 3 is mounted is performed by determining whether the control information is received from RI-ID tag 7 of panel 3 in which the electric power is generated by the radio waves intermittently transmitted by RF-ID reading antenna 8 and by determining whether the received control information is the same as that at the previous panel mount determination.

Step S137: in a similar manner to step S108 of FIG. 5, control section 11 causes main body display section 2 to display a warning that the panel is not mounted if panel 3 is not mounted on apparatus main body 1. Further, when panel 3 is changed with a different panel, control section 11 reads and executes the control program from program memory 12, the control program corresponding to the control information received from RF-ID tag 7 of panel 3. And also, control section 11 causes main body display section 2 to display a warning that the executed control program is changed.

Step S138: in a similar manner to step S109 of FIG. 5, the blood sugar level is measured by blood sugar level measuring section 9. In addition, when blood sugar level sensor chip SC is inserted into blood sugar level measuring section 9 in a state where panel 3 is not mounted on apparatus main body 1, the measured blood sugar level data is set not to be stored in data storage section 14 even if the blood sugar level is measured It should be noted that the contents of the process is just an example, and the procedure thereof is not limited to the above description. For example, in order to suppress the consumption of the battery in the above process, the determination of panel 3 is performed when the power supply is applied and when blood sugar level sensor chip SC is mounted. However, the determination of the panel mount/change may be performed whenever the panel is changed or separated. In such a manner, blood sugar level measuring apparatus 100 of the present modified example can be set in sleep mode so as not to perform the communication between RF-ID tag 7 and RF-ID reading antenna 8 in the sleep mode. Thus, it is possible to suppress the battery consumption.

Further, for example, a method of activating the apparatus when panel 3 is mounted may be adopted. Specifically, when it is detected that panel 3 is mounted on apparatus main body 1, the sleep mode of apparatus main body 1 is cancelled, and the main power supply is turned ON. In this case, the apparatus main body 1 detects that panel 3 is mounted, and the above-mentioned processes of steps S131 to S135 are executed. In such a manner, it is not necessary to display the warning that panel 3 is not mounted.

2. Embodiment 2

In a similar manner to Embodiment 1, blood sugar level measuring apparatus (biological information measuring apparatus) 200 of Embodiment 2 includes a panel that has an RF-ID tag, and an apparatus main body that has an RF-ID reading antenna capable of receiving the control information from the RF-ID tag when the panel is mounted on the apparatus main body. And thereby, an operation for an emergency response case can be performed. According to the present embodiment, a user detaches the panel from the apparatus main body, whereby an emergency response signal can be transmitted.

2.1 Configuration of Blood Sugar Level Measuring Apparatus

The configurations of the apparatus main body and the panel in blood sugar level measuring apparatus 200 according to Embodiment 2 are the same as the configurations of FIGS. 1 to 3. Accordingly, in the following description, the sections having the same configurations and functions will be represented by the same reference numerals and signs.

2.2 Control Unit

Figure 12:
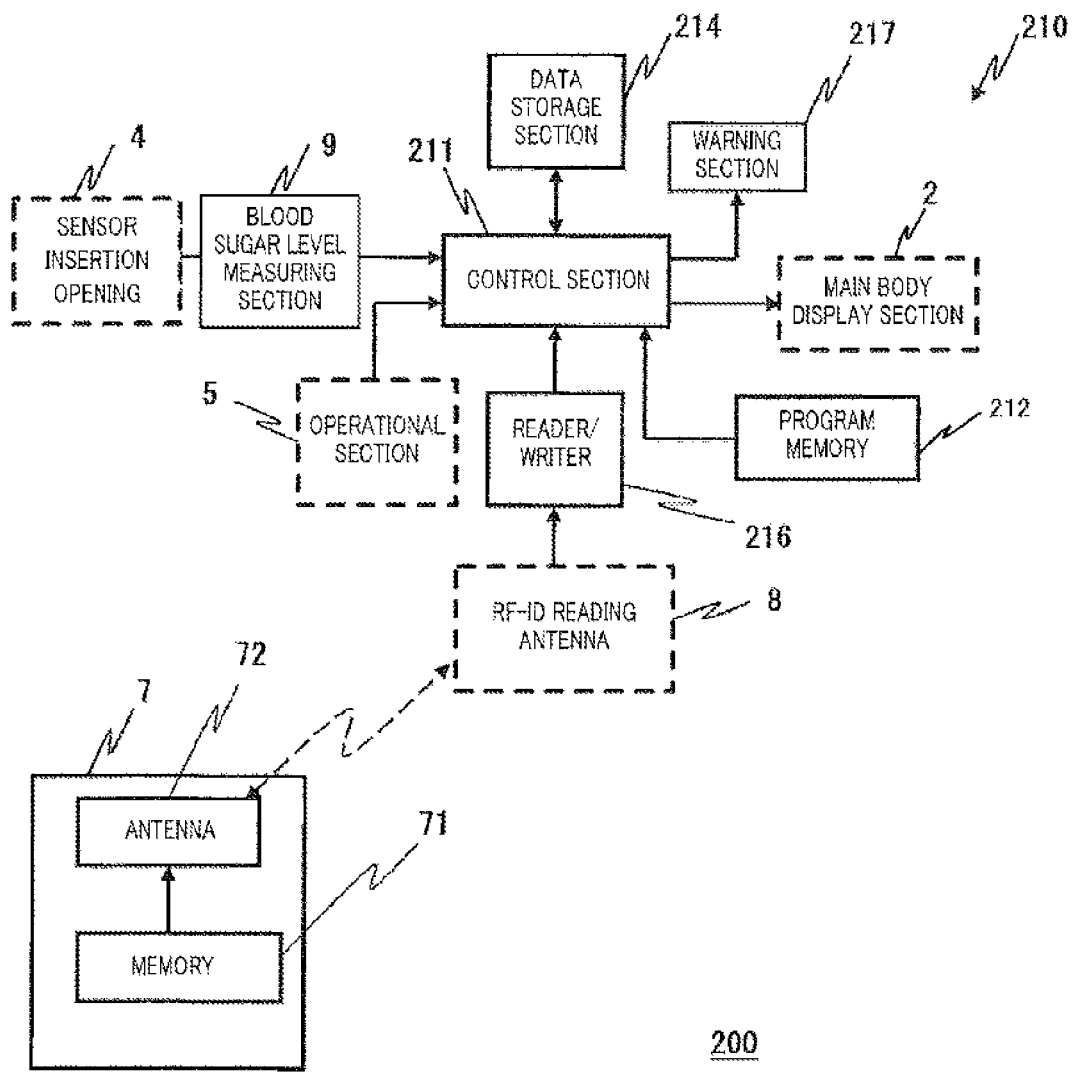
FIG. 12 is a configuration diagram of a control unit of a blood sugar level measuring apparatus according to Embodiment 2.

FIG. 12 shows a configuration of control unit 210 provided inside apparatus main body 1 of blood sugar level measuring apparatus 200. As shown in FIG. 12, control unit 210 includes control section 211, program memory 212, data storage section 214, reader/writer 216, and alarm section 217.

Control section 211 is connected to main body display section 2 of apparatus main body 1, operational section 5, and blood sugar level measuring section 9. Control section 211 commands main body display section 2 to display information. Control section 211 generates a control command corresponding to the signal from operational section 5 operated by a user, and transmits the command to the respective sections.

Blood sugar level measuring section 9 connected to control section 211 measures the blood sugar level of the blood drop in a similar manner to Embodiment 1, the blood drop being adhered onto blood sugar level sensor chip SC inserted through sensor insertion opening 4.

Program memory 212 stores a plurality of control programs which can be read by control section 211 in order to execute functions of the apparatus, in a similar manner to Embodiment 1.

As described above, data storage section 214 stores the measured blood sugar level data in response to the command issued from control section 211, in a similar manner to Embodiment 1.

Reader/writer 216 reads control information which is received by RF-ID reading antenna 8. Alarm section 217 sounds an alarm such as a buzzer sound in response to the command of control section 211.

As shown in FIG. 12, in a similar manner to Embodiment 1, RF-ID tag 7 mounted on panel 3 has memory 71 and antenna 72 connected to memory 71. Memory 71 stores the control information corresponding to panel 3 onto which RF-ID tag 7 is fixedly attached. In a state where RF-ID tag 7 and RF-ID reading antenna 8 of apparatus main body 1 are able to communicate (that is, a state where panel 3 is mounted on apparatus main body 1), RF-ID reading antenna 8 receives the control information from RF-ID rag 7, and the information is read by reader/writer 216 of apparatus main body 1. Control section 211 commands control section 211 to execute the corresponding control program from program memory 212 in response to the control information which is read by reader/writer 216.

It should be noted that, although battery 61 is not shown in FIG. 12, all the parts provided on control section 211, that is, provided in apparatus main body 1, uses battery 61 as a power supply. When an electric power is supplied from battery 61, radio waves are intermittently transmitted from RF-ID reading antenna 8. Antenna 72 of RF-ID tag 7 receives the radio waves so as to obtain electromotive force by smoothing and rectifying the received radio waves. Thereby, the control information recorded in memory 71 is sent from antenna 72 to RF-ID reading antenna 8 by the radio waves. In addition, here, a disposable button battery (refer to FIG. 2) is used as battery 61, but the battery is not limited to this, and may be a chargeable battery such as an alkali battery or a Li-ion battery.

2.3 Operation of Blood Sugar Level Measuring Apparatus

Figure 13:
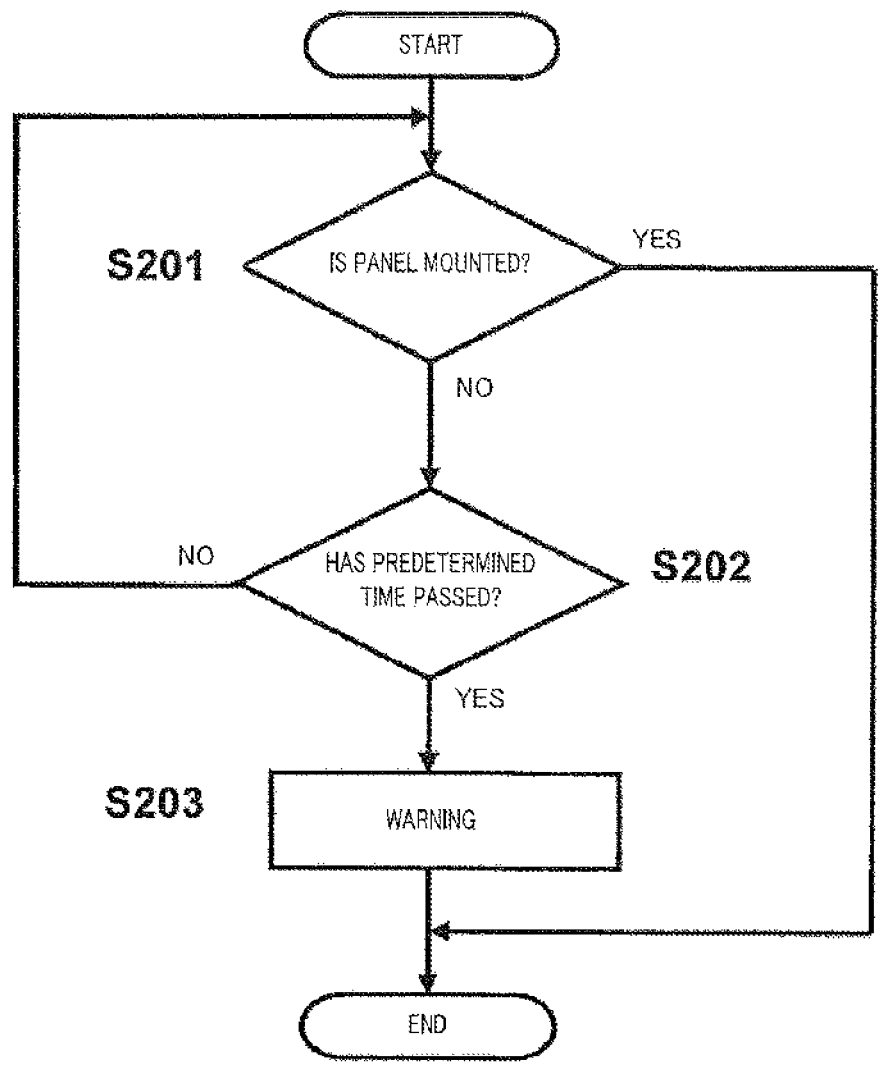
FIG. 13 is a flowchart illustrating a process performed by the control unit of the blood sugar level measuring apparatus according to Embodiment 2.

FIG. 13 is a flowchart illustrating a process of control unit 210 of blood sugar level measuring apparatus 200 according to the present embodiment. In the present embodiment, in a similar manner to Embodiment 1 mentioned above, as shown in FIG. 1, when antenna 72 of RF-ID tag 7 provided on panel 3 and RF-ID reading antenna 8 of apparatus main body 1 face each other (that is, when the apparatus begins to be used in a normal state), control section 211 detects the communication between antenna 72 of RF-ID tag 7 and RF-ID reading antenna 8 of apparatus main body 1. In contrast, as shown in FIG. 2, when panel 3 is separated from apparatus main body 1, antenna 72 of RF-ID tag 7 does not face RF-ID reading antenna 8 of apparatus main body 1. Accordingly, control section 211 detects that there is no communication between antenna 72 of RF-ID tag 7 and RF-ID reading antenna 8 of apparatus main body 1. Specifically, the operation is as follows.

Step S201: control section 211 determines whether or not panel 3 is mounted on apparatus main body 1. In a similar manner to Embodiment 1, the determination as to whether panel 3 is mounted is performed by determining whether the control information is received from RF-ID tag 7 of panel 3 in which the electric power is generated by the radio waves intermittently transmitted by RF-ID reading antenna 8.

Step S202: if panel 3 is not mounted, control section 211 determines whether a predetermined time has passed from the time of determination of step S201. If the predetermined time does not pass, the process returns to step 201, and it is checked again whether or not panel 3 is mounted. In contrast, if the predetermined time has passed, the process advances to next step 203.

Here, the reason why it is determined whether a predetermined time has passed is as follows. Panel 3 may be detached from apparatus main body 1 as shown in FIG. 2 not only in a situation where a user detaches the panel in order to respond to an emergency but also in situations where the panel is simply replaced or battery 61 is replaced. Accordingly, it is necessary to determine whether the detachment is for normal procedure or is for emergency response. Hence, control section 211 counts the time from the time of the determination of step S201, and determines whether the predetermined time or more (for example 3 minutes, where the time can be optionally set) passes, thereby determining whether panel 3 is continuously separated. If the predetermined time (for example, 3 minutes) or more passes, the process advances to step S203.

Step S203: control section 211 causes alarm section 217 to sound an alarm. It should be noted that, at this time, main body display section 2 may display a warning in response to the command of control section 211.

It should be noted that the process may be performed in parallel with the process of Embodiment 1. Further, the determination process of step S201 may be performed at a predetermined time interval, and may be performed in accordance with the panel mount determination shown in FIGS. 5, 10, and 11 of Embodiment 1.

Further, even when the period of time during which battery 61 is separated is long, the emergency response operation is not erroneously performed by blood sugar level measuring apparatus 200 according to Embodiment 2. Specifically, current is not applied if battery 61 is separated within the predetermined time after panel 3 is detached and antenna 72 and RF-ID reading antenna 8 do not face each other. Then, the power is not supplied to the respective functional blocks including control section 211, and thus the operation is stopped. Hence, even though the predetermined time has passed, notification of the emergency response is not performed. Thereafter, when battery 61 is housed again in battery housing section 6 so as to apply current, the apparatus begins to be used in a first normal state, and control section 211 performs the normal process. That is, even when the period of time during which battery 61 is detached is too long, the notification of the emergency response is not performed, and battery 61 can be replaced.

In addition, battery 61 is not housed in battery housing section 6 at a normal shipment of the apparatus. And battery 61 is separately shipped and sold. Alternatively, when the apparatus is shipped in a state where battery 61 is housed in battery housing section 6, a film is interposed at contact point between battery housing section 6 and battery 61 so as not to consume a power of battery. That is, while the time of shipment, power is not supplied to the respective functional blocks including control section 211. Accordingly, as described above, it is not determined whether or not antenna 72 and RF-ID reading antenna 8 face each other, and the apparatus is not used. Thereafter, battery 61 is housed in battery housing section 6 so as to apply current to the apparatus. And then, it is determined whether or not antenna 72 and RF-ID reading antenna 8 face each other when panel 3 is mounted on apparatus main body 1 for the first time, and the apparatus begins to be used (apparatus activation) as shown in FIGS. 5, 10, and 11 if the antenna face each other.

2.4 Characteristics of Embodiment 2

In blood sugar level measuring apparatus 200 according to the present embodiment, contrary to the conventional operation performed with the operational buttons, a user performs the simple and easy operation of detaching panel 3, whereby the emergency response signal can be transmitted. Thereby, the user is unlikely to perform an error operation, and thus appropriate and reliable emergency response is possible.

2.5 Modified Example of Embodiment 2

2.5.1 Modified Example 1

Figure 14:
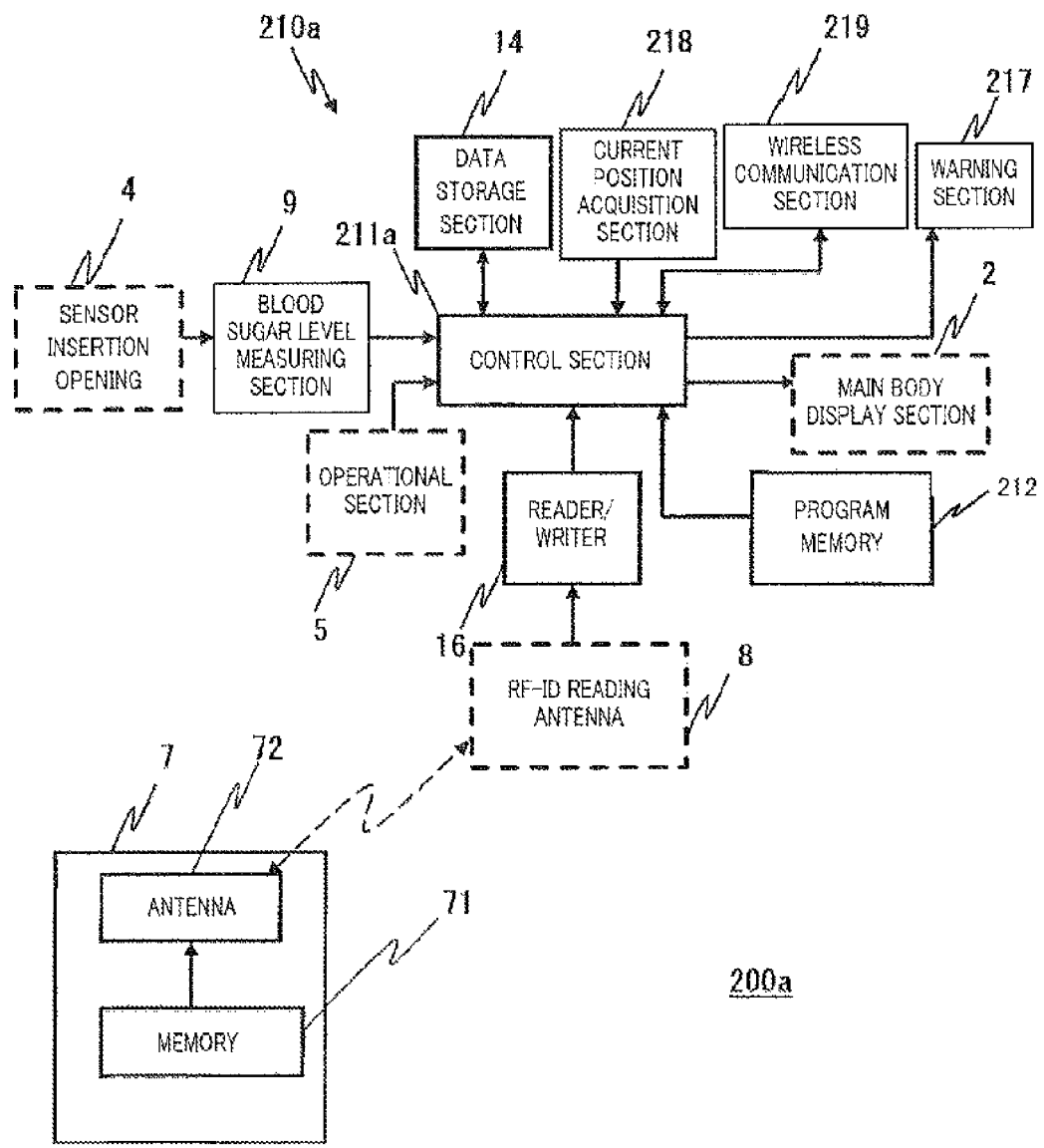
FIG. 14 is a configuration diagram of a control unit of a blood sugar level measuring apparatus according to a modified example of Embodiment 2.

FIG. 14 shows a control block diagram of blood sugar level measuring apparatus 200a according to Modified Example 1 of Embodiment 2 of the present invention. As shown in FIG. 14, blood sugar level measuring apparatus 200a according to Modified Example 1 includes not only control unit 210 of blood sugar level measuring apparatus 200 of Embodiment 2 mentioned above but also current position acquisition section 218 and wireless communication section 219. It should be noted that the same configurations and functions as Embodiment 2 will be represented by the same reference numerals and signs and a description thereof will be omitted.

Current position acquisition section 218 acquires the current position of the main body of blood sugar level measuring apparatus 200a in response to the command issued from control section 211a. For example, current position acquisition section 218 is an existing GPS (Global Positioning System) unit. Radio waves transmitted from an artificial satellite are received by current position acquisition section 218, whereby the current position of blood sugar level measuring apparatus 200a is specified. And then, the specified current position information is sent to control section 211a.

Wireless communication section 219 equipped with an antenna for communication communicates with the external communication network through a wireless communication. Wireless communication section 219 is connected to, for example, a base station of a telephone communication network like a mobile phone, or is connected to an access point of a wireless LAN on the Internet. Further, in the telephone communication network or the Internet, a server is disposed which communicates with blood sugar level measuring apparatus 200a. And the server processes the information which is sent from blood sugar level measuring apparatus 200a. The process of the server is set to be automatically operated by a program, or is performed by an operation of an operator such as a medical staff.

The operation of blood sugar level measuring apparatus 200a configured in such a manner will be described. In a similar manner to blood sugar level measuring apparatus 200 according to Embodiment 2 mentioned above, panel 3 is detached from apparatus main body 1, antenna 72 of RF-ID tag 7 and RF-ID) reading antenna 8 do not face each other, and a predetermined time or more passes (after step S202 of FIG. 13). Then, control section 211a commands current position acquisition section 218 to acquire current position, and commands wireless communication section 219 to performs connection with the external server.

After the acquisition of the current position information by current position acquisition section 218 and the connection with the external server by wireless communication section 219 are completed, control section 211a transmits the current position information to the external server through wireless communication section 219.

In such a manner, when a user is in a poor healthcare condition, the current position information of the user is transferred on the external server. The external server arranges an emergency vehicle or the like through the operation of the operator or the automatic program activated on the basis of the transferred current position information of the user. And therefore, the external server is able to cause the emergency vehicle or the like to precisely arrive at the place of the user.

In addition, at this time, each functional block other than current position acquisition section 218 and wireless communication section 219 sounds an alarm, like control unit 210 of Embodiment 2. And thereby the functional block may request a person in the vicinity thereof to perform an appropriate emergency response.

Consequently, according to the above-mentioned configuration, when the user is in the poor healthcare condition, the user is appropriately treated by the person in the vicinity of the user, whereby it can be expected that the user is promptly transported to a medical institution or the like.

Modified Example 2

Modified Example 1 adopts the configuration in which the current position of the user acquired by current position acquisition section 218 is sent to the external server by wireless communication section 219. A configuration in which current position acquisition section 218 is not provided may be adopted.

In this case, wireless communication section 219 transfers the latest measured blood sugar level and the information to the external server through the operation of operational section 5, the information indicating that the user is in the poor condition. The external server receives the information from wireless communication section 219 of blood sugar level measuring apparatus 200a. And then, external server generates corresponding instruction information to be transmitted to wireless communication section 219. When the instruction information is received by wireless communication section 219, control section 211a causes main body display section 2 or alarm section 217 to display a notification on the basis of the instruction information. At this time, the automatic program or the operator determines a treatment from the measurement data which is transmitted from blood sugar level measuring apparatus 200a. And then, the external server generates the instruction information therefor. In this way, it is possible to promptly perform an emergency response appropriate for the user's condition.

2.5.3 Modified Example 3

In blood sugar level measuring apparatus 200 mentioned above, when it is determined that panel 3 is not mounted and thereafter the condition of passage of the predetermined time is satisfied, control section 211 sounds the alarm. And also, control section 211 causes the main body display section to display the warning information. Alternatively control section 211 transmits the current position of the apparatus to the external server or receives the instruction information from the external server. However, the present embodiment is not limited to this. For example, when the determination that panel 3 is not mounted and that an abnormal value (for example, a value indicating a low to blood sugar level) of the measurement data are made, the above-mentioned operation may be performed. In addition, it may be further determined whether the predetermined time has passed.

3. Embodiment 3

In blood sugar level measuring apparatus (biological information measuring apparatus) 300 of Embodiment 3, the convenience of the apparatus is enhanced by replacing panel 3.

3.1 Configuration of Blood Sugar Level Measuring Apparatus

The configuration of blood sugar level measuring apparatus 300 according to Embodiment 3 is the same as that of Embodiment 1 shown in FIGS. 1 to 3 except that panel 3 is not used as a battery cover, and an independent battery cover 362 is mounted on apparatus main body 1.

3.1.1 Configuration of Apparatus Main Body

Figure 15:
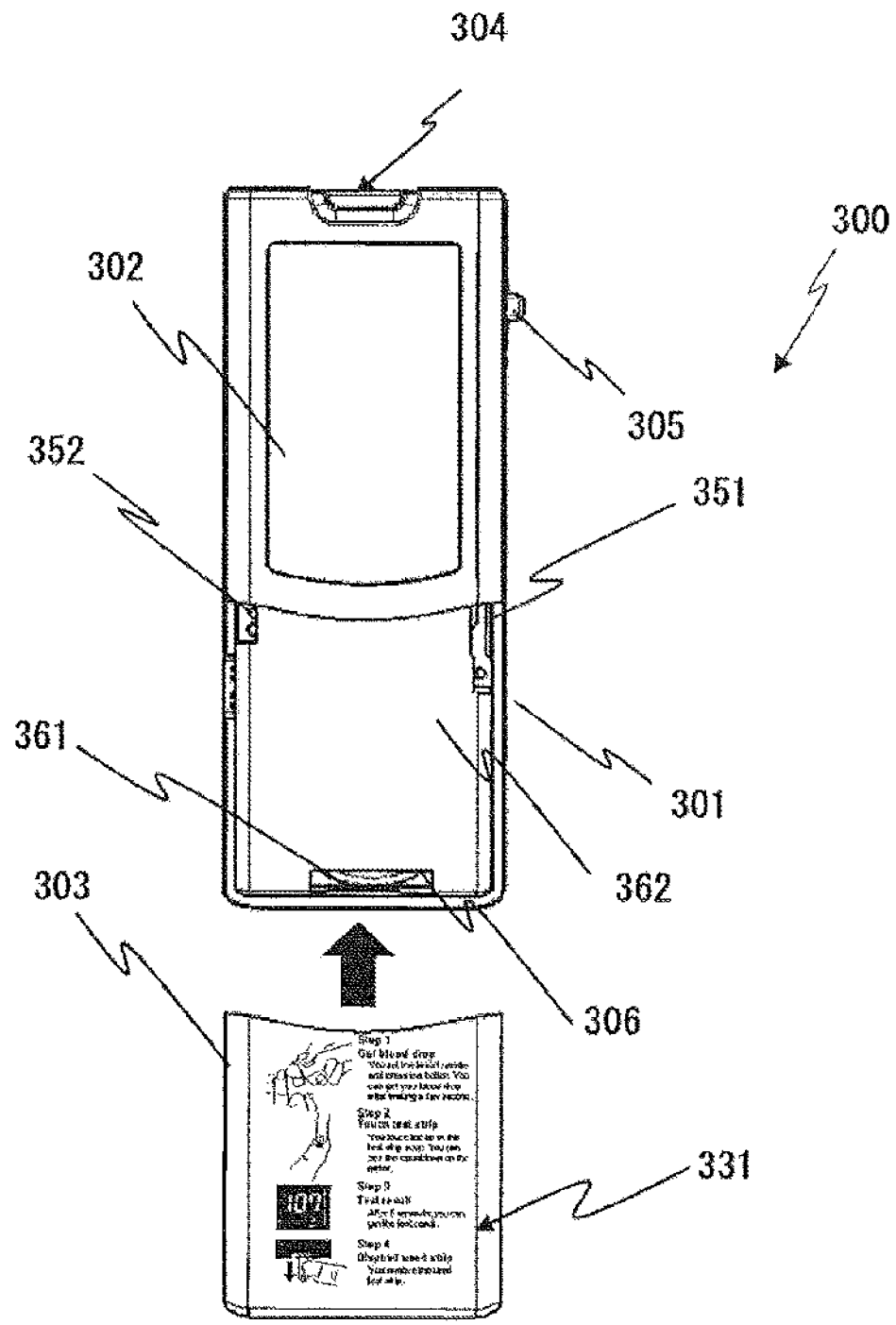
FIG. 15 is a front view illustrating a state in which a panel of a blood sugar level measuring apparatus according to Embodiment 3 is detached.

As shown in FIG. 15, apparatus main body 301 has a substantially rectangular shape. Apparatus main body 301 includes: main body display section 302 that is provided on the surface thereof; sensor insertion opening 304 that is provided on an upper side terminal thereof; operational section 305 that is provided a single side portion thereof; battery housing section 306; battery cover 362; and engagement sections 351 and 352 with which panel 303 is fixed onto apparatus main body 301.

Main body display section 302 is a display such as a liquid crystal display or an organic EL display. The display section 302 displays information such as the measured blood sugar level or a function menu to a user.

Sensor insertion opening 304 is an insertion opening of a sensor chip through which blood sugar level sensor chip is mounted on apparatus main body 301.

The operational section 305 includes a button, a switch a slide, a lever, a dial, and the like which a user handles with a finger to operate the apparatus.

The battery housing section 306 houses and is equipped with battery 361 as a power supply of blood sugar level measuring apparatus 300. Battery cover 362 is provided on the portion covered by panel 303 of apparatus main body 301, and covers battery 361 housed in battery housing section 306.

Engagement sections 351 and 352 have a mechanism for fixing panel 303 onto apparatus main body 301 in engagement with the portion corresponding to panel 303 when panel 303 is mounted on apparatus main body 301.

It should be noted that, in FIG. 15, battery cover 362 is mounted on the front side (side on which main body display section 302 is disposed) of apparatus main body 301, but the invention is not limited to this. For example, battery cover 362 may be provided on the rear side (the side opposite to display section 302) of apparatus main body 301. In this case, battery housing section 306 and battery 361 are also provided on the rear side (the side opposite to display section 302) thereof.

3.1.2 Configuration of Panel

Panel 303 is detachably mounted on apparatus main body 301, in a similar manner to Embodiment 1. Further, panel 303 has function display section 331 provided on the surface (the side the same as that of main body display section 302).

3.2 Example 3.2.1 Example 1

Figure 16:
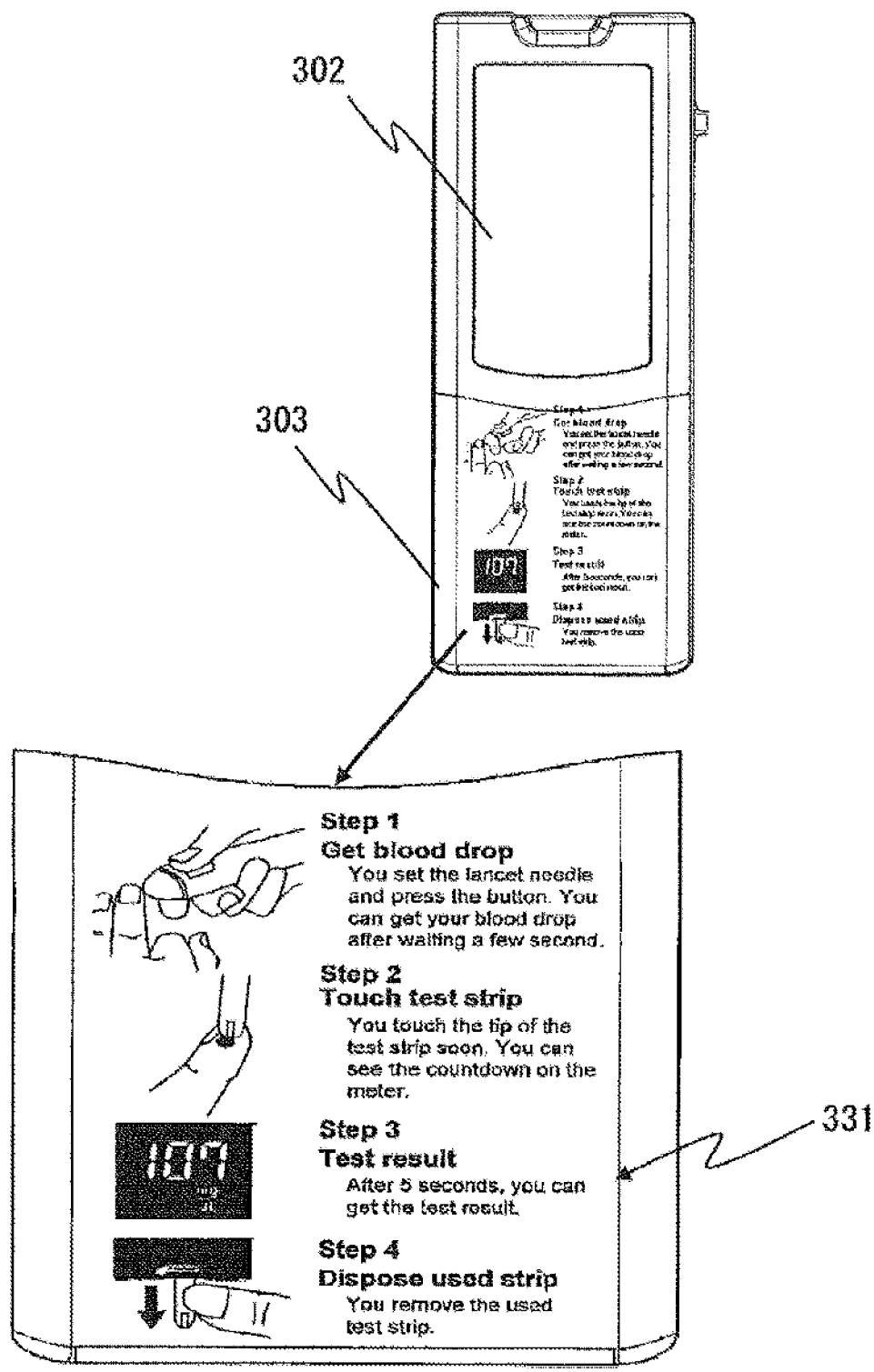
FIG. 16 is a partially enlarged front view illustrating a state in which the blood sugar level measuring apparatus according to Embodiment 3 is used.

In blood sugar level measuring apparatus 300 shown in FIGS. 15 and 16, an operation manual, a quick guide or the like of blood sugar level measuring apparatus 300 is printed on function display section 331 of panel 303.

As described above, by describing the operation manual, the quick guide or the like of blood sugar level measuring apparatus 300 on panel 303, it is not necessary for a user to carry the operation manual or the like. Further, a novice user is able to view the operation manual, the quick guide or the like while performing an operation. Furthermore, since panel 303 is detachable, it is possible to replace the panel with the multiple kinds of the panels (for example, a panel with colorful fashionability), when the user is familiar with the operation and it is not necessary for the user to view the operation manual or the like.

It should be noted that an operation manual, a quick guide or the like is not printed and is displayed formed by an electronic paper. When the electronic paper is used for function display section 331, connectors (not shown in the drawing) are provided on engagement sections 351 and 352 of apparatus main body 301. The power is supplied from apparatus main body 301 to the electronic paper as function display section 331 of panel 303 through the connectors. Further, in this case, it is possible to change the contents displayed on the electronic paper (function display section 331) by operating operational section 305 (a rotational dial shown in FIG. 15). As described above, when the electronic paper is used in function display section 331, it is possible to display multiple indications without replacing panel 303, and thus the convenience is improved.

3.2.2 Example 2

Figure 17:
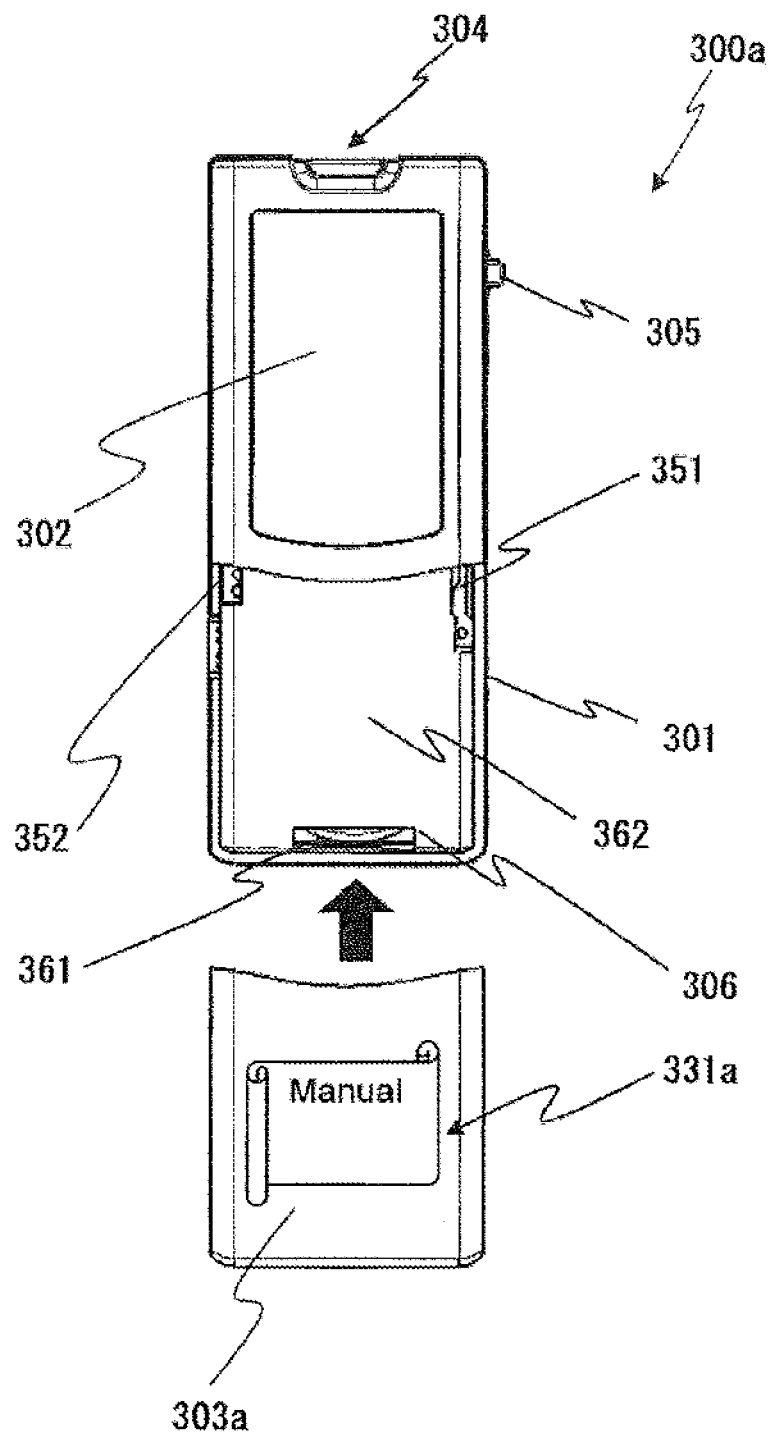
FIG. 17 is a front view illustrating a state in which a panel of a blood sugar level measuring apparatus according to Example 2 of Embodiment 3 is detached.
Figure 18:
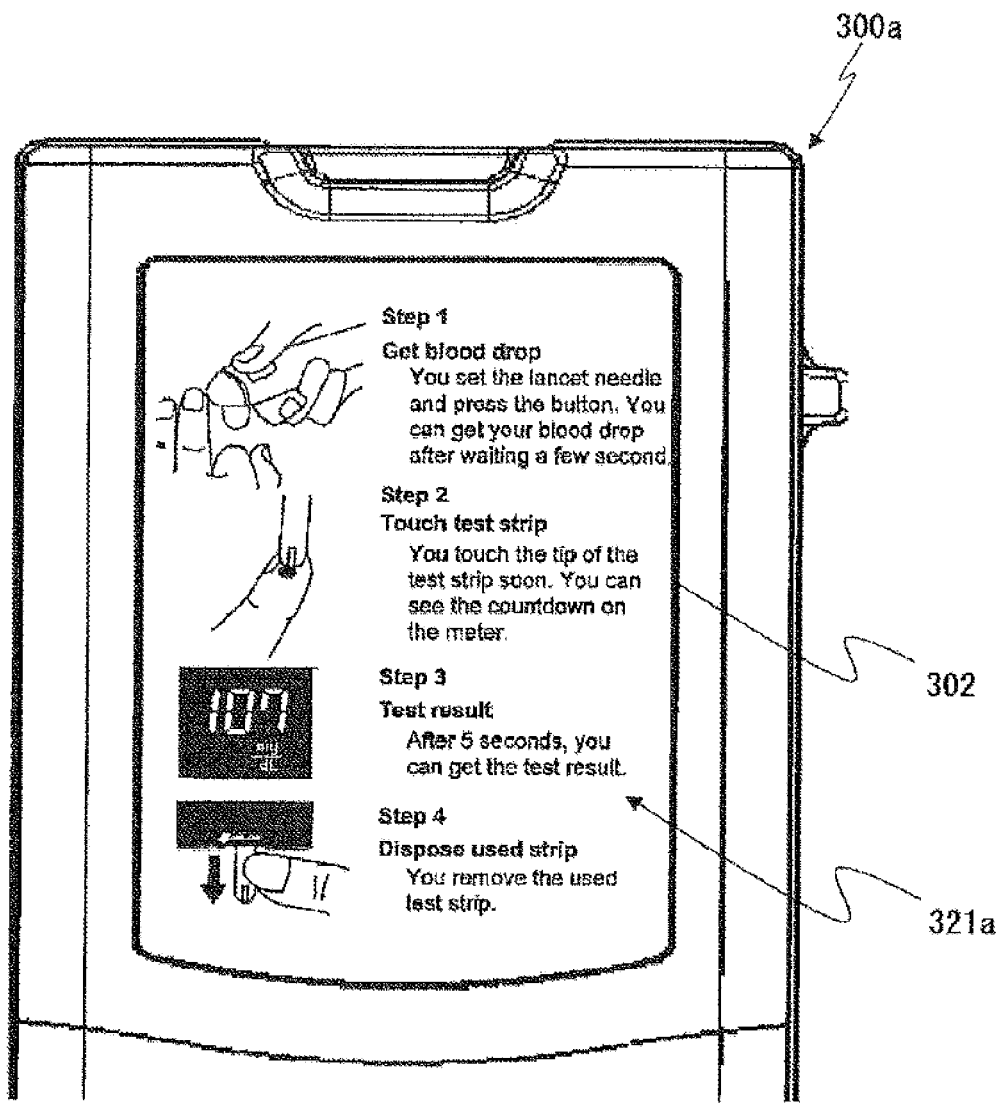
FIG. 18 is an enlarged view of a main body display section of the blood sugar level measuring apparatus according to Example 2.
Figure 19:
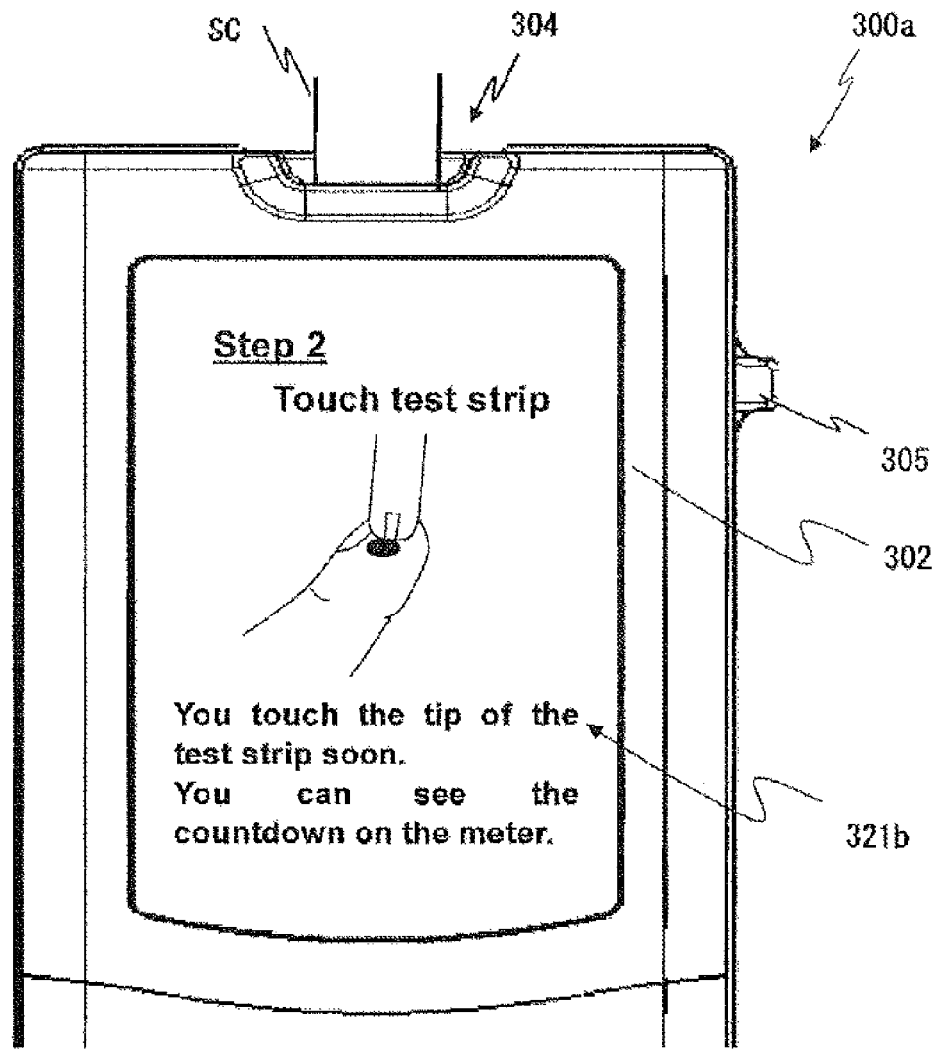
FIG. 19 is a separate enlarged view of the main body display section of the blood sugar level measuring apparatus according to Example 2.

In blood sugar level measuring apparatus 300a shown in FIGS. 17 to 19, panel 303a is mounted on apparatus main body 301, thereby displaying the contents of the operation manual on main body display section 302.

Blood sugar level measuring apparatus 300a has substantially the same configuration as blood sugar level measuring apparatus 300 mentioned above in Example 1. Blood sugar level measuring apparatus 300a operates as follows. In a similar manner to Embodiment 1, a control unit (not shown in the drawing, corresponding to control section 11 in FIG. 4) provided inside apparatus main body 301 detects that panel 303a is mounted on apparatus main body 301, activates the control program corresponding to panel 303a, and causes main body display section 302 to display the contents of the operation manual. Further, the information is displayed on function display section 331a of panel 303a, by the information the operation manual is recognized.

More specifically, when panel 303a is mounted on apparatus main body 301, the control information is received by the RF-ID reading antenna (corresponding to RF-ID reading antenna 8 in FIG. 4 or the like) of apparatus main body 301, the control information being stored in the memory (corresponding to memory 71 in FIG. 4 or the like) of the RF-ID tag (corresponding to RF-ID tag 7 in FIG. 4 or the like) mounted on panel 303a. Then, the control program corresponding to the control information received by the control unit is read. And then, an operation manual display data (characters, figures, photos, and the like) stored in the memory in advance is displayed on main body display section 2 by the control program.

It should be noted that, instead of this, the memory (for example, SD memory) mounted on panel 303a may store the operation manual display data (predetermined information). In this case, when panel 303a is mounted, the memory of panel 303a and apparatus main body 301 are electrically connected (not shown in the drawing) through the connectors (first and second communication units), the control unit (corresponding to control unit 10 in FIG. 4) of apparatus main body 301 may read the operation manual display data (predetermined information) upon connection. And then the control unit may cause main body display section 302 to perform display. In addition, the connectors may be respectively provided, for example, on the portions corresponding to panel 303 and engagement section 352 provided on apparatus main body 301. The operation manual display data or the control information within the SD memory mounted in panel 303a may be directly read by apparatus main body 301 so as to display the corresponding data or information on main body display section 302.

In the display method of main body display section 302, the overall flow of the usage method may be displayed (display example 321a), for example, as shown in FIG. 18. Each operation step thereof may be displayed in accordance with the progress of the actual measurement performed by apparatus main body 301, as shown in FIG. 19. In this case, when Step 2 as a process of the actual measurement is completed, Step 3 is displayed so as to facilitate a user to advance to the next process operation. Display example 321b of FIG. 19 facilitates a user to advance to the operation "the blood drop is adhered onto the sensor chip" in Step 2.

Further, the display may be performed in an enlarged manner or a reduced manner in accordance with operating operational section 305 by a user. For example, the user rotates the JOG dial/shuttle dial or the like with a user's finger for operating operational section 305.

As described above, according to the present example, since the user is able to perform the operation while viewing the operation manual, it is not necessary for the user to carry the operation manual or the like, and thus even a novice is able to reliably perform the operation without an error input. Further, since there is provided a function capable of changing the sizes of the characters and the figures of main body display section 302, it is easy even for a presbyope to use the apparatus.

3.2.3 Example 3

Figure 20:
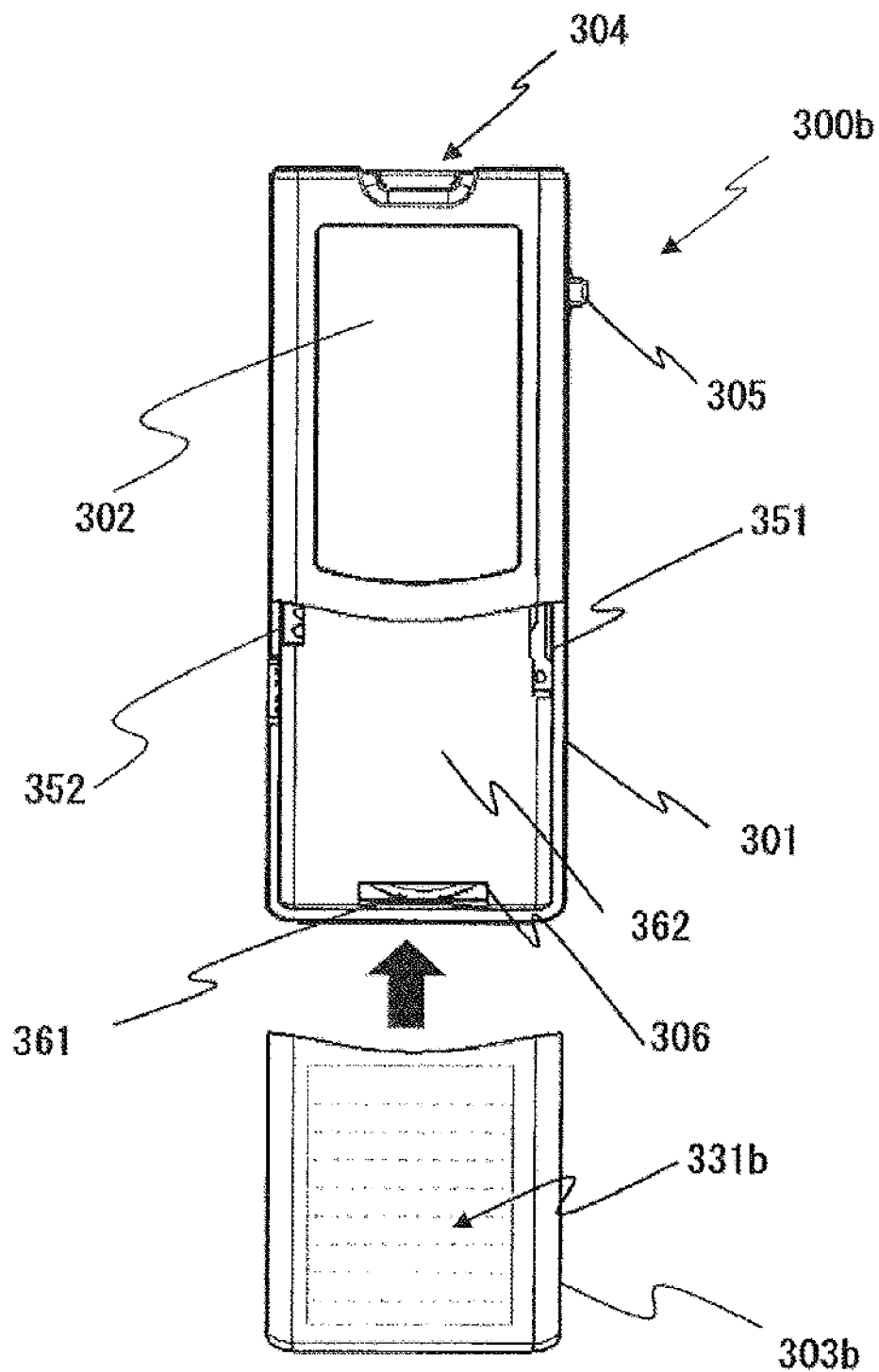
FIG. 20 is a front view illustrating a state in which a panel of a blood sugar level measuring apparatus according to Example 3 of Embodiment 3 is detached.
Figure 21:
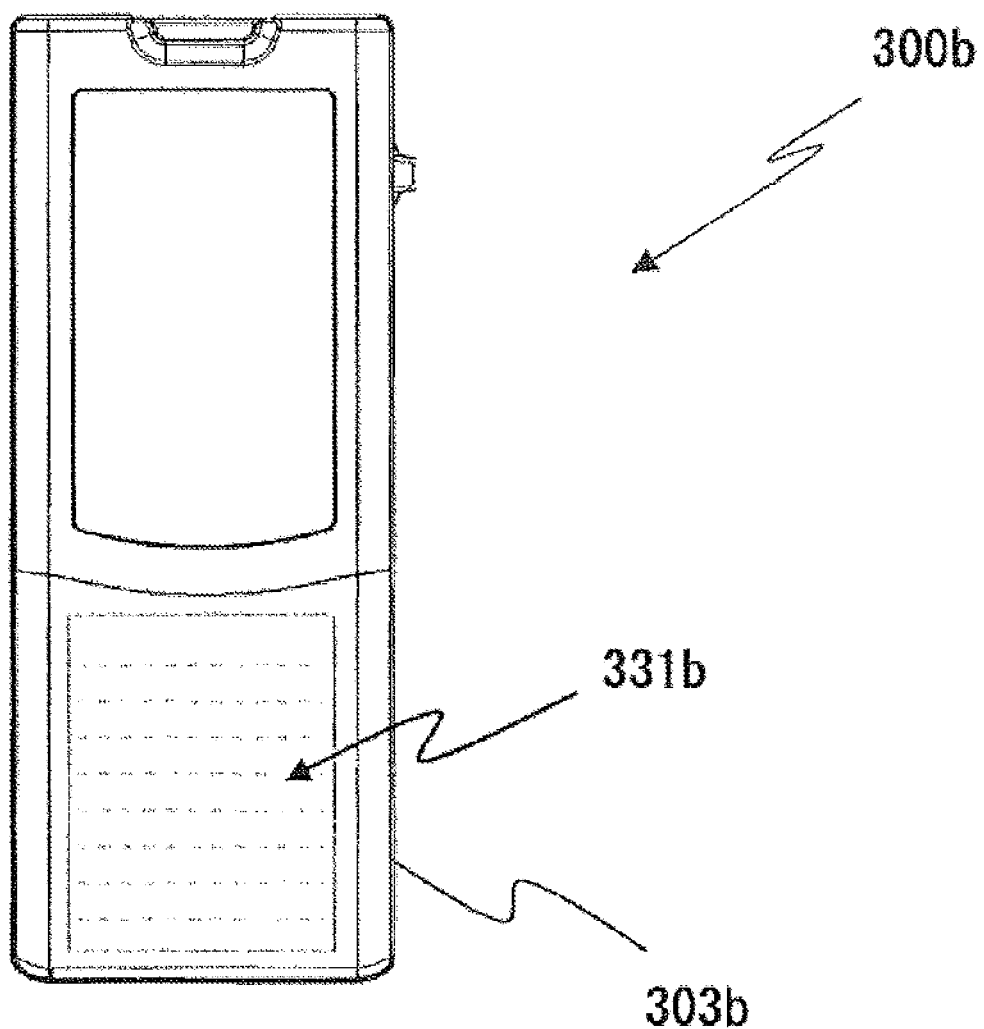
FIG. 21 is a front view illustrating a state in which the blood sugar level measuring apparatus according to Example 3 of Embodiment 3 is used.

In blood sugar level measuring apparatus 300b shown in FIGS. 20 and 21, a surface (made of paper, resin, steel, or the like) is provided on function display section 331b of panel 303, a user freely writes in or attach a photo or an illustration to the surface. A user's name, an address, emergency contacts, references of the measured values, the advice of the medical doctor and the like are written on the surface. The user's information can be helpful for a user's own memory supplement, or can be given to the third party at the time of loss of the apparatus or at the time of emergency.

3.2.4 Example 4

Figure 22:
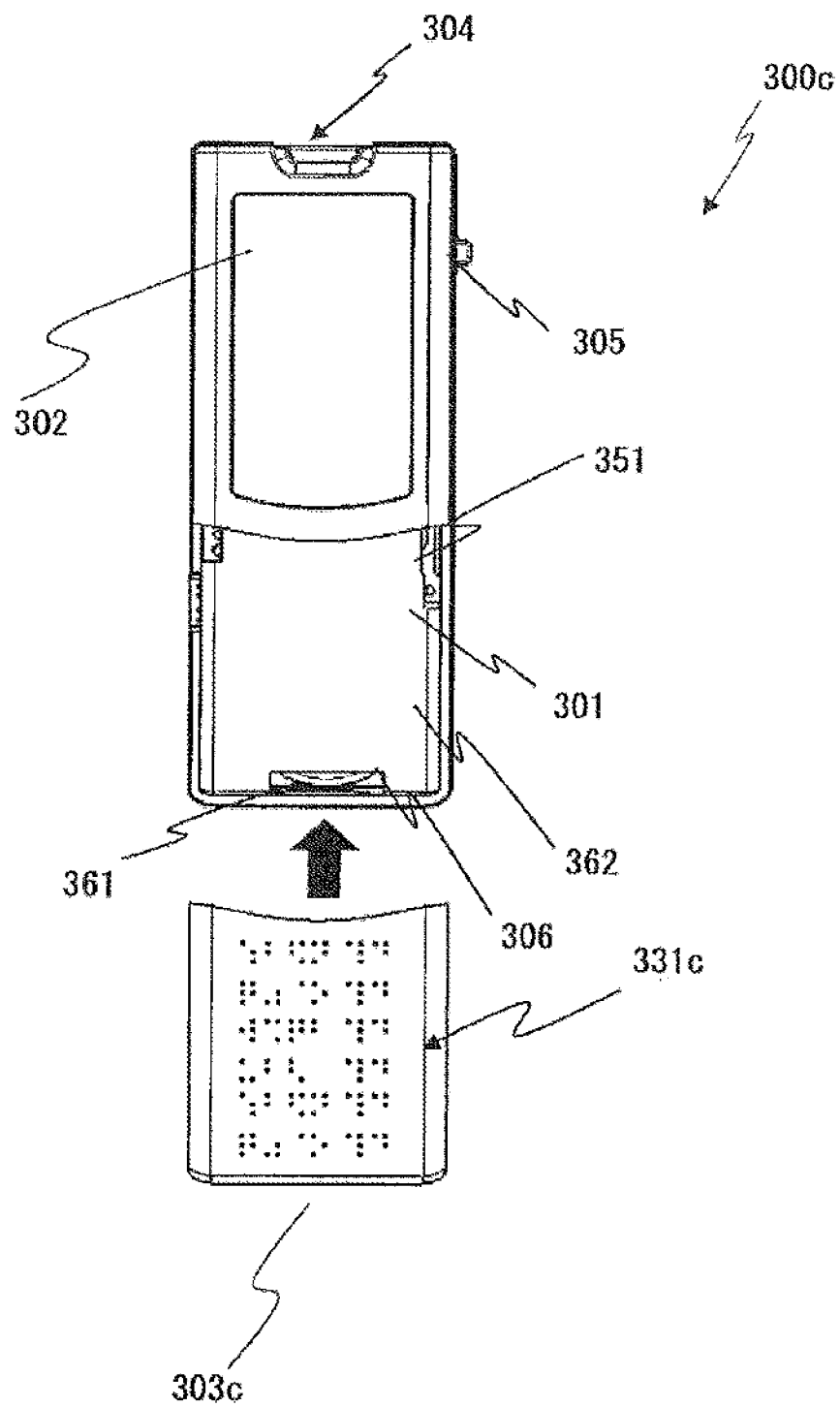
FIG. 22 is a front view illustrating a state in which a panel of a blood sugar level measuring apparatus according to Example 4 of Embodiment 3 is detached.
Figure 23:
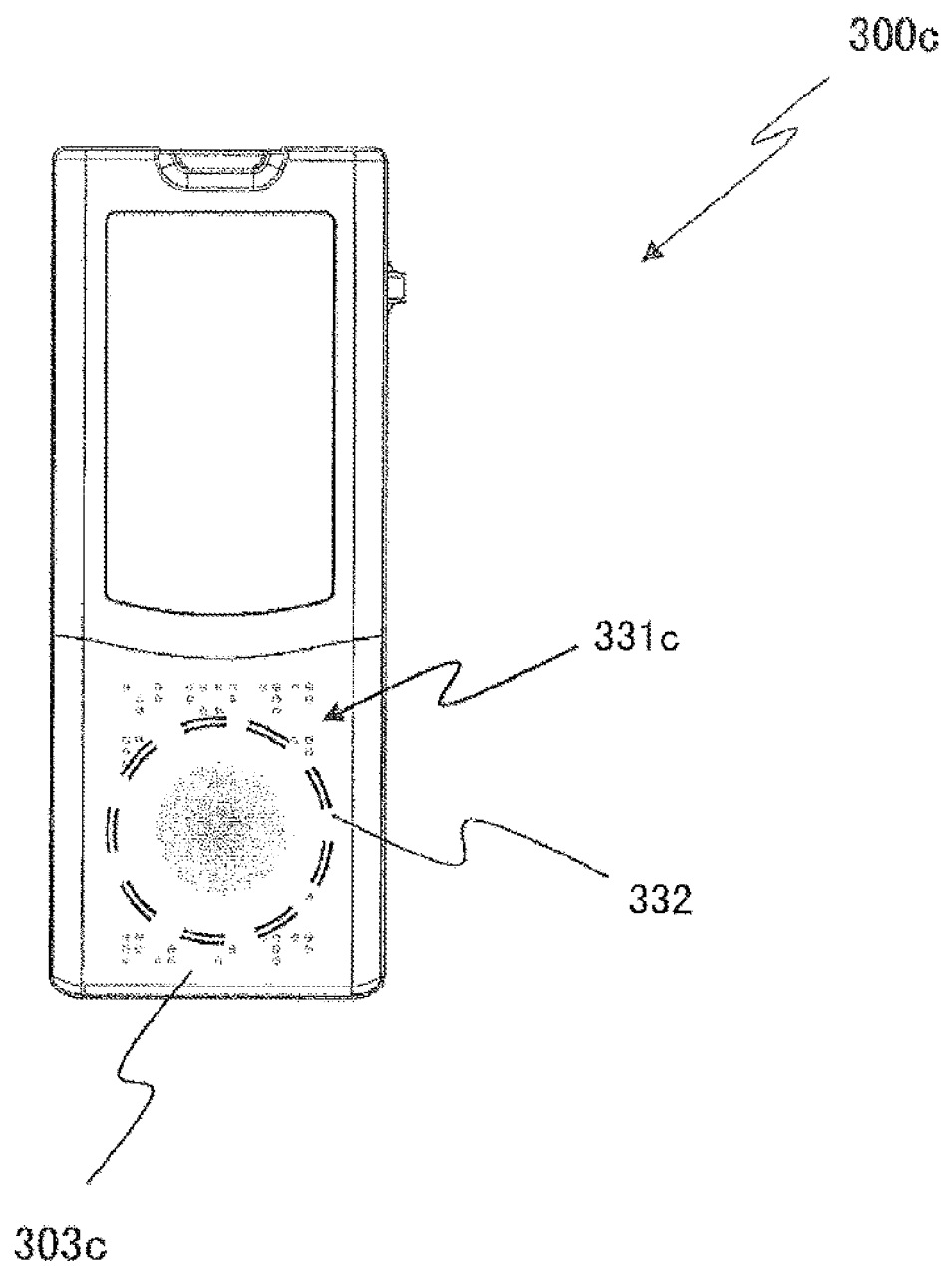
FIG. 23 is a front view illustrating a state in which the blood sugar level measuring apparatus according to Example 4 of Embodiment 3 is used.

In blood sugar level measuring apparatus 300c shown in FIGS. 22 and 23, the information such as the operation manual or the quick guide is displayed in Braille on function display section 331c of panel 303c. This Braille display is realized by processing the surface of panel 303c through resin molding, sheet-metal pressing or the like. Panel 303c may further have speaker 332 as a sound output section, as shown in FIG. 23. In this case, a thin capacitor speaker or the like is used as speaker 332.

Further, a built-in sound output section (voice output section) such as a sounder may be provided on apparatus main body 301, and panel 303c may have a built-in sound output circuit (voice output section) such as a voice synthesizer.

When panel 303c is mounted on apparatus main body 301, speaker 332 of panel 303c is electrically connected to apparatus main body 1 through the connector (not shown in the drawing). In response to the connection, the control unit (not shown in the drawing) provided inside apparatus main body 301 determines whether panel 303c is mounted on apparatus main body 301 by acquiring the identification information of panel 303c. And then the control unit operates the sound output circuit of panel 303c so as to generate a voice from speaker 332 of panel 303c or the sound output section of apparatus main body 301, the voice indicating the operation method, the measurement result or the like.

By providing such panel 303c, it is not necessary for a user to carry the operation manual or the like. Besides, a user who is visually impaired is able to refer to the operation method while touching the Braille, and is also able to hear the operation method through a voice. On the other hand, the user is familiar with the operation and it is not necessary for the user to use the operation manual, it is possible to replace the panel with a different type panel.

3.3 Characteristics of Embodiment 3

As described above, blood sugar level measuring apparatus 300 according to the present embodiment is configured such that a user is able to select necessary information displayed on the function display section (other than 331 of FIG. 15) of panel 303 or main body display section 302 linked with panel 303, and a user is able to easily use the information.

4 Embodiment 4

Hereinafter, Embodiment 4 of the present invention will be described with reference to the accompanying drawings. Blood sugar level measuring apparatus according to the present embodiment is mainly for solving the following problem. Conventionally, as a general method of measuring the concentration of the glucose in the blood, there is a type that uses the oxidation-reduction reaction catalyzed by oxidoreductase. In the method, the blood sugar level sensor chip configured as a disposable type, thereafter a blood drop is adhered onto the blood sugar level sensor chip, and then the blood sugar level is measured. In the blood sugar level sensor chip, an amount of a reductant (or an oxidant) is generated in the enzyme reaction field, the amount depending on the glucose concentration of the blood. When a voltage is applied to the enzyme reaction field through the electrode, electrons are exchanged between the reductant (or the oxidant) and the electrode. The amount of exchanged electrons is measured as oxidation current (or reduction current) in a blood test apparatus, and the blood sugar level is measured on the basis of the current value.

The reaction rate in the enzyme reaction is highly dependent on the temperature, and thus the amount of generated reductant (oxidant) tends to be affected not only by the glucose concentration of the blood but also by the reaction temperature. Hence, most of the conventional blood sugar level measuring apparatuses are configured to correct the temperature and then calculate the final measurement result. The temperature measurement in this case is performed by measuring the temperature in the temperature sensor incorporated in for example the blood test apparatus. The reason of the correction of the blood sugar level based on the temperature is that the detected value of the blood sugar level is fluctuated due to the season, that is, the outside air temperature.

However, in the conventional example, temperature detection means provided in the blood sugar level measuring apparatus is mounted on the circuit board of the apparatus main body. Thus, as a result of the affection of the heat generated by various electronic components mounted on the circuit board, it is difficult to appropriately detect the outside air temperature other than the apparatus.

Further, there is proposed a method of placing the temperature detection means directly under the blood sugar level sensor chip and measuring the temperature of the blood sugar level sensor chip (for example, International Publication No. WO2003/062812). However, the blood sugar level sensor chip is normally directly inserted by a hand, and thus there is an affection of the temperature of the hand. Consequently, there is a problem in that obstructive factors in appropriately detecting the outside air temperature are increased. The corrected blood sugar level based on the temperature detected by such temperature detection mean is not always appropriate. And thereby, the measurement accuracy of the blood sugar level is lowered.

In consideration of the problem, the blood sugar level measuring apparatus according to the present embodiment has the following configuration.

4.1 Configuration of Blood Sugar Level Measuring Apparatus

Figure 24:
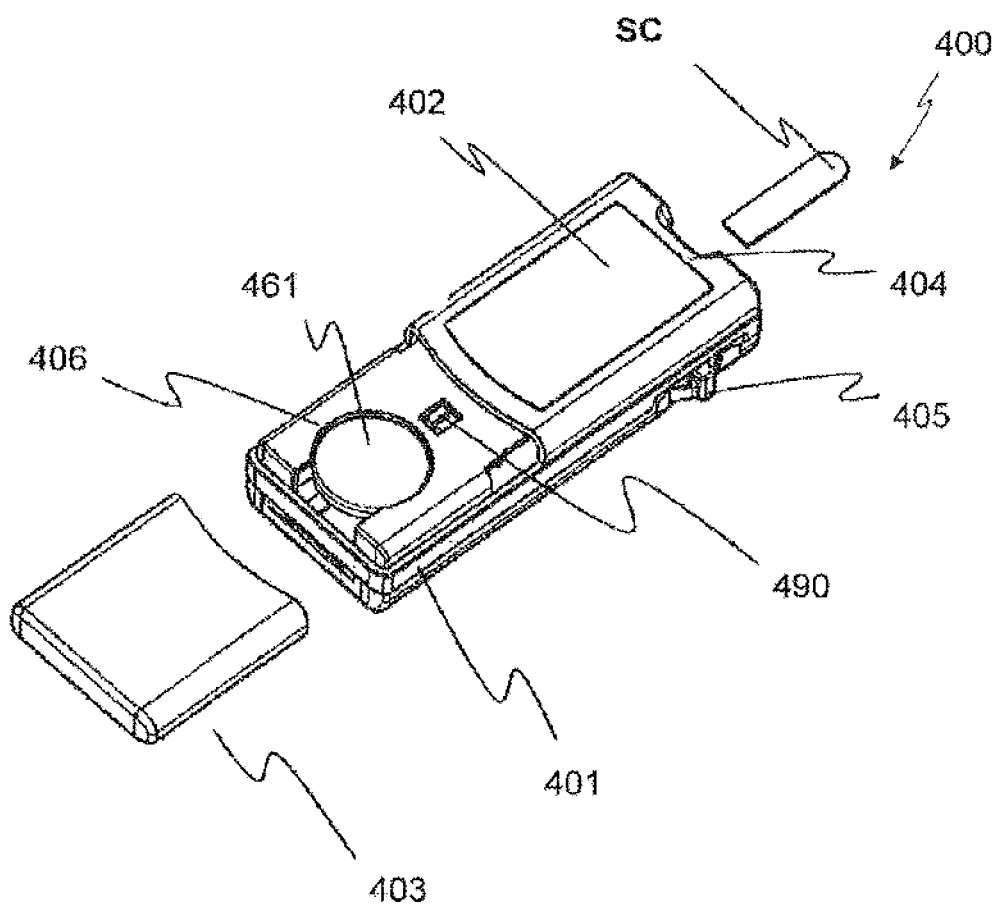
FIG. 24 is a perspective view illustrating a state in which a panel of the blood sugar level measuring apparatus according to Embodiment 4 of the present invention is detached.

FIG. 24 shows the entirety of blood sugar level measuring apparatus 400. Blood sugar level measuring apparatus 400 includes apparatus main body 401 and panel 403. A user inserts disposable blood sugar level sensor chip SC through sensor insertion opening 404, mounts the chip on apparatus main body 401. A small drop of a blood is adhered onto blood sugar level sensor chip SC so as to measure the blood sugar level of the blood. Further, the user is able to replace battery 461 by detaching panel 403 from apparatus main body 401 as shown in FIG. 24.

Apparatus main body 401 is a vertically long casing, and sensor insertion opening 404 is provided on the upper side thereof, blood sugar level sensor chip SC being inserted through the opening 404 at the time of measuring the blood components. Operational section 405 is provided on the other side of apparatus main body 401, the operation of blood sugar level measuring apparatus 400 being performed using operational section 405.

Main body display section 402 is provided on the upper surface of apparatus main body 401, the display section 402 displays measured values of the blood components such as the blood sugar level and other messages. The lower surface is covered by panel 403 which is removable.

Battery housing section 406 is provided on the portion of apparatus main body 1 covered by panel 403, and battery 461 mentioned above is housed in battery housing section 406.

Figure 25:
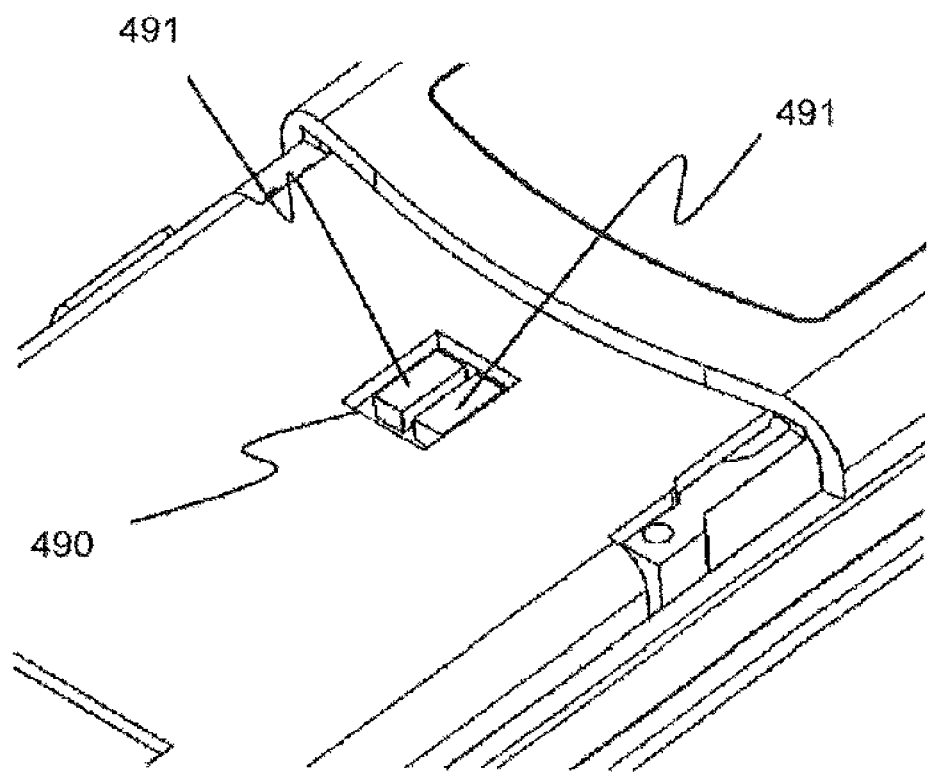
FIG. 25 is an enlarged perspective view illustrating a principal portion of a measuring apparatus of a blood sugar level according to Embodiment 4.

FIG. 25 is a partially enlarged view of blood sugar level measuring apparatus 400 of FIG. 24. Opening portion 490 is provided on the surface of apparatus main body 401 so as to be closer to main body display section 402 than battery housing section 406, and two temperature detection elements 491 constituting the temperature detection means are disposed in the opening portion 490.

That is, such battery 461 and temperature detection element 491 are normally covered by panel 403. Thus, as can be understood from FIG. 24, by sliding panel 403 toward the lower side of apparatus main body 401, such temperature detection element 491 and battery 461 are exposed to the outside of apparatus main body 401.

The relative position of temperature detection element 491 and battery 461 on apparatus main body 401 is arranged such that temperature detection element 491 is exposed to the outside first and then battery 461 is exposed when panel 403 is slid to be detached.

The present embodiment shows an example in which panel 403 is also used as the cover of battery housing section 406 housing battery 461, but the invention is not limited to this. Battery housing section 406 may be provided on the rear side of apparatus main body 1, not on the same surface as main body display section 402. In this case, the battery cover covering battery housing section 406 is provided separately from panel 3 (to be described later).

4.2 Temperature Detection Element

Figure 26:
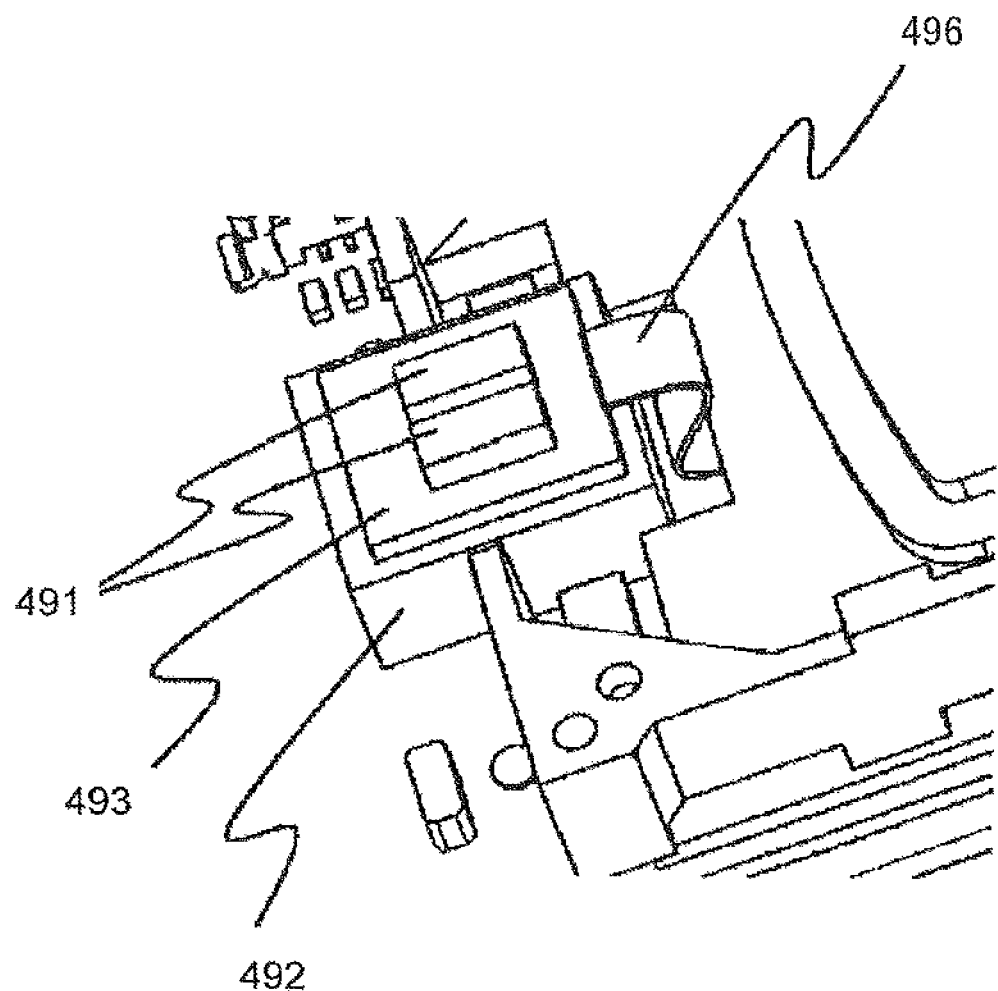
FIG. 26 is an enlarged perspective view illustrating an inner portion of the measuring apparatus of the blood sugar level according to Embodiment 4.
Figure 27:
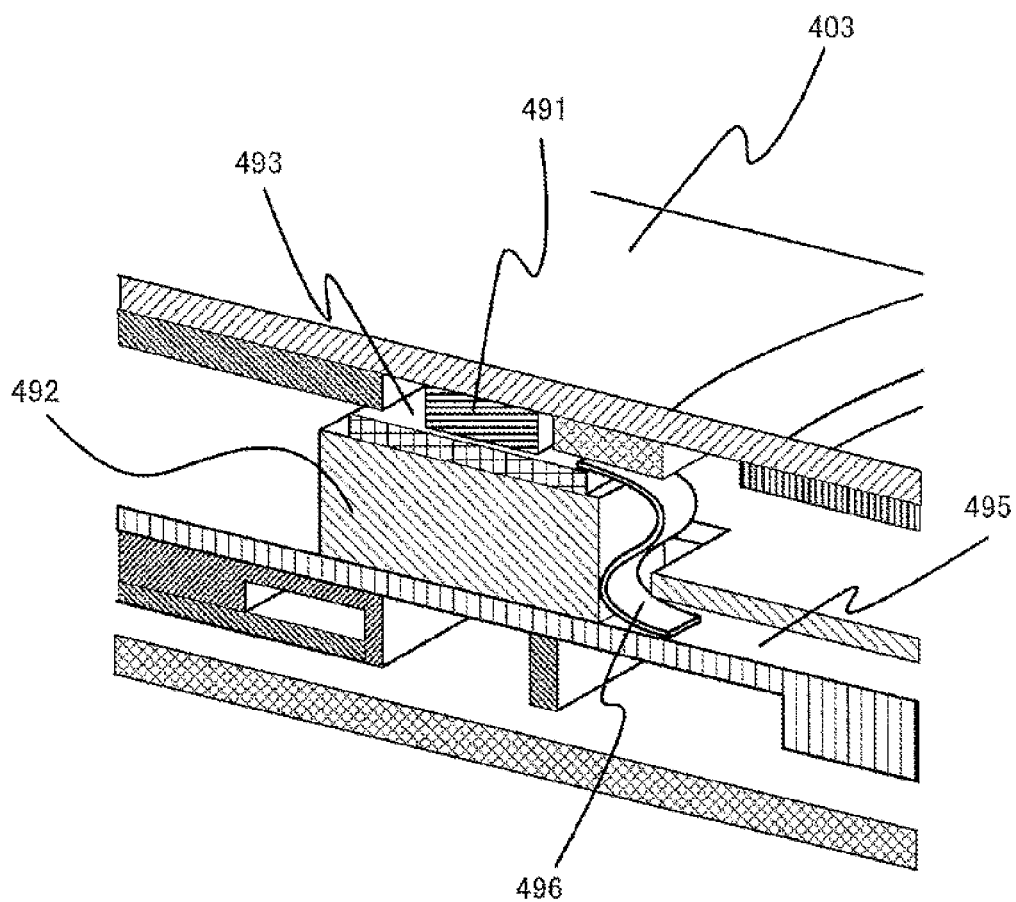
FIG. 27 is an enlarged perspective view illustrating an inner portion of the measuring apparatus of the blood sugar level according to Embodiment 4.

FIGS. 26 and 27 show a configuration of arrangement of temperature detection elements 491. As shown in FIG. 27, circuit board 495 is built in apparatus main body 401, and various electronic components (not shown in the drawing) are mounted on circuit board 495.

Then, mounting base 492 having a heat insulation property is provided above circuit board 495, and sub substrate 493 on which temperature detection element 491 is provided is disposed on mounting base 492. Sub substrate 493 and circuit board 495 are electrically connected through flexible wire 496.

As can be clearly understood from FIG. 27, temperature detection element 491 is covered by panel 403, but is separated from other electronic components via mounting base 492 and is disposed in the vicinity of panel 403. Accordingly, temperature detection element 491 is disposed to be able to more appropriately detect the outside air temperature of the outside of the panel 403.

Further, mounting base 492 may be formed of a member which is elastically deformable like rubber. In this case, mounting base 492 is deformed in the height direction (the vertical direction in FIG. 27). And therefore, panel 3 and temperature detection element 491 provided above mounting base 492 come into contact with each other, when panel 403 is mounted on apparatus main body 401. With such a configuration, temperature detection element 491 is able to more appropriately detect the outside air temperature since the detection element 491 contacts with panel 403 having contact with the outside air.

4.3 Control Unit

Figure 28:
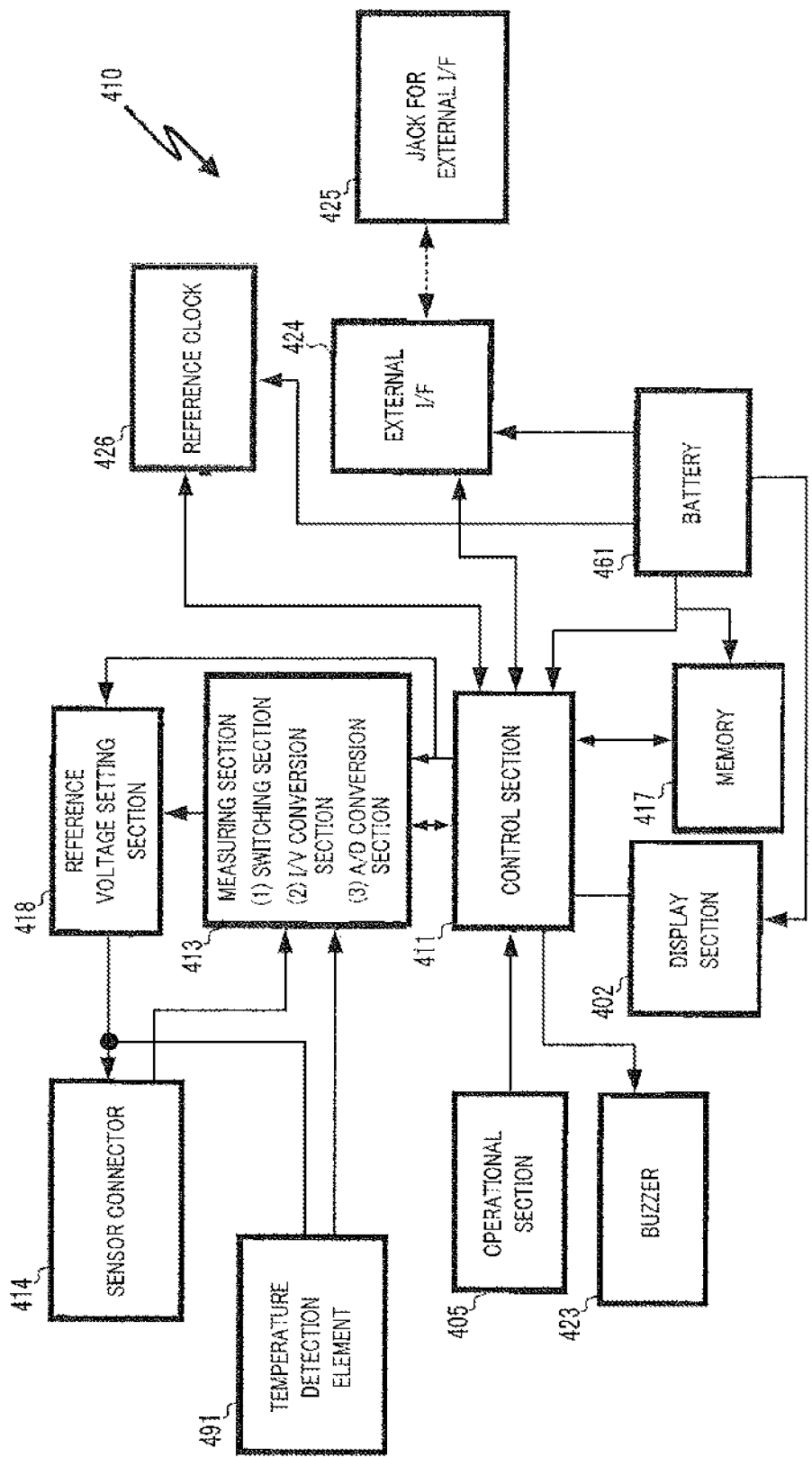
FIG. 28 is a configuration diagram of a control unit of the measuring apparatus of the blood sugar level according to Embodiment 4.

FIG. 28 shows a configuration of control unit 410 of blood sugar level measuring apparatus 400. A brief description will be given of the method of measuring the components of the blood by using blood sugar level sensor chip SC through control unit 410.

First, in response to the command of control section 411, the electrode (not shown in the drawing) for measurement of blood sugar level sensor chip SC is connected to measuring section 413 through sensor connector 414.

Measuring section 413 has a switching section that switches the connection between sensor connector 414 and the electrode for measurement of blood sugar level sensor chip SC, a current/voltage conversion section (an I/V conversion section of FIG. 28) that converts the response current generated by the oxidation-reduction reaction as a signal transmitted from blood sugar level sensor chip SC into a voltage, and an analog/digital conversion section (hereinafter referred to as an A/D conversion section) that converts the analog signal into a digital signal and outputs the signal to control section 411. Measuring section 413 is used to measure the above-mentioned response current or the like generated from blood sugar level sensor chip SC and to obtain the blood sugar level.

By using the switching section within measuring section 413, blood sensing electrode provided on blood sugar level sensor chip SC is connected to reference voltage setting section 418 through sensor connector 414, thereby applying a voltage thereto.

Thereafter, in response to the command of control section 411, a constant voltage is applied between the blood sensing electrodes of blood sugar level sensor chip SC. The corresponding voltage is, for example, a voltage in a range from 0.01 to 2.0 V, preferably in a range from 0.1 to 1.0 V, and more preferably in a range from 0.2 to 0.5 V. The voltage is applied while the blood is introduced into blood sugar level sensor chip SC, specifically, into a capillary portion (not shown in the drawing) provided on blood sugar level sensor chip SC after blood sugar level sensor chip SC is inserted into blood sugar level measuring apparatus 400.

When the blood is introduced into the capillary portion of blood sugar level sensor chip SC, the current flows between the blood sensing electrodes. By detecting the amount of increased current per unit time, it is detected that the capillary portion is filled with the blood.

The current value is converted into a voltage value by the current/voltage conversion section, and further converted into a digital value by the A/D conversion section. And the digital value is input to control section 411. Control section 411 detects that the blood is introduced into the capillary portion within blood sugar level sensor chip SC on the basis of the input digital value.

After the instruction of the blood, for example, the analytes of the blood are made to react to the enzymes provided in blood sugar level sensor chip SC, and the enzymes are made to react to the electronic mediator in a range from 0 to 60 seconds, preferably in a range from 0 to 15 seconds, and more preferably in a range from 0 to 5 seconds.

Subsequently, blood sugar level sensor chip SC is connected to the current/voltage conversion section through sensor connector 414 by operating the switching section within measuring section 413 in response to the command of control section 411. Thereby, the electrodes (for example, the working electrode and the counter electrode not shown in the drawing) for blood component concentration measurement provided on blood sugar level sensor chip SC are electrically connected to reference voltage setting section 418 through sensor connector 414. Subsequently, a constant voltage is applied between the electrodes for blood component concentration measurement in response to the command of control section 411. The corresponding voltage is, for example, a voltage in a range from 0.1 to 5.0 V, preferably in a range from 1.0 to 3.0 V, and more preferably in a range from 1.5 to 2.5 V. The period of time during for applying the voltage is in a range from 0.1 to 30 seconds, preferably in a range from 0.5 to 10 seconds, and more preferably in a range from 1 to 5 seconds. The amount of current is input to measuring section 413 through sensor connector 414, the amount of current flowing between the electrodes for blood component concentration measurement in accordance with the application of the corresponding voltage. Then, the same amount of current is converted into a voltage value by the current/voltage conversion section, and further converted into a digital value by the A/D conversion section. And the digital value is input to control section 411. The concentration data, for example, the glucose concentration data indicating the blood sugar level is stored in memory 417.

As described above, the operation of measuring section 413 is controlled by control section 411, and the measured blood sugar level is displayed on main body display section 402. Further, memory 417 stores the blood sugar level data together with time information which is obtained when the blood sugar level is measured. The electromotive force of each section is supplied by the electromotive force of battery 461 mentioned above. Due to the supplied voltage, a reference voltage is applied between the electrodes for blood component concentration measurement of blood sugar level sensor chip SC through sensor connector 414 in reference voltage setting section 418.

Further, in FIG. 28, temperature detection element 491 is connected to measuring section 413 through flexible wire 496 (refer to FIGS. 26 and 27). Sensor connector 414 is also connected to measuring section 413, and sensor connector 414 is disposed inside sensor insertion opening 404 of apparatus main body 401 shown in FIG. 24.

That is, in the present embodiment by inserting blood sugar level sensor chip SC into sensor insertion opening 404 (refer to FIG. 24), measuring section 413 measures the blood sugar level. At this time, the measured value is corrected by the outside air temperature which is detected by temperature detection element 491. Thereby, an appropriate blood sugar level is measured.

In addition, as can be understood from the above description, in the present embodiment, on the basis of the outside air temperature detected by temperature detection element 491, the blood sugar level measured by measuring section 413 is corrected. The correction of the blood sugar level will be described in detail as follows.

4.4 Correction of Blood Sugar Level

Blood sugar level sensor chip SC connected to sensor connector 414 detects the magnitude of the current generated by the oxidation-reduction reaction of the glucose in the blood present between the electrodes as is well known, and calculates the blood sugar level. The oxidation-reduction reaction of the glucose is greatly affected by the temperature. For example, the temperature is high in the summer, thus the oxidation-reduction reaction is activated, and as a result, the current is also increased. In contrast, the temperature is low in the winter, thus the oxidation-reduction reaction is suppressed, and as a result the current is decreased. Accordingly, when the blood sugar level is measured without considering the outside air temperature, the inappropriate blood sugar level may be measured.

Accordingly, in the present embodiment, as described above, the value of the blood sugar level measured by measuring section 413 is corrected on the basis of the outside air temperature detected by temperature detection element 491. In particular, the outside air temperature is appropriately measured by temperature detection element 491.

Here, the correction of the temperature will be briefly described. After the outside air temperature is measured by temperature detection element 491, the glucose concentration data is corrected on the basis of the outside air temperature data measured by temperature detection element 491, the concentration data being transferred through the sensor connector 414 from the electrodes for blood component concentration measurement within blood sugar level sensor chip SC and being measured by measuring section 413. Examples of normal correction methods include: a method of providing a correction table based on the temperature, storing the table in memory 417, and performing calculation and correction through a correction coefficient for each temperature; a method of providing the data and the table of the glucose concentration corresponding to the temperature in advance, storing the data and the table in memory 417 or the like, and calculating the glucose concentration corresponding to the temperature; and the like.

The temperature measurement by temperature detection element 491 may be performed before, during or after the glucose measurement. Further, during the glucose measurement, the temperature may be continuously measured and monitored. In this case, it is possible to change the glucose measurement time during or the glucose measurement timing in accordance with the change in temperature. For example, when the temperature is greatly changed, the glucose measurement timing may be delayed.

Further, a plurality of temperature detection elements 491 may be provided. Thereby, for example, the temperatures of two temperature detection elements 491 are measured at the same time, and are used in correction of the blood sugar level measurement as the outside air temperature data. Alternatively, when the temperature difference between two temperature detection elements 491 is greater than a predetermined value, a warning of the abnormal state can be given by main body display section 402 or buzzer 423 (FIG. 28). As described above, the plurality of temperature detection elements 491 monitors each other in cooperation, thereby improving the reliability of the temperature detection.

Figure 29:
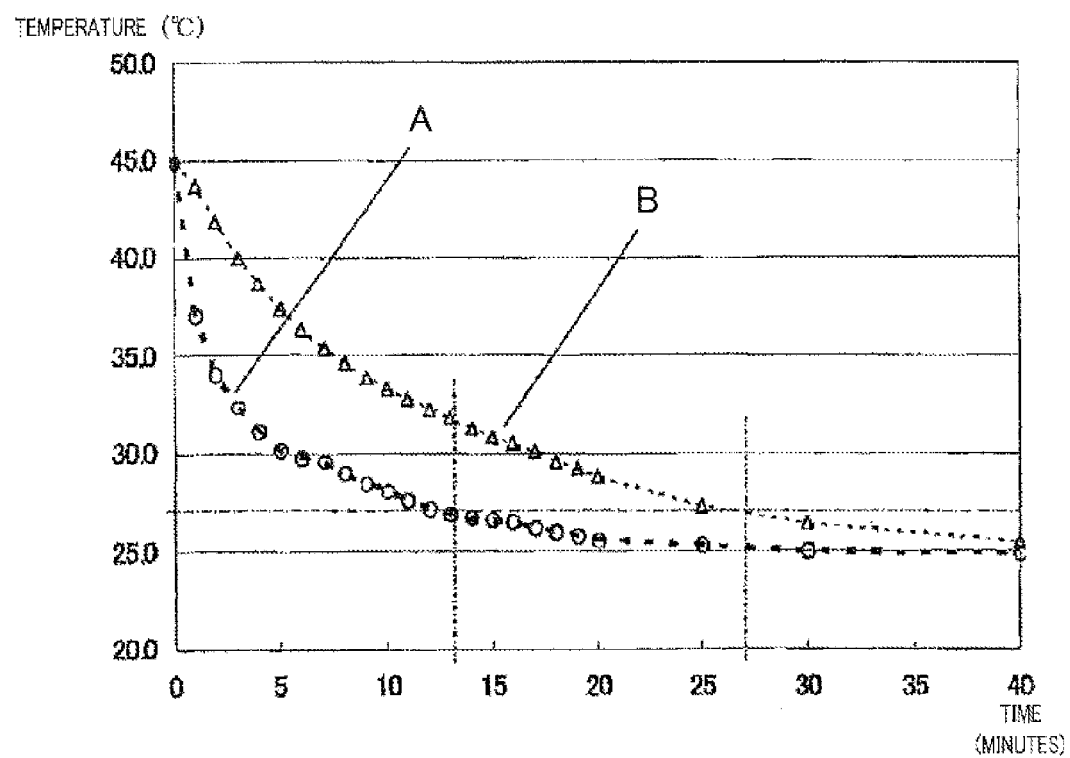
FIG. 29 is a characteristic diagram illustrating temperature characteristics in the blood sugar level measurement.

FIG. 29 shows the temperature characteristics of the conventional example and the present embodiment. FIG. 29 is a graph illustrating the change in the temperature of temperature detection element 491 in a case where the temperature of the outside of the apparatus main body 401 is shifted from the temperature environment of 45 degrees to the temperature environment of 25 degrees.

In the present embodiment, as described above, temperature detection element 491 is disposed at opening portion 490 covered by panel 403 of apparatus main body 401. Hence, as indicated by line A of FIG. 29, it is possible to appropriately detect the outside air temperature earlier than the convention example (shown in line B).

In a specific experiment, it takes about 27 minutes in the conventional example (line B) to reach 27 degrees which is the allowable value in the case of the environmental temperature of 25 degrees. In contrast, it takes about 13 minutes in the present embodiment (line A) to reach the allowable temperature (27 degrees). Furthermore, in the conventional example, the temperature is affected by the heat generated from the electronic components, and is thus hardly likely to reach 25 degrees. However, in the present embodiment, the temperature is not affected by the heat generated from the electronic components, and thus quickly reaches a target temperature of 25 degrees.

4.5 Characteristics of Embodiment 4

As described above, blood sugar level measuring apparatus 400 according to the present embodiment includes: apparatus main body 401 on which blood sugar level sensor chip SC analyzing the components of the blood is mounted; panel 403 that is detachably mounted on apparatus main body 1 so as to partially cover the surface of apparatus main body 401; measuring section 413 that is electrically connected to blood sugar level sensor chip SC and measures the blood components; and temperature detection element 407 that measures the environmental temperature around apparatus main body 401. In the apparatus, temperature detection element 407 is disposed in the vicinity of the surface of apparatus main body 401 at the portion where panel 403 is mounted. With such a configuration, it is possible to improve the measurement accuracy of the blood sugar level.

Consequently, it becomes easy to detect the outside air temperature of the outside of the apparatus main body 401 through temperature detection element 407 contacting with panel 403. As a result, the accuracy of the blood sugar level, which is corrected on the basis of the temperature detected by temperature detection element 407, is increased.

Further, it is possible to provide various types of panel 403, and thus it may be possible to use the panel while replacing it with a desired type as necessary.

4.6 Modified Example

4.6.1 Modified Example 1

Figure 30:
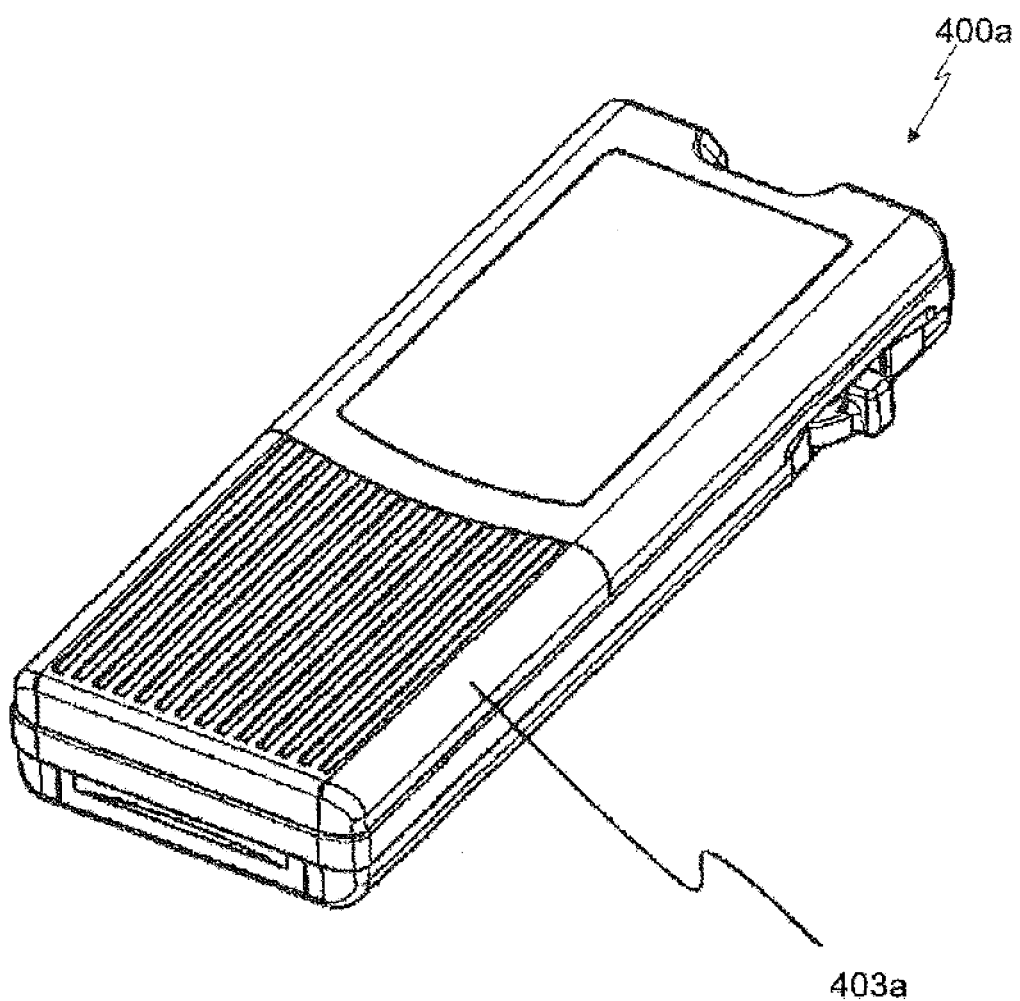
FIG. 30 is a perspective view of a measuring apparatus of the blood sugar level according to Modified Example 1 of Embodiment 4.
Figure 31:
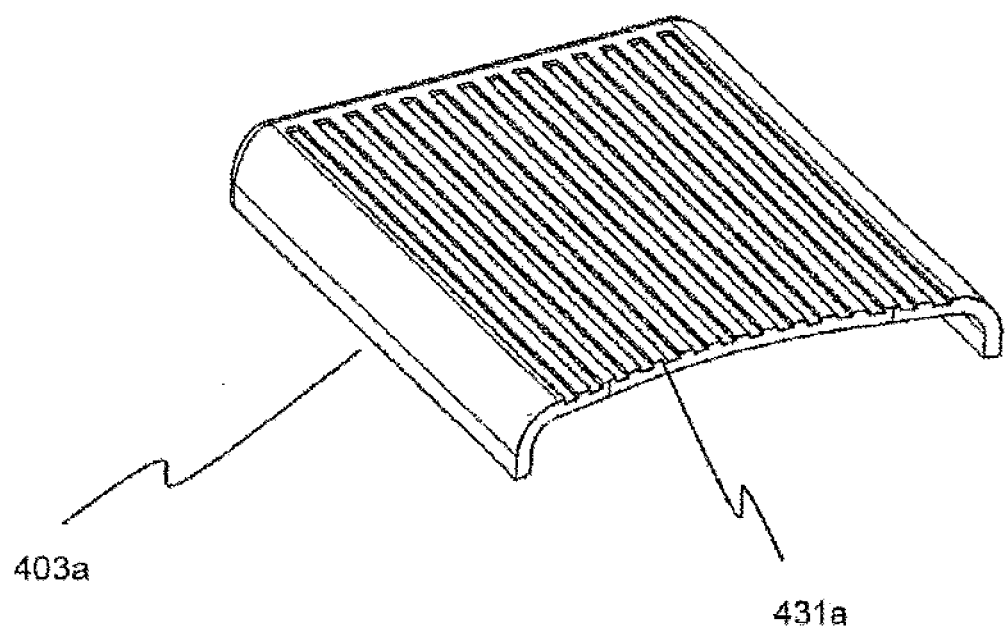
FIG. 31 is an enlarged perspective view of a panel for measuring apparatus of the blood sugar level according to Modified Example 1.

FIGS. 30 and 31 show blood sugar level measuring apparatus 400a according to the modified example of Embodiment 4. Panel 403a of blood sugar level measuring apparatus 400a is different from that of blood sugar level measuring apparatus 400a according to the present embodiment in that unevenness 431a is formed on the surface. By providing unevenness 431a in such a manner, the surface area of panel 403a is increased, and thus it becomes easier to transfer the outside air temperature to temperature detection element 491.

It is apparent that the shape of unevenness 431a is not limited to this if its object is to increase the surface area. For example, in FIGS. 30 and 31, the lines of formed unevenness 431a extend in the longitudinal direction of blood sugar level measuring apparatus 400a. Alternatively, the lines of the formed unevenness extend in both directions of the vertical direction and the longitudinal direction. The unevenness may have a shape (lattice shape) in which the uneven portions intersect with each other. Further, the cross-section shape of the unevenness is not limited to a rectangular shape, and may be a chevron shape or a trapezoidal shape. Furthermore, like a toothbrush shape, the multiple rod-like protrusions may be formed on the surface of panel 403a.

4.6.2 Modified Example 2

Figure 32:
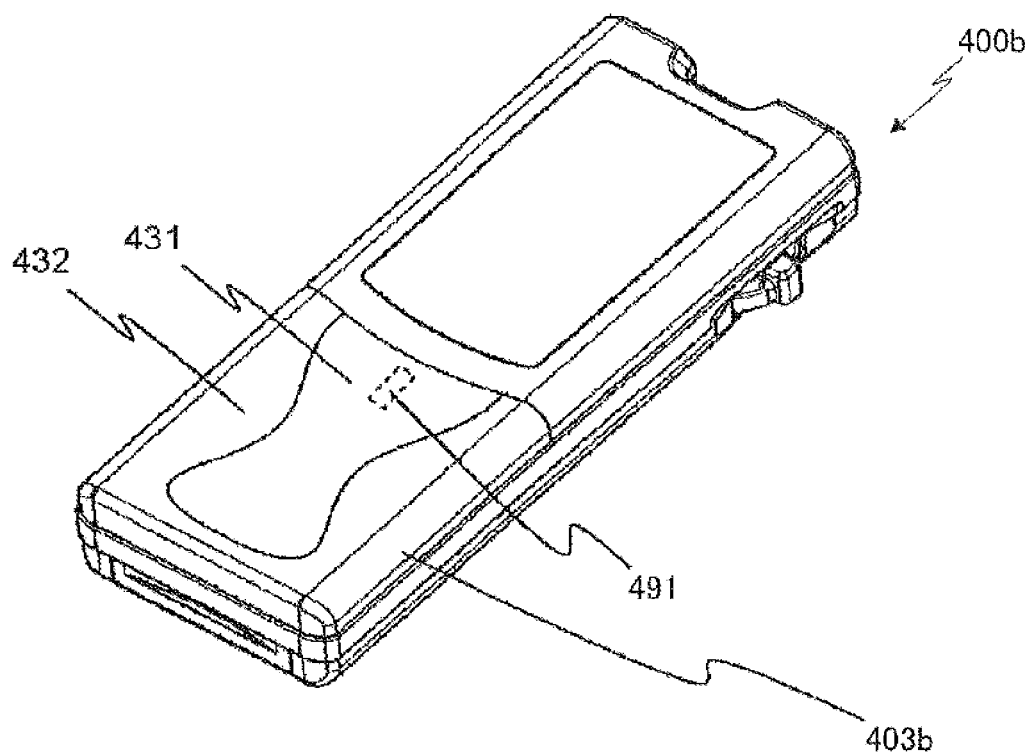
FIG. 32 is a perspective view of a panel for measuring apparatus of the blood sugar level according to Modified Example 2 of Embodiment 4.
Figure 33:
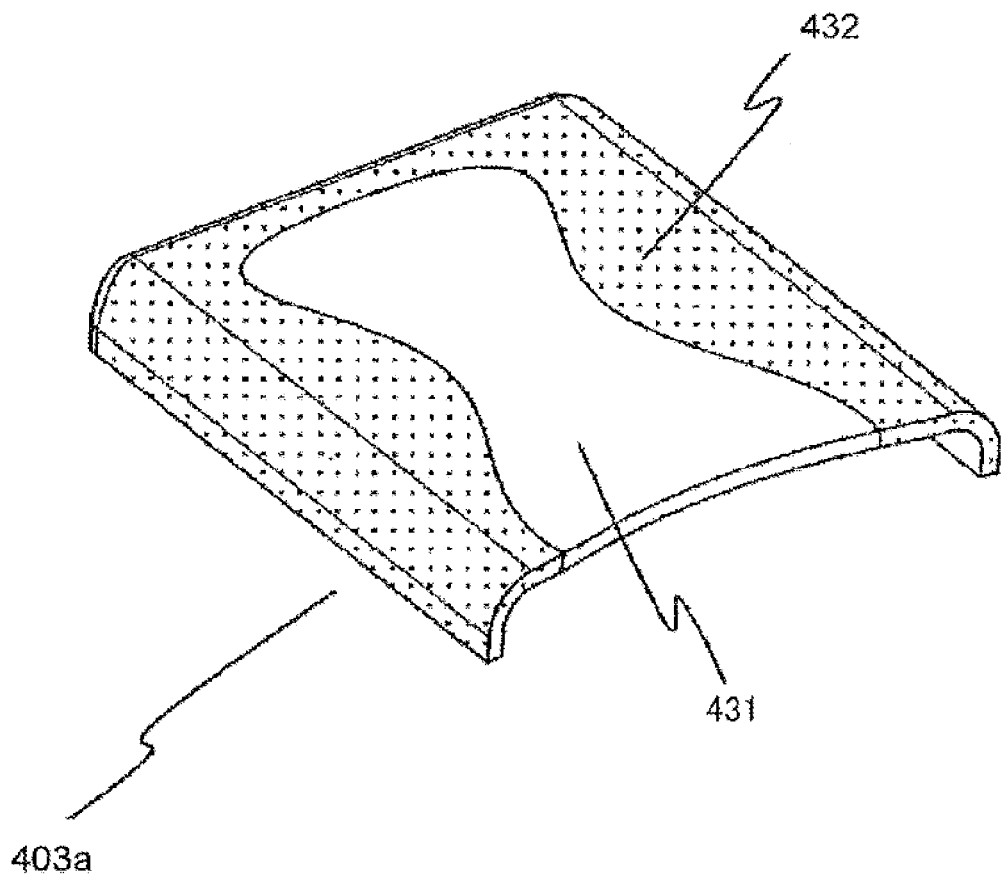
FIG. 33 is an enlarged perspective view of a panel for measuring apparatus of the blood sugar level according to Modified Example 2.

FIGS. 32 and 33 show blood sugar level measuring apparatus 400b according to another modified example of Embodiment 4. In panel 403b of blood sugar level measuring apparatus 400b, portion 431 of panel 403b corresponding to temperature detection element 491 is formed of a material which has a thermal conductivity higher than that of the outer peripheral portion 432. Specifically, portion 431 of panel 403b corresponding to temperature detection element 491 is formed of a material with a high thermal conductivity of preferably 200 W/m·K or more. Outer peripheral portion 432 is formed of a material with a thermal conductivity of preferably 3 W/m·K or less which is lower than the above-mentioned conductivity.

The high thermal conductivity material constituting portion 431 of panel 403b corresponding to temperature detection element 491 is a metal such as aluminum (236 W/m·K), copper (403 W/m·K), silver (428 W/m·K), or gold (317 W/m·K), or an alloy of which the main component is at least one of the above mentioned metals.

Further, the low thermal conductivity material constituting outer peripheral portion 432 is a rubber material of a resin base such as expanded polystyrene (: Styrofoam: 0.03 to 0.04 W/m·K), epoxy resin (0.17 to 0.21 W/m·K), ABS resin (0.1 to 0.18 W/m·K), or silicone rubber (0.15 to 0.16 W/m·K). As described above, outer peripheral portion 432 is touched with a user's hand in order to perform the operation, and thus the temperature of the hand is prevented from being transferred to portion 431 of panel 403b corresponding to temperature detection element 491. Accordingly, it is possible to appropriately detect the outside air temperature through portion 431 of panel 403b corresponding to temperature detection element 491 without the affection of the temperature of the user's hand.

4.6.3 Modified Example 3

Figure 34:
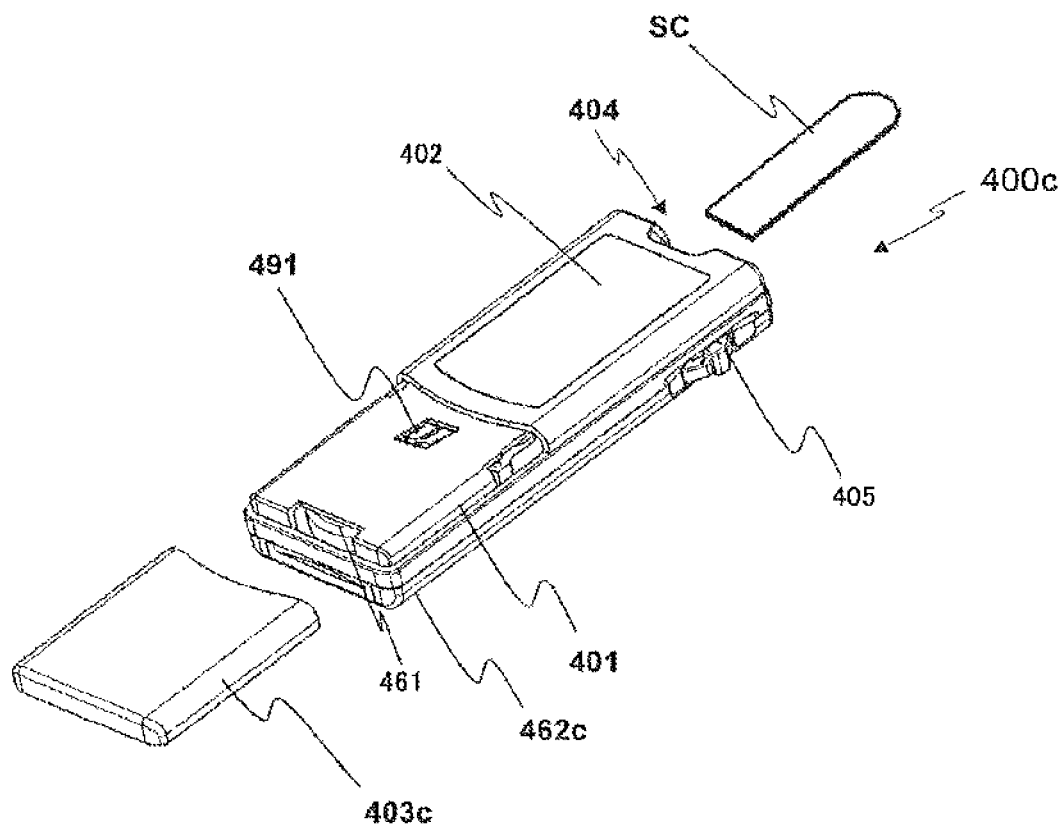
FIG. 34 is a perspective view illustrating a state in which a panel for measuring apparatus of the blood sugar level according to Modified Example 3 of Embodiment 4 is detached.

FIG. 34 shows blood sugar level measuring apparatus 400c according to another modified example of Embodiment 4. In Embodiment 4 mentioned above, panel 403 is also used as the battery cover. However, in the present modified example, panel 403c is not used as the battery cover, independent battery cover 462c is provided on the rear side (the side opposite to the side on which main body display section 402 is provided) of apparatus main body 401, and thus battery 461 is also mounted on the rear side of apparatus main body 401.

With such a configuration, battery 461 and temperature detection element 491 are separated, and thus it is possible to prevent the heat of battery 461 from being transferred to temperature detection element 491. Accordingly, it is possible to appropriately detect the outside air temperature, and thus it is possible to improve the measurement accuracy of the blood sugar level.

In particular, when battery 461 is a rechargeable battery of Li-ion or the like, heat is generated from battery 461 at the time of charge, and thus the present example is effective to suppress the heat influence.

It should be noted that, in this case, the battery housing section (not shown in the drawing) housing battery 461 is provided on the rear side of blood sugar level measuring apparatus 400c.

5. Embodiment 5

Figure 35:
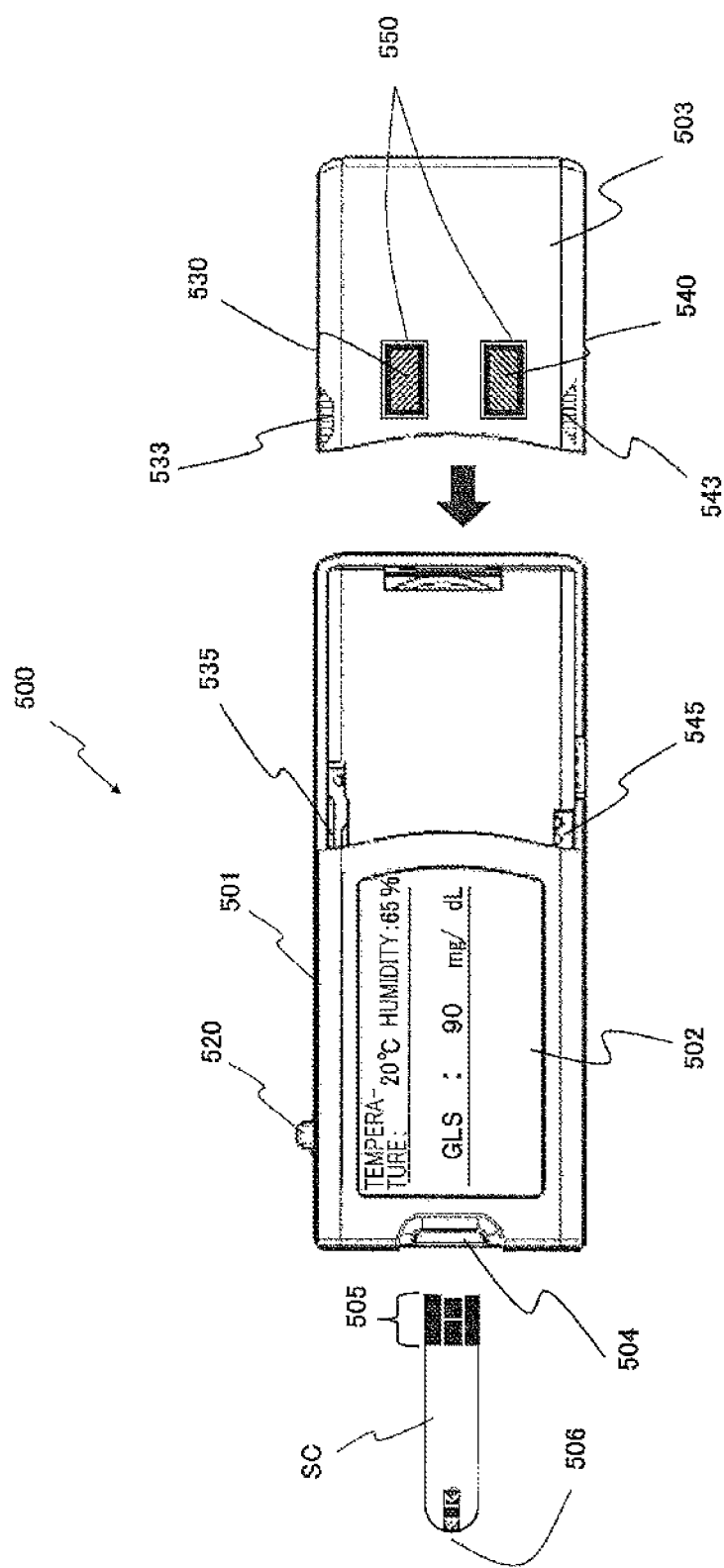
FIG. 35 is a front view illustrating a state in which a panel for measuring apparatus of the blood sugar level according to Embodiment 5 is detached.

Embodiment 5 of the present invention will be described with reference to FIGS. 35 to 37A, 37B, and 37C. FIG. 35 shows biological information measuring apparatus (blood sugar level measuring apparatus) 500 in which the panel is "panel 503 having a temperature sensor or a humidity sensor attached thereto." Specifically, panel 503 is equipped with temperature sensor 540 and humidity sensor 530. By mounting temperature sensor 540 and humidity sensor 530 on panel 503, the temperature and humidity can be measured at the position closer to the outside air. Temperature sensor 540 and humidity sensor 530 are disposed to be exposed on the surface of panel 503. Temperature sensor 540 is electrically connected to connection terminal 543 of the panel, and likewise humidity sensor 530 is connected to connection terminal 533.

Connection terminals 533 and 543 are provided on the rear side of panel 503. When panel 530 is mounted on measuring apparatus main body 501, connection terminal 543 comes into contact with connector for temperature sensor 545 of measuring apparatus main body 501, and connection terminal 533 comes into contact with connector for humidity sensor 535 of measuring apparatus main body. Thereby, panel 503 is connected to the electric circuit of biological information measuring apparatus 500.

Thereby, the temperature data measured by temperature sensor 540 provided on panel 503 can be used in correction when an accurate value of the blood sugar level is calculated. Further, blood sugar level sensor SC may be deteriorated by the reaction of sensor reagents and the like caused by humidity. Accordingly, by measuring the humidity data through humidity sensor 530, a caution, a warning or the like for urging a user to appropriately keep the sensor can be displayed or the sound notification (for example, a warning buzzer or the like) thereof can be performed, in a case of a predetermined or more amount of humidity or in a case where a predetermined time or more has passed in the humidity state.

FIG. 35 shows an example in which the temperature data, the humidity data, and the blood sugar level (glucose) data are displayed on display section 502. In FIG. 35, each data is displayed along the longitudinal direction of measuring apparatus main body 501. Further, in FIG. 35, temperature sensor 540 and humidity sensor 530 are exposed on the surface of panel 503. Therefore, it is necessary to provide opening portions 550 for temperature sensor 540 and humidity sensor 530. The gap between each opening portion 550 and each sensor (temperature sensor 540, humidity sensor 530) is filled with a sealing member, or a transparent film cover is provided over the entire opening portions 550. The reason is to prevent moisture, liquid, dust, and dirt from entering from opening portions 550 of humidity sensor 530 and temperature sensor 540 into apparatus main body 501, and to protect each sensor.

Further, temperature sensor 540 and humidity sensor 530 are provided at arbitrary positions. For example, it is preferable to provide the sensors at positions where the sensors are unlikely to be touched by a finger or the like. For example, when panel 503 is mounted, the panel side surface is likely to be gripped by a finger. And the side surface or the rear surface of apparatus main body 501 is likely to be gripped by a finger during the measurement. Accordingly, as shown in FIG. 35, temperature sensor 540 and humidity sensor 530 are disposed on the front portion (the side coplanar with the display section of the main body) of panel 503, and at the locations separated at a certain distance (about a half width or a full width of the finger: about 5 to 12 mm) or more away from the side edge of the front portion. Thereby, the user's finger in use is less likely to come into contact with temperature sensor 540 and humidity sensor 530. Consequently, by reducing artificial effects, it is considered to achieve reliable measurement.

When separate temperature sensor 540' (refer to FIG. 36) is provided in measuring apparatus main body 501 (mostly in the conventional model), by measuring the temperatures through both temperature sensor 540' inside apparatus main body 501 and temperature sensor 540 of panel 503, the temperature difference therebetween may be calculated. When the temperature difference is equal to or greater than a predetermined value, a user may be notified of the warning or the caution, or may be urged to wait for measurement. When the temperature difference is equal to or less than the predetermined value, the temperature difference is used as the temperature data used in the correction of the measured values (for example the measured glucose level). As the used temperature data, the temperature data of either one of temperature sensor 540' inside apparatus main body 501 and temperature sensor 540 of panel 503 may be selected, and the average value of each temperature data may be used.

Temperature sensor 540 or humidity sensor 530 is supplied with electricity from the electric circuit of apparatus main body 501 through connector for temperature sensor 545, connector for humidity sensor 535, and connection terminals 543 and 533. A temperature signal and a humidity signal from temperature sensor 540 and humidity sensor 530 are input to the electric circuit of the main body through these connection portions. Then, the temperature and the humidity is measured.

In a separate modified example, temperature sensor 540 or humidity sensor 530 may be disposed on the rear side of panel 503. In such a case, there is a low possibility that water drops or dusts enter into the main body, and thus opening portions 550 for the sensors may not be provided on panel 530. That is, the above-mentioned process such as shielding using a sealant or covering using a film becomes not necessary. When temperature sensor 540 is provided on the rear side of the panel, the temperature is measured through panel 503 having contact with the outside air. Panel 503 having contact with temperature sensor 540 is made of a material with a high conductivity, whereby the outside air temperature is smoothly transferred to temperature sensor 540. Hence, it is possible to accurately measure the outside air temperature through temperature sensor 540.

Figure 36:
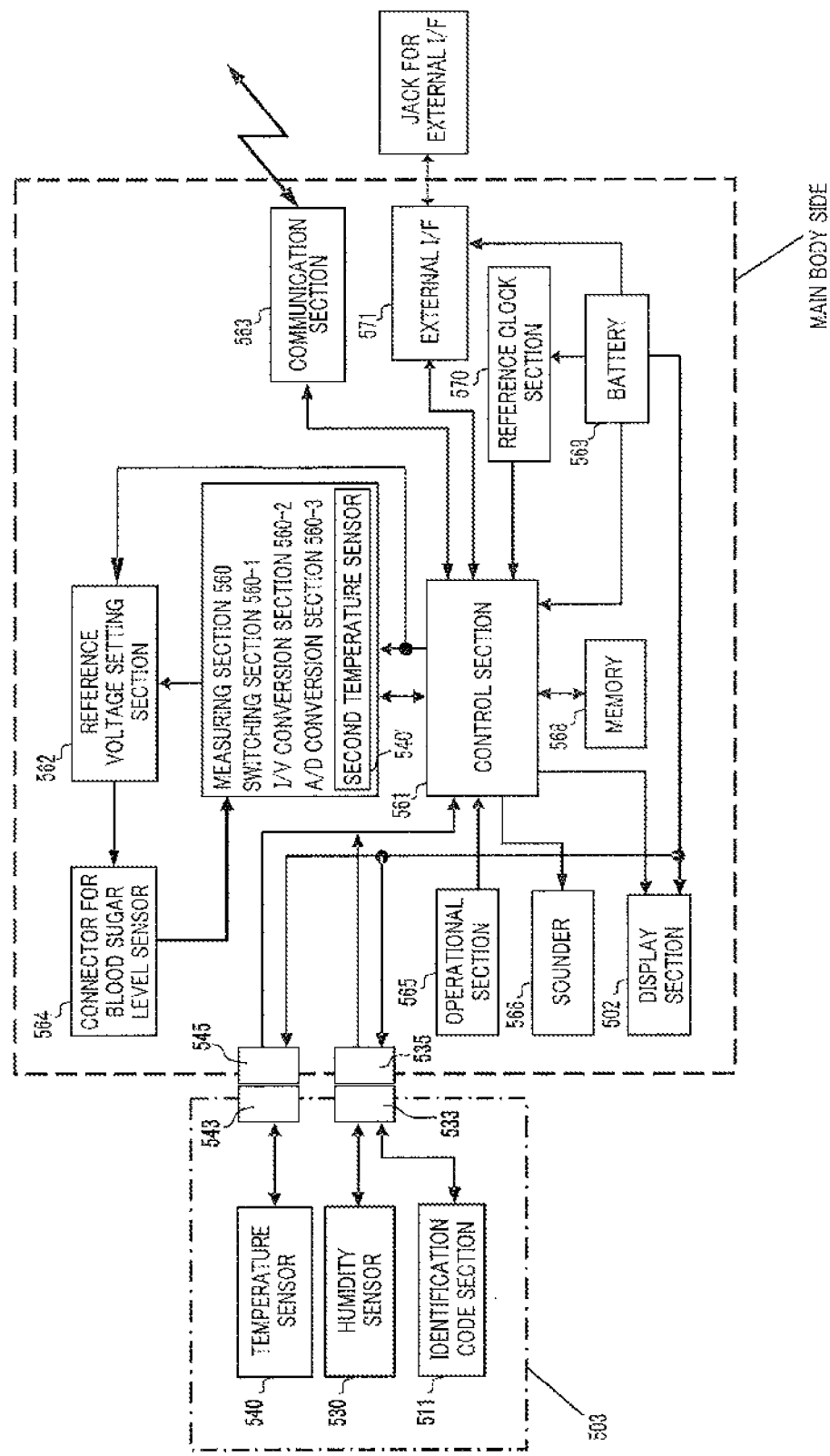
FIG. 36 is a configuration diagram of a control unit for measuring apparatus of the blood sugar level according to Embodiment 5.

FIG. 36 shows electric circuit blocks of biological information measuring apparatus (glucose measuring apparatus) 500 shown in FIG. 35. The range of the left dotted line indicates panel 503, and the range of the right dotted line indicates apparatus main body 501. FIG. 36 shows a case where one temperature sensor 540 and one humidity sensor 530 are provided on panel 503. The plurality of temperature sensors 540 or humidity sensors 530 may be provided, and only one of temperature sensor 540 and humidity sensor 530 may be provided.

Panel 503 is provided with temperature sensor 540, humidity sensor 530, connection terminals 533 and 543 for connection with measuring apparatus main body 501. Apparatus main body 501 is provided with connector for temperature sensor 545 having contact with connection terminal 543 and connector for humidity sensor 535 having contact with connection terminal 533. When panel 503 is mounted, panel 503 is electrically connected to control section 561 inside apparatus main body 501 and the like, so as to supply an electric power to temperature sensor 540 and humidity sensor 530. Electric signals from temperature sensor 540 and humidity sensor 530 are input to apparatus main body 501, and the temperature data and the humidity data are measured. Further, the main power supply of apparatus main body 501 may be activated in response to the mounting of panel 503 on apparatus main body 501.

In electric circuit blocks shown in FIG. 36, the following elements are connected: control section 561 that performs control of biological information measuring apparatus 500; measuring section 560 that is connected to control section 561 and performs glucose measurement through blood sugar level sensor SC; reference voltage setting section 562 that supplies a voltage applied to blood sugar level sensor SC through connector for blood sugar level sensor 564; operational section 565 that includes buttons and the like for giving an instruction to perform the operation of the measuring apparatus; display section 502 (liquid crystal display) that displays a measurement result, the current state and an error, or the like; sounder 566 that makes a sound at the time of completion or at the time of error; memory 568 that stores measurement data, setting data, and the like; reference clock section 570 that supplies a reference clock to control section 561; battery 569 that supplies electricity to the respective sections; external interface (I/F) section 571 for connection with external devices; and communication section 563 that performs data communication with external devices such as PC through wireless network.

Further, as shown in FIG. 36, when second temperature sensor 540' is provided on measuring section 560, second temperature sensor 540' is also connected to control section 561. Measuring section 560 mentioned above is connected to blood sugar level sensor SC through connector for blood sugar level sensor 564, the sensor SC being inserted through sensor insertion opening 504 of measuring apparatus main body 501. Further, measuring section 560 includes switching section 560-1, current/voltage conversion section (I/V conversion section) 560-2, and analog/digital conversion section (A/D conversion section) 560-3. Measuring section 560 determines the model of blood sugar level sensor SC, detects whether blood sugar level sensor SC is mounted, detects whether the blood as biological sample is adhered onto blood sugar level sensor SC, measures the glucose, measures the hematocrit value, and so on.

The digital information measured by measuring section 560 is fetched in control section 561, and the result of the glucose level at the reference temperature is calculated on the basis of a calibration curve or a calculation table of multiple regression equation by using data such as the glucose data, the hematocrit value, and the temperature data. The calculated result is displayed on display section 502 so as to be notified to a user. In Embodiment 5, temperature data and humidity data are extracted from humidity sensor 530 or temperature sensor 540 provided on panel 503. Hence, the temperature data substantially the same as the outside air temperature can be extracted. By using such data in correcting and/or calculating the glucose level, the measurement accuracy of the glucose level (blood sugar level) is improved.

Further, the humidity data from humidity sensor 530 may be displayed on display section 502, and a warning may be given to a user if the apparatus is used in a high humidity day or in a damp place. Specifically, when the humidity data indicates the humidity of 70% or more, a distinguishing mark of humidity display with "red" is displayed on display section 502. At the same time, by displaying the caution message (such as a message that recommends that unused blood sugar level sensor SC is securely housed in a bottle for the sensor only) on display section 502, user's attention is called. Further, when the humidity data indicates the humidity of 85% or more, sounder 566 generates a warning sound, and the humidity is displayed in red to be flickered on display section 502. At the same time, a warning message of "unsuitable for measurement" is displayed in a color in the range from orange to red on display section 502.

Furthermore, on the basis of both data of the temperature data and the humidity data, it may be determined whether or not to warn a user. For example, if the humidity is equal to or greater than 80% and the temperature is equal to or greater than 30 degrees, or if the temperature is equal to or less than 5 degrees, a warning message is given together with the above-mentioned message, the warning message being that "Measurement condition is unsuitable. Please change the measurement place." As a result, it is possible to prompt a user to cope with the problem.

Panel 503 is equipped with identification code section 511 to which a code for identifying the panel type is allocated. The identification code is input to apparatus main body 501 through connectors (connection terminal 533, and connector for humidity sensor 535). Then, control section 561 identifies the type of panel 503. As a result, it is recognized that the mounted panel is "panel 503 having the temperature sensor or the humidity sensor attached thereto".

In measuring apparatus 500 shown in FIG. 35, connection terminals 533 and 543 are provided in panel 503, and connector for temperature sensor 545 and connector for humidity sensor 535 are provided on apparatus main body 501. Connection terminals 533 and 535 are integrated into a single terminal connector for temperature sensor 545 and connector for humidity sensor 535 are integrated into a single connector, and thus the terminals are formed as a pair of connection portions. The pair of connection portions is provided with input/output connection terminals for power supply, temperature sensor, humidity sensor, and identification code, and the like. Thereby, the mechanism of the connection portions is simplified, and thus it becomes easier to standardize and miniaturize apparatus main body 501.

Figure 37A:
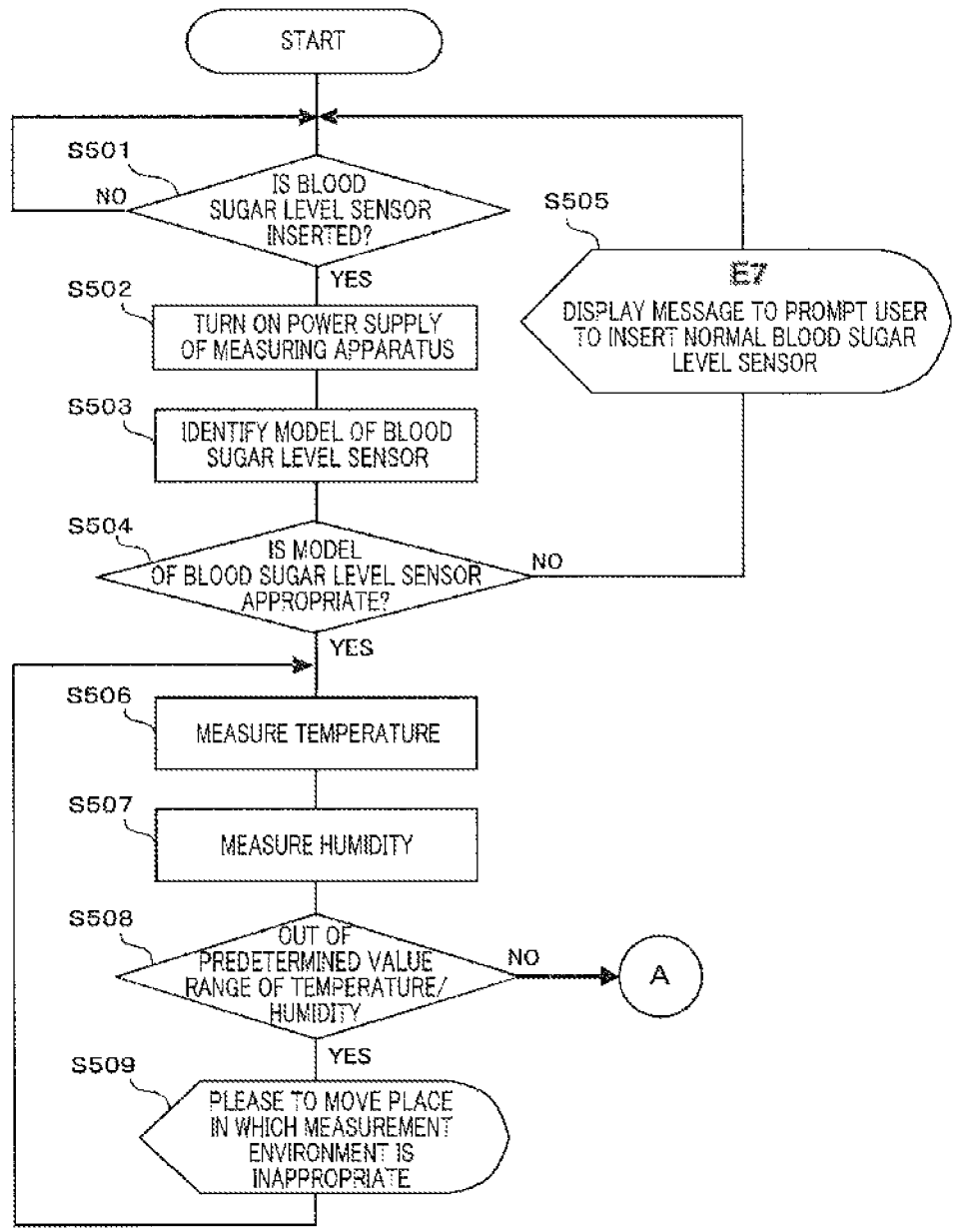
FIG. 37A is a flowchart illustrating a process performed by the control unit of the blood sugar level measuring apparatus according to Embodiment 5.
Figure 37B:
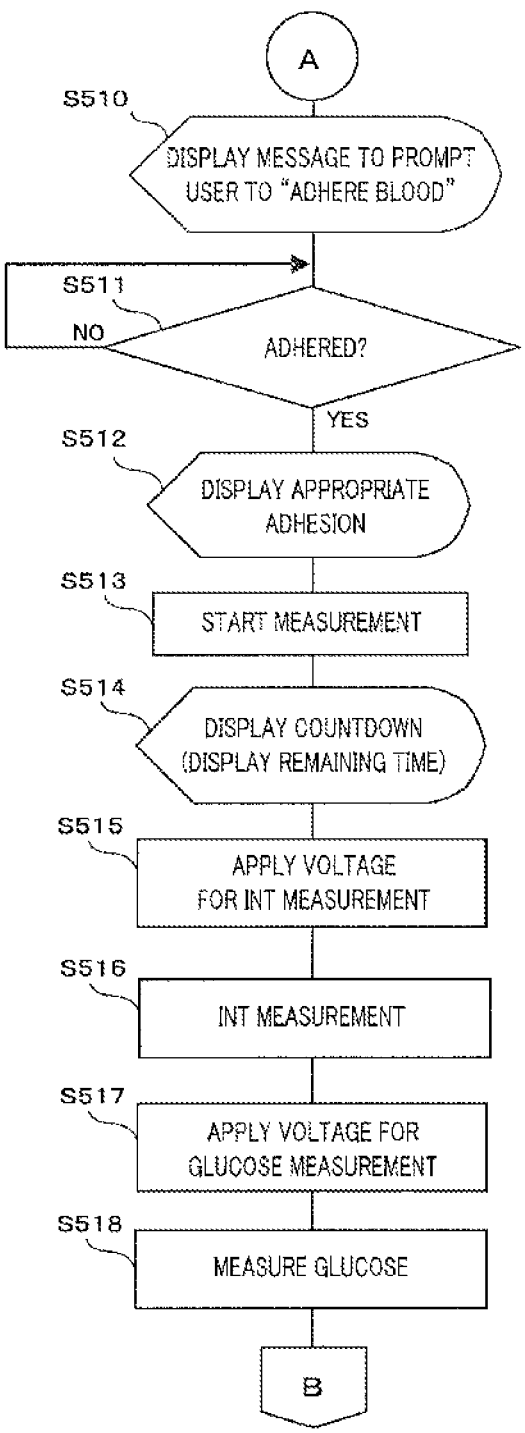
FIG. 37B is a flowchart illustrating the process performed by the control unit of the blood sugar level measuring apparatus according to Embodiment 5.
Figure 37C:
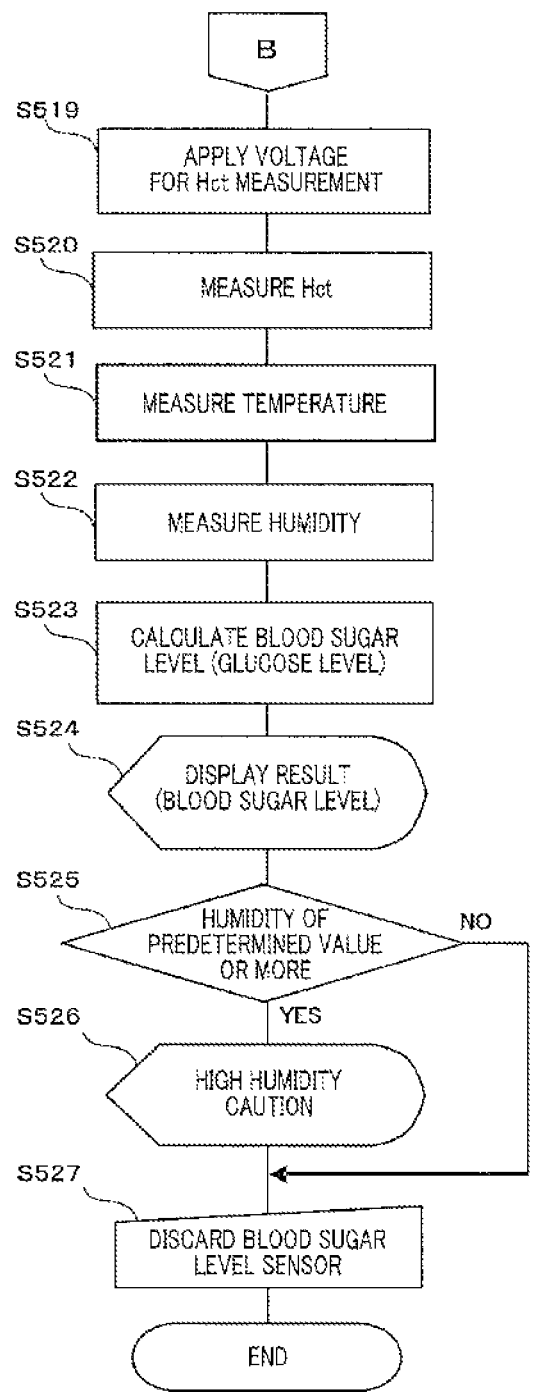
FIG. 37C is a flowchart illustrating the process performed by the control unit of the blood sugar level measuring apparatus according to Embodiment 5.

FIGS. 37A to 37C show an operation flow of biological information measuring apparatus 500 shown in FIG. 35. The flow represents a flow in a state where "panel 503 having a temperature sensor or a humidity sensor attached thereto" is mounted on measuring apparatus main body 501. Hereinafter, the respective steps will be described.

Step S501: it is confirmed that blood sugar level sensor SC is mounted. It is determined whether blood sugar level sensor SC is mounted, by measuring electric conductivity/resistance value between the terminals of the contact portion of the measuring apparatus, the terminals contacting with connection portion 505 (FIG. 35) of blood sugar level sensor SC. After checking that blood sugar level sensor SC is mounted, the process advances to step S502.

S502: main power supply of measuring apparatus 500 is turned ON so as to display an information on display section 502. By pressing a power button provided on measuring apparatus 500, the main power supply can be turned ON. In FIG. 35, JOG dial 520 of a push function section is shown, but the main power supply is turned ON by pushing JOG dial 520 for 2 seconds or more.

S503: next, it is determined whether the model of blood sugar level sensor SC mounted on measuring apparatus main body 501 is correct. The determination of the model is performed on the basis of the pattern provided on connection portion 505 (refer to FIG. 35) of blood sugar level sensor SC.

S504: if the model is appropriate, the process advances to step S506.

S505: if model is inappropriate, model error (error code of "E7" of FIG. 37A) is displayed, an indication that blood sugar level sensor SC is replaced with appropriate one is displayed, and the process advances to S501. As might be expected, the display of the model error is not limited to the error code (E7) display, and a message indicating "model error" may be displayed. In particular, when display section 502 (refer to FIG. 36 and the like) is a color liquid crystal display of the dot matrix type, the error massage can be emphasized, a visibility of the error message is improved, user's attention is called by changing the color of the characters indicating the error message into red. And thus, it is possible to prompt the user to quickly cope with the error.

S506: the temperature data is input from temperature sensor 540 provided in panel 503.

S507: the humidity data is input from humidity sensor 530 provided on panel 503.

S508: if the temperature data and the humidity data are in a predetermined value range, the process advance to S510 (FIG. 37R). If the temperature data and the humidity data are out of the predetermined value range, the process advances to step S509. In the above description, both the temperature data and the humidity data are used, but in some cases, it may not be indispensable to use both of them. For example, it may suffice to make determination on the basis of only the temperature data as if the temperature is equal to or greater than 45 degrees or is equal to or less than 5 degrees; or it may also suffice to make determination on the basis of only the humidity data as if the humidity is equal to or greater than 90%. Such a temperature and a humidity is beyond a rating such as operation guarantee temperature and humidity of measuring apparatus 500. Therefore this case is unsuitable for the measurement.

S509: if the data of the temperature and humidity indicates beyond a predetermined range, since the measurement environment is inappropriate, the display for prompting movement of the measurement place is performed. A warning message that "Measurement condition: unsuitable. Move the place" with red-based characters is displayed on display section 502, when the humidity is equal to or greater than 80% and the temperature is equal to or greater than 30 degrees; the temperature is equal to or less than 5 degrees; the temperature is equal to or greater than 45 degrees; or the humidity is equal to or greater than 90%, for example. The temperature or the humidity can be displayed in a color different from a normal color (blue-based, green-based, or black-based color). Alternatively, a flickering display can be performed for each of them. And therefore a user is prompted to cope with the problem. Further, the sounder may generate a warning sound.

S510: after S510, the glucose measurement operation will be described. First, by displaying the standby of "adhering of blood", the blood drop is adhered onto adhering portion 506 (FIG. 35) of blood sugar level sensor SC.

S511: it is checked whether the blood drop is adhered. For adhering the blood drop, first, skin of a finger or the like is stuck by using a separate puncture apparatus or the like, blood is effused from the skin. And then the effused blood is adhered onto adhering portion 506 of blood sugar level sensor SC. Normally, the amount of the adhered blood drop is equal to or less than 5 µL. In order to detect whether the blood drop is adhered, a detecting electrode for detecting inflow of the blood is disposed in the area called a supply channel through which the blood flows in the apparatus, the detecting electrode being independent from the working electrode and the counter electrode used for the glucose measurement. When the blood flows in the apparatus, the resistance value between the electrodes is changed, and thus it is possible to electrically detect the inflow. By disposing the detecting electrode at a more inner position of the supply channel than position of the working electrode or the counter electrode, the reliability and accuracy of the measurement is further improved.

S512: likewise, if the blood drop is detected by the detecting electrode, "Adhesion OK" is displayed.

S513: at the same time, the measurement is started.

S514: the countdown of the remaining time (seconds) until the measurement is complete is displayed. Normally, the measurement time is equal to or less than 10 seconds, and is mostly about 5 seconds.

S515: first, in order to measure a substance (also called an interfering substance or an INT substance) such as ascorbic acid having an effect on the glucose measurement, the application voltage is applied to the predetermined electrode of blood sugar level sensor SC.

S516: by applying the application voltage, the signal of the interfering substance is input from the reaction current of the interfering substance, the measurement (TNT measurement) is performed, and the measured value is stored in memory 568 (refer to FIG. 36).

S517: in order to measure the glucose level, the application voltage for glucose measurement is applied to the predetermined electrode.

S518: the glucose level is measured from the reaction current generated by the oxidation-reduction reaction (Glucose measurement). Specifically, switching section 560-1 of the electric circuit blocks switches the input signals from the respective electrodes, and inputs the signal corresponding to the oxidation-reduction reaction. The input signal is amplified and converted into a voltage through current/voltage conversion section (I/V conversion section) 560-2. Analog/digital conversion section (A/D conversion section) 560-3 converts the voltage as an analog value into a digital value. The digital information is fetched in control section 561, and is stored as the measured value of the glucose in memory 568. Even in the INT measurement and the hematocrit measurement to be described later, the measured values are obtained in basically the same method.

S519: subsequently, in order to measure the hematocrit value (Hct measurement), the application voltage for measuring the hematocrit value is applied to the predetermined electrode (FIG. 37C).

S520: the hematocrit value is measured, and is stored in memory 568.

S521: the temperature data is input from temperature sensor 540 provided in panel 503, and is stored in memory 568.

S522: the humidity data is input from humidity sensor 530 provided in panel 503, and is stored in memory 568.

S523: the glucose level under the reference condition is calculated from the above-mentioned INT measured value, glucose measured value, hematocrit measured value, and temperature measurement data. The glucose level is calculated by using the high accuracy calculation data table (referred to as the calibration curve) for calculating the glucose level which is corrected on the basis of the measured values. Alternatively, the glucose level is calculated in a calculation method using the regression equation, the multiple regression equation, or the combination thereof.

S524: the glucose level as a corrected result is displayed on display section 502. At this time, the temperature data and the humidity data at the time of the measurement are displayed on display section 502 (refer to FIG. 35). If the glucose level is out of the predetermined range, the level may be represented in a different color from that for representing the normal level. For example, the normal level is displayed in green, and the level out of the normal value range is displayed in yellow. Further, if the glucose level is particularly high (200 or more), the glucose level is displayed in orange, and thereby it is possible to intuitively recognize a state where the glucose level is high.

S525: the measured values of the humidity data are checked.

S526: if the humidity is high, the caution display of "high humidity caution" is performed. For example, if the humidity is equal to or greater than 70%, the humidity data is displayer in different color (for example, yellow, orange, or the like) from that for displaying the normal data. Further, a message is also displayed, the message being for calling user's attention so as to prompt the user to appropriately house the blood sugar level sensor in the bottle designed for the sensor.

S527: when the measurement is finished, the blood sugar level sensor used for the measurement is discarded. Thereby, the measurement work is completed.

6. Embodiment 6

Figure 38:
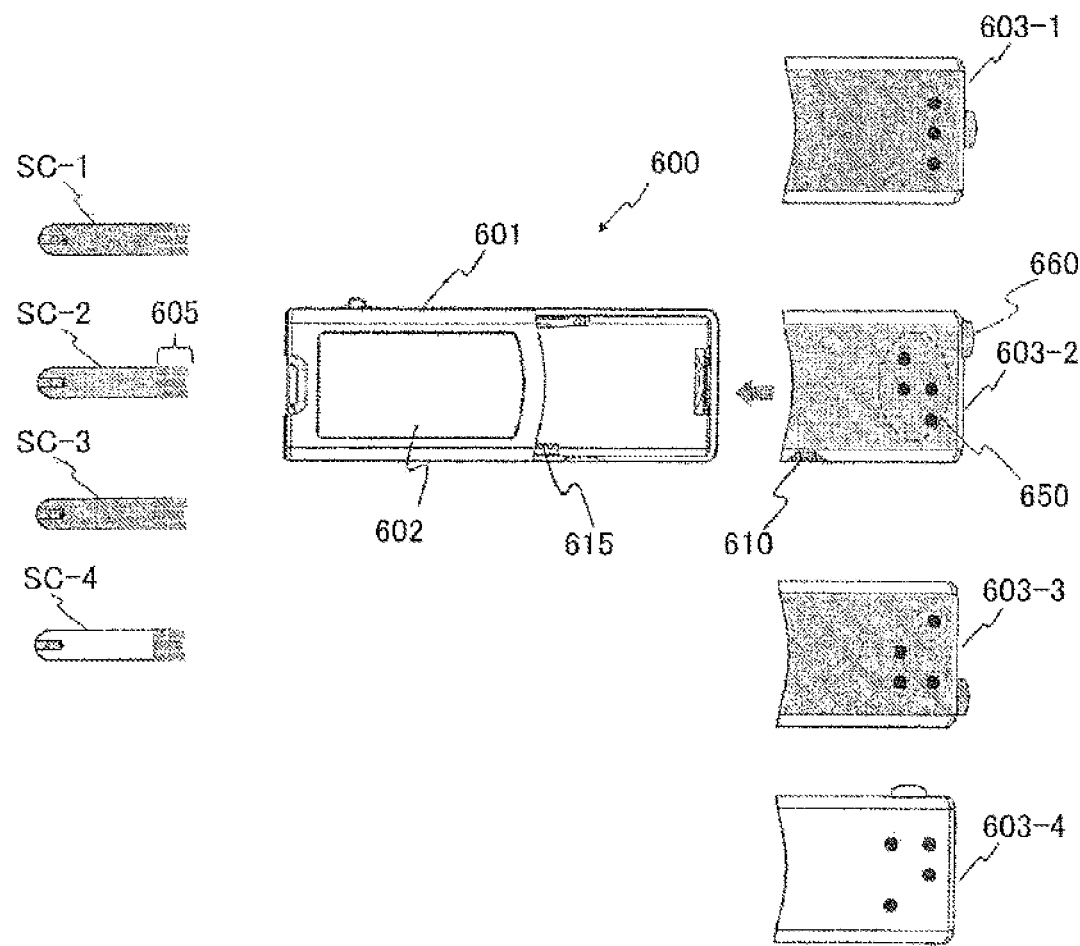
FIG. 38 is a front view illustrating a state in which a panel for measuring apparatus of the blood sugar level according to Embodiment 6 is detached.
Figure 39:
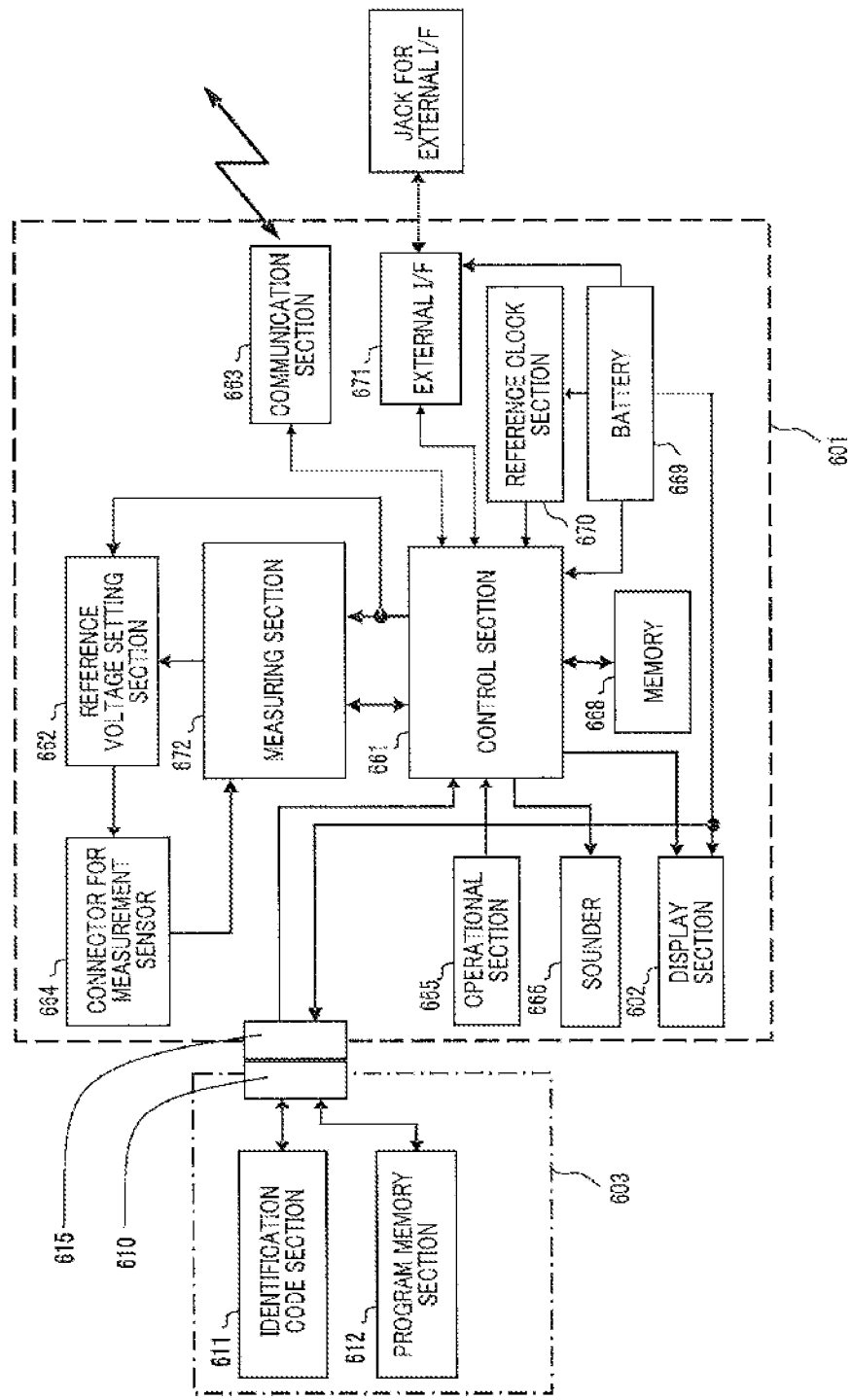
FIG. 39 is a configuration diagram of a control unit for measuring value of the blood sugar level according to Embodiment 6.

Referring to FIGS. 38 and 39, Embodiment 6 of the present invention will be described. The biological information measuring apparatus of FIGS. 38 and 39 is a measuring apparatus using a disposable biosensor, in which a measurement program and a measurement identification function are provided in the panel. Conventionally, for a patient who needs a plurality of types of measurements, it is necessary to provide the respective measuring apparatuses corresponding to the respective measurements. For this reason, there is a problem in portability, or there is a problem in that usability thereof is poor since the operation methods for the measuring apparatuses are different. In Embodiment 6, the problems are solved, and thus it is not necessary to provide the measuring apparatus for each type of the measurement, and it suffices to provide a panel for the corresponding measurement. That is, the measuring apparatus may be one.

Specifically, as shown in FIG. 38, there are provided 1) panel for glucose measurement 603-1, 2) panel for ketone measurement 603-2, 3) panel for lactate level measurement 603-3, and 4) panel for cholesterol measurement 603-4. In addition to this, hemoglobin A1c measurement panel and the like may be provided. Then, the panel is replaced with the corresponding panel for each measurement. Thereby, it is possible to perform desirable measurement.

Further, in each panel for each measurement, the identification code is provided; but dots 650 (for example, Braille) for identification may be further added on the exterior of the panel, protraction portion 660 for identification may be provided on the side of the panel, or the color of the panel surface may be set to be different. Thereby, a user is able to even visually and even haptically recognize the type of the measurement panel. In this way, it is possible to minimize human error.

Further, as shown in FIG. 38, there are provided 1) glucose sensor SC-1, 2) ketone measurement sensor SC-2, 3) lactate level measurement sensor SC-3, and 4) cholesterol measurement sensor SC-4. Furthermore, the surface color of the biosensor for each measurement is set to have the same color as the surface of the panel corresponding thereto. Thereby, the combination between the biosensor for measurement and the panel for measurement is visually recognized by a user.

When such a measurement biosensor (SC-1 or the like) is inserted into apparatus main body 601 of biological information measuring apparatus 600, control section 661 (refer to FIG. 39) of measuring apparatus main body 601 automatically determines whether or not the measurement target of mounted measurement panel (any one of 603-1 to 603-4) coincides with the measurement target of a measurement biosensor (any one of SC-1 to SC-4). If the measurement target of the measurement panel does not coincide with the measurement target of the measurement biosensor, a warning message is displayed on display section 602, and a warning sound is generated by sounder 666 (refer to FIG. 39). Thereby, a user is prompted to insert an appropriate measurement biosensor.

FIG. 39 shows an electric circuit block diagram of biological information measuring apparatus 600 shown in FIG. 38. In this example, panel for measurement 603 has a program memory section 612 (SD memory or the like) having a program for measurement built therein. When panel 603 is mounted, the measurement program of program memory section 612 is fetched in the program area as a part of memory section 668 of measuring apparatus main body 610 through connectors (including connection terminal 610 and connector for panel 615). Thereafter, the measurement is executed. The reading flow of the program is as shown in FIG. 5 in Embodiment 1 mentioned above.

With such a configuration, measuring apparatus 600 may be provided with the installation software for capturing the measurement program of program memory section 612 mounted on measurement panel 603. Further, at the time of replacing the program, when the program of panel 603 is updated to install a new program, it is not necessary to upgrade each measurement program of measuring apparatus 601.

When measurement sensor SC is inserted into measuring apparatus main body 601, the main power supply of apparatus main body 601 is turned ON. At that time, by displaying the name and the version of the program during a certain period of time (for example, about a time period in a range from 2 to 10 seconds), a user is able to view the measurement contents. The name and the version of the program may be notified with a voice generated by sounder 666.

In biological information measuring apparatus 600 of Embodiment 6, a user who needs a plurality of measurements provides with a plurality of measurement panels, whereby it is possible to improve the usability.

In an application example of Embodiment 6, it is possible to improve the efficiency of the manufacturing site. Specifically, measuring apparatus main body 601 may be equipped with only basic functions. That is, measuring apparatus main body 601 is used as a common platform by providing a common hardware. Then, the software as a specific measurement algorithm is stored in program memory section 612 which is mounted on each measurement panel 603.

Thereby, measurement panel 603 in which the corresponding measurement program is stored s mounted on common measuring apparatus main body 601. After final checking is performed thereon, the apparatus can be provided to a user. In this case, contrary to the above-mentioned example, it is preferable that measurement panel 603 mounted on measuring apparatus main body 601 be configured to be non-replaceable.

Thereby, measuring apparatus 600 having measurement panel 603 mounted thereon once is used as a dedicated apparatus. Therefore, mistakes and confusion in the market are prevented. Since the difference is clarified in design and visually and haptically, mistakes by the user are also prevented. According to this example, it is possible to improve the efficiency in the manufacturing of measuring device 600, and thus the hardware or the middleware of measuring apparatus main body 601 are set to be as common as possible. On the other hand, specific programs which are different for each measurement and the like are input into software mounted on program memory section 612 of each measurement panel 603. According to this embodiment, it becomes highly scalable, and the development period can be shortened in the future. And thus, there will be a merit in that a user will be promptly provided with the needed software.

7. Embodiment 7

Figure 40:
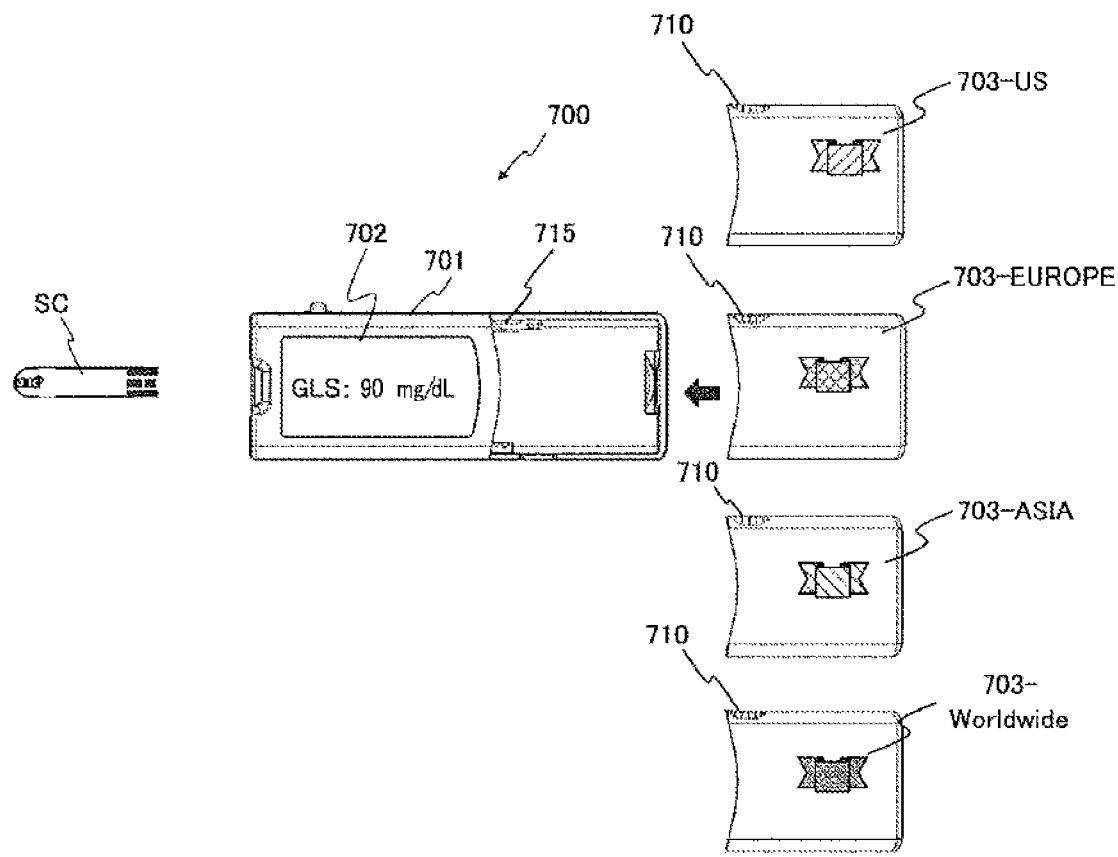
FIG. 40 is a front view illustrating a state in which a panel for measuring value of the blood sugar level according to Embodiment 7 is detached.

Referring to FIG. 40, Embodiment 7 of the present invention will be described. Embodiment 7 is an example in which the panel has a model code indicating a destination to and the like. That is, in Embodiment 7, the measurement itself is common (for example, glucose measurement), but the model code corresponding to each of the destination or the sale destination is mounted on the panel when shipping the panel (703-US, 703-EURO, 703-ASIA, 704-Worldwide).

Thereby, the appropriate language for each region may be displayed on the display section 702, or a voice notification of the appropriate language for each country may be given. In the case of the Worldwide panel, English is used in the display, and the voice notification of English is given. Further, an insurance system, criteria of medical equipments and the like are different among countries. Panels corresponding to each region, each country or each sale destination are provided. Therefore, it is possible to prevent blood sugar level sensor SC or measuring apparatus 700 from being used in an unauthorized region, and also it is possible to prevent blood sugar level sensor SC or measuring apparatus 700 distributed from the unauthorized region from being used. In such a manner, while measuring apparatus main body 701 is in common, it is possible to stabilize the distribution and the safety by regulating the availability in accordance with a region.

Even in this case, it is preferable that the panel once mounted cannot be replaced by a user. When the power supply of measuring apparatus 700 is turned ON, the destination, the sales company's name or the like is displayed for a certain period of time (for example, about a time period in a range from 2 to 10 seconds) so as to allow a user to confirm them. It is apparent that it is possible to provide the panel corresponding to each country and display in the corresponding language. In this case, the destination is based on countries, and is not based on regions.

8. Embodiment 8

Figure 41:
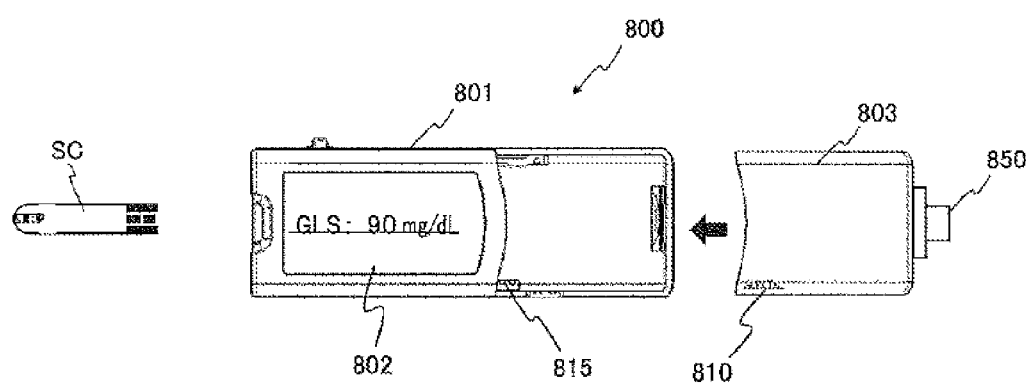
FIG. 41 is a front view illustrating a state in which a panel for measuring value of the blood sugar level according to Embodiment 8 is detached.

Referring to FIG. 41, Embodiment 8 of the present invention will be described. In Embodiment 8, there is provided biological information measuring apparatus 800 that includes: panel 803 having an interface (I/F) function for communicating with the outside; and measuring apparatus main body 801. Measuring apparatus main body 801 has display section 802 and the like. FIG. 41 shows panel 803 having USB connector 850. The memory section (like 568 of FIG. 36) of biological information measuring apparatus 800 stores the measurement data for a certain period of time (for example, a period of one month, or a period of time corresponding to measurements performed 1,000 times). By transferring the measurement data to the external devices such as a PC, it is possible to continuously perform administration. Thereby, the data is available for consulting a medical doctor or following the daily life of a patient. Panel 803 and measuring apparatus main body 801 are electrically connected through connection terminal 810 and connector 815. Here, the "measurement data" includes not only the glucose level, the interfering substance data, and the hematocrit (Hct) value, but also the date and time of the measurement, classification of before meals/after meals/between meals, the time elapsed after a meal, a user's memo (place, during work/during vacation, and the like), and the data relating to the measurement such as the temperature data and the humidity data.

In the case of the panel having the I/F function (for example, USB), by connecting to the external devices such as a PC, it is possible to simply transfer the data thereto. The transferred data can be displayed as a graph or a table with the software of the PC, whereby the data can be intuitively checked. Examples of I/F include not only USE but also Bluetooth (registered trademark), wireless LAN, Wi-Fi, Wimax, and the like. In addition, examples of the external devices other than the PC include a mobile phone such as a smart phone, a tablet, a PDA, and the like.

9. Embodiment 9

Figure 42:
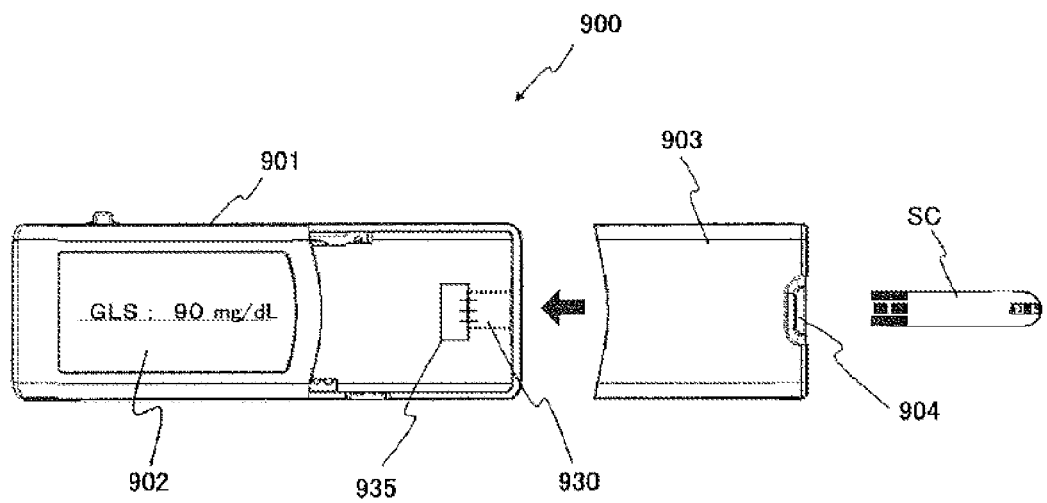
FIG. 42 is a front view illustrating a state in which a panel for measuring value of the blood sugar level according to Embodiment 9 is detached.

Referring to FIG. 42, Embodiment 9 of the present invention will be described. In Embodiment 9, there is provided biological information measuring apparatus 900 that has measuring apparatus main body 901 and replaceable panel 903, where panel 903 serves as a cover section of sensor insertion opening 904 of the disposable biosensor such as blood sugar level sensor SC. Measuring apparatus main body 901 includes display section 902, sensor insertion area 930, and sensor contact portion 935. By detaching panel 903 serving as the cover of sensor insertion opening 904, it is possible to wipe sensor contact portion 935 and the like with dirty or liquid such as blood adhered. Blood and the like tends to be adhered onto sensor contact portion 935 when blood sugar level sensor SC is mounted. In biological information measuring apparatus 900 of Embodiment 9, panel 903 serves as the cover of sensor insertion opening 904, thereby improving maintainability. Accordingly, the stability of the measuring apparatus is improved, the reliability is maintained, and thus the safety is improved.

10. Other Embodiment (10.1) The present embodiment shows an example in which RF-ID tag 7 (refer to FIG. 3) is disposed in panel 3 (refer to FIG. 3), but the present invention is not limited to this. RF-ID tag 7 may be provided on the replaceable designed panel which is constantly mounted on for example apparatus main body 1. Alternatively, RF-ID tag 7 may be provided on the replaceable exterior member mounted on apparatus main body 1, which are used for performing the blood sugar level measurement together with blood sugar level measuring apparatus 100.

In this case, when the designed panel or the exterior member are mounted on apparatus main body 1, RF-ID reading antenna 8 is arranged on apparatus main body 1 so as to face antenna 72 of RF-ID tag 7. By the arrangement, it is possible to realize the operation and the effects similar to any one of the above-mentioned embodiments.

(10.2) The present embodiment has been described focusing on the blood sugar level measuring apparatus. The biological information measuring apparatus according to the present invention is not limited to this. For example, the invention can be applied to various apparatuses that generate the measurement data relating to biological information such as blood pressure, pulse, and the components of lactic acid, cholesterol, uric acid, and the like.

(10.3) In Embodiment 1, RF-ID reading antenna 8 receives the control information from RF-II) tag 7 provided on panel 3, and control unit 10 reads and executes the corresponding control program on the basis of the control information. The present invention is not limited to this. Control program (predetermined information) itself may be stored in RF-ID tag 7 on panel 3 or the other memory. In this case, RF-ID reading antenna 8 may receive the control program from RF-ID tag 7 in response to determination as to whether panel 3 is mounted, and control unit 10 may store the receive control program in program memory 12, and may read and execute the same control program.

(10.4) In the present embodiment, apparatus main body 1 communicates with panel 3 so as to identify panel 3 The present invention is not limited to this. For example, panel 3 may be identified based on the electrically connection of panel 3 with apparatus main body 1 through the connector. Alternatively, panel 3 may be identified by reading the predetermined unevenness pattern provided on panel 3 by optical or mechanical reading means provided on apparatus main body 1. In this case, it is not necessary for the communication means to be provided in apparatus main body 1 or panel 3, and the memory may not be provided in panel 3. With such a configuration, it is possible to simply achieve reduction in costs.

(10.5) In Embodiment 1, the number of functions which can be executed when panel 3 is mounted on apparatus main body 1 may be a plurality of functions, may not be one.

(10.6) The configurations or the process contents of blood sugar level measuring apparatuses according to Embodiments 1 to 4 may be combined.

INDUSTRIAL APPLICABILITY

The biological information measuring apparatus according to the present invention is useful as an apparatus that performs the measurement relating to biological information such as blood sugar level, lactic acid, cholesterol, uric acid, blood pressure and pulse.

The invention claimed is:

1. A biological information measuring apparatus for acquiring biological information and generating measurement data relating to the biological information, the biological information measuring apparatus comprising:
an apparatus main body; and
a panel that is detachably mounted on the apparatus main body, wherein
the apparatus main body has a control unit that executes a plurality of functions in the apparatus main body, a biological information measuring section that is connected to the control unit and generates the measurement data, and a first communication unit that is connected to the control unit,
the panel has a second communication unit that includes a memory in which predetermined information is stored,
when the panel is mounted on the apparatus main body, the first communication unit receives the predetermined information from the second communication unit,
the control unit selects and executes at least one of the plurality of functions corresponding to the received predetermined information,
the predetermined information is a control program which executes the at least one of the functions executed by the control unit,
the control unit further has a data storage section that stores the measurement data, and
the control program is a program for executing a function of preventing the measurement data from being stored in the data storage section.

2. A biological information measuring apparatus for acquiring biological information and generating measurement data relating to the biological information, the biological information measuring apparatus comprising:
an apparatus main body; and
a panel that is detachably mounted on the apparatus main body, wherein
the apparatus main body has a control unit that executes a plurality of functions in the apparatus main body, a biological information measuring section that is connected to the control unit and generates the measurement data, and a first communication unit that is connected to the control unit,
the panel has a second communication unit that includes a memory in which predetermined information is stored,
when the panel is mounted on the apparatus main body, the first communication unit receives the predetermined information from the second communication unit,
the control unit selects and executes at least one of the plurality of functions corresponding to the received predetermined information,
the predetermined information is a control program which executes the at least one of the functions executed by the control unit,
the apparatus main body further has a main body display section that is connected to the control unit and displays the measurement data, and
the control program is a program for executing a function of displaying the measurement data on the main body display section.

3. A biological information measuring apparatus for acquiring biological information and generating measurement data relating to the biological information, the biological information measuring apparatus comprising:
an apparatus main body; and
a panel that is detachably mounted on the apparatus main body, wherein
the apparatus main body has a control unit that executes a plurality of functions in the apparatus main body, a biological information measuring section that is connected to the control unit and generates the measurement data, and a first communication unit that is connected to the control unit,
the panel has a second communication unit that includes a memory in which predetermined information is stored,
when the panel is mounted on the apparatus main body, the first communication unit receives the predetermined information from the second communication unit,
the control unit selects and executes at least one of the plurality of functions corresponding to the received predetermined information,
the predetermined information is a control program which executes the at least one of the functions executed by the control unit,
the apparatus main body further has a communication section that is connected to the control unit and communicates with a different apparatus, and
the control program is a program that transmits the measurement data from the communication section to the different apparatus.

4. A biological information measuring apparatus for acquiring biological information and generating measurement data relating to the biological information, the biological information measuring apparatus comprising:
an apparatus main body; and
a panel that is detachably mounted on the apparatus main body, wherein
the apparatus main body has a control unit that executes a plurality of functions in the apparatus main body, a biological information measuring section that is connected to the control unit and generates the measurement data, and a first communication unit that is connected to the control unit,
the panel has a second communication unit that includes a memory in which predetermined information is stored,
when the panel is mounted on the apparatus main body, the first communication unit receives the predetermined information from the second communication unit,
the control unit selects and executes at least one of the plurality of functions corresponding to the received predetermined information,
the predetermined information is a control program which executes the at least one of the functions executed by the control unit, the apparatus main body further has a main body display section that is connected to the control unit and that displays information which is arbitrarily selected, and the control program is a program for displaying a menu for a medical staff on the main body display section and is for performing a process by the medical staff.

5. A biological information measuring apparatus for acquiring biological information and generating measurement data relating to the biological information, the biological information measuring apparatus comprising:

an apparatus main body; and a panel that is detachably mounted on the apparatus main body, wherein the apparatus main body has a control unit that executes a plurality of functions in the apparatus main body, a biological information measuring section that is connected to the control unit and generates the measurement data, and a first communication unit that is connected to the control unit, the panel has a second communication unit that includes a memory in which predetermined information is stored, when the panel is mounted on the apparatus main body, the first communication unit receives the predetermined information from the second communication unit, the control unit selects and executes at least one of the plurality of functions corresponding to the received predetermined information, the apparatus main body has a voice output section that is connected to the control unit, and the control unit causes the voice output section to output a voice on the basis of the received predetermined information.

6. The biological information measuring apparatus according to claim 5, wherein the panel has a sound output section, when the panel is mounted on the apparatus main body, the control unit and the sound output section are connected with each other, and the control unit causes the sound output section to output data as an audible sound on the basis of the received predetermined information, the data relating to measurement of the biological information.

7. A biological information measuring apparatus for acquiring biological information and generating measurement data relating to the biological information, the biological information measuring apparatus comprising:

an apparatus main body; and a panel that is detachably mounted on the apparatus main body, wherein the apparatus main body has a control unit that executes a plurality of functions in the apparatus main body, a biological information measuring section that is connected to the control unit and generates the measurement data, and a first communication unit that is connected to the control unit, the panel has a second communication unit that includes a memory in which predetermined information is stored, when the panel is mounted on the apparatus main body, the first communication unit receives the predetermined information from the second communication unit, the control unit selects and executes at least one of the plurality of functions corresponding to the received predetermined information, the apparatus main body further has an alarm section that is connected to the control unit and sounds an alarm, and the control unit causes the alarm section to sound the alarm, when the control unit determines that communication between the first communication unit and the second communication unit is suspended on a basis of fact that at least one of conditions of (i) a predetermined time or more passes from the determination that the communication is suspended and (ii) the measurement data represents an abnormal value is satisfied.

8. A biological information measuring apparatus for acquiring biological information and generating measurement data relating to the biological information, the biological information measuring apparatus comprising:

an apparatus main body; and a panel that is detachably mounted on the apparatus main body, wherein the apparatus main body has a control unit that executes a plurality of functions in the apparatus main body, a biological information measuring section that is connected to the control unit and generates the measurement data, and a first communication unit that is connected to the control unit, the panel has a second communication unit that includes a memory in which predetermined information is stored, when the panel is mounted on the apparatus main body, the first communication unit receives the predetermined information from the second communication unit, the control unit selects and executes at least one of the plurality of functions corresponding to the received predetermined information, the apparatus main body further has a main body display section that is connected to the control unit and displays information which is arbitrarily selected, and the control unit causes the main body display section to display warning information, when the control unit determines that communication between the first communication unit and the second communication unit is suspended on a basis of fact that at least one of conditions of (i) a predetermined time or more passes from the determination that the communication is suspended and (ii) the measurement data represents an abnormal value is satisfied.

9. A biological information measuring apparatus for acquiring biological information and generating measurement data relating to the biological information, the biological information measuring apparatus comprising:

an apparatus main body; and a panel that is detachably mounted on the apparatus main body, wherein the apparatus main body has a control unit that executes a plurality of functions in the apparatus main body, a biological information measuring section that is connected to the control unit and generates the measurement data, and a first communication unit that is connected to the control unit, the panel has a second communication unit that includes a memory in which predetermined information is stored, when the panel is mounted on the apparatus main body, the first communication unit receives the predetermined information from the second communication unit, the control unit selects and executes at least one of the plurality of functions corresponding to the received predetermined information, the apparatus main body further has a communication section that is connected to the control unit and communicates with a different apparatus, and has a current position acquisition section that is connected to the control unit and acquires a current position information of the apparatus, and the control unit transmits the current position information from the communication section to a different apparatus, when the control unit determines that communication between the first communication unit and the second communication unit is suspended on a basis of fact that at least one of conditions of (i) a predetermined time or more passes from the determination that the communication is suspended and (ii) the measurement data represents an abnormal value is satisfied.

10. A biological information measuring apparatus for acquiring biological information and generating measurement data relating to the biological information, the biological information measuring apparatus comprising:

an apparatus main body; and a panel that is detachably mounted on the apparatus main body, wherein the apparatus main body has a control unit that executes a plurality of functions in the apparatus main body, a biological information measuring section that is connected to the control unit and generates the measurement data, and a first communication unit that is connected to the control unit, the panel has a second communication unit that includes a memory in which predetermined information is stored, when the panel is mounted on the apparatus main body, the first communication unit receives the predetermined information from the second communication unit, the control unit selects and executes at least one of the plurality of functions corresponding to the received predetermined information, the apparatus main body further has a communication section that is connected to the control unit and communicates with a different apparatus, and the control unit acquires instruction information based on the measurement data from the different apparatus through the communication section, when the control unit determines that communication between the first communication unit and the second communication unit is suspended on a basis of fact that at least one of conditions of (i) a predetermined time or more passes from the determination that the communication is suspended and (ii) the measurement data represents an abnormal value is satisfied.

11. A biological information measuring apparatus for acquiring biological information and generating measurement data relating to the biological information, the biological information measuring apparatus comprising:

an apparatus main body; and a panel that is detachably mounted on the apparatus main body, wherein the apparatus main body has a control unit that executes a plurality of functions in the apparatus main body, a biological information measuring section that is connected to the control unit and generates the measurement data, and a first communication unit that is connected to the control unit, the panel has a second communication unit that includes a memory in which predetermined information is stored, when the panel is mounted on the apparatus main body, the first communication unit receives the predetermined information from the second communication unit, the control unit selects and executes at least one of the plurality of functions corresponding to the received predetermined information, the panel further has a function display section that displays function information corresponding to the predetermined information the apparatus main body further has a main body display section that is connected to the control unit and displays information which is arbitrarily selected, and the control unit causes the main body display section to display information corresponding to the function information displayed on the function display section of the panel.

12. The biological information measuring apparatus according to claim 11, wherein the apparatus main body has a dial on a side portion thereof, and when the panel is mounted on the apparatus main body, the control unit causes the main body display section to display an information relating to measurement performed by the apparatus main body or the function information on the main body display section according to an operation of the dial.

13. The biological information measuring apparatus according to claim 11, wherein the function information displayed on the function display section of the panel represents an operation manual of the apparatus.

14. The biological information measuring apparatus according to claim 13, wherein while the biological information is measured by the apparatus main body, the control unit causes the main body display section to display the operation manual describing a process of the measurement in accordance with measurement progress performed by the apparatus main body.

* * * * *